(12) United States Patent
Cheng et al.

(10) Patent No.: US 11,014,953 B2
(45) Date of Patent: May 25, 2021

(54) TRIGGER-ACTIVATABLE METABOLIC SUGAR PRECURSORS FOR CANCER-SELECTIVE LABELING AND TARGETING

(71) Applicant: The Board of Trustees of the University of Illinois, Urbana, IL (US)

(72) Inventors: Jianjun Cheng, Champaign, IL (US); Hua Wang, Somerville, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/767,070

(22) PCT Filed: Oct. 7, 2016

(86) PCT No.: PCT/US2016/056046
§ 371 (c)(1),
(2) Date: Apr. 9, 2018

(87) PCT Pub. No.: WO2017/062800
PCT Pub. Date: Apr. 13, 2017

(65) Prior Publication Data
US 2018/0298047 A1    Oct. 18, 2018

Related U.S. Application Data

(60) Provisional application No. 62/238,326, filed on Oct. 7, 2015.

(51) Int. Cl.
| | |
|---|---|
| *C07H 15/26* | (2006.01) |
| *C07H 15/18* | (2006.01) |
| *A61K 47/55* | (2017.01) |
| *A61P 35/00* | (2006.01) |
| *G01N 33/574* | (2006.01) |

(52) U.S. Cl.
CPC ........... *C07H 15/26* (2013.01); *A61K 47/552* (2017.08); *A61P 35/00* (2018.01); *C07H 15/18* (2013.01); *G01N 33/57492* (2013.01)

(58) Field of Classification Search
CPC ....... A61K 47/552; C07H 15/26; C07H 15/18
See application file for complete search history.

(56) References Cited

U.S. PATENT DOCUMENTS

| | | |
|---|---|---|
| 2008/0132458 A1 | 6/2008 | Matteucci et al. |
| 2010/0160299 A1 | 6/2010 | Baker, Jr. et al. |
| 2014/0010763 A1 | 1/2014 | Shabat et al. |
| 2014/0031535 A1 | 1/2014 | Jeffrey |
| 2014/0046051 A1 | 2/2014 | Vrasidas et al. |
| 2016/0184459 A1 | 6/2016 | Ueki et al. |

FOREIGN PATENT DOCUMENTS

WO    WO-2014/065661 A1    5/2014

OTHER PUBLICATIONS

Chang (Journal of the American Chemical Society; 132; 28; 2010; 9516-9518).*
Amsberry et al., "Amine prodrugs which utilize hydroxy amide lactonization. I. A potential redox-sensitive amide prodrug," Pharmaceut Res, 8(3):323-330 (1991).
International Search Report and Written Opinion for International Application No. PCT/US16/56046 dated Dec. 27, 2016.
Partial Supplementary European Search Report for EP Application No. EP 16854444 dated Dec. 19, 2019.
Extended European Search Report for EP Application No. 16854444.3 dated Mar. 31, 2020.
Shim et al., "Cathepsin B-Specific Metabolic Precursor for In Vivo Tumor-Specific Fluorescence Imaging," Angew. Chem. Int. Ed., 55:14698-14703, Oct. 2016.
Wang et al., "A Caged Metabolic Precursor for DT-Diaphoraseresponsive Cell Labeling," Chem Commun (Camb)., 54(38):4878-4881, May 2018.

* cited by examiner

*Primary Examiner* — Pancham Bakshi
(74) *Attorney, Agent, or Firm* — Haukaas Fortius PLLC; Michael H. Haukaas

(57) ABSTRACT

Disclosed are compounds for the selective labeling of cell-surface sugars in cancer cells. The compounds are activatable by triggers specific to cancer cells, and, when metabolized, label a cancer cell surface sugar with an azide chemical group. Facilitated by a click chemistry reaction, combination of the cell surface-expressed azide with a alkynyl-drug conjugate enables efficient targeted drug delivery to cancer cells with reduced toxicity. Also disclosed are compounds for delivering a drug to an azide-bearing cancer cell, and methods of treating cancer using the compounds of the invention.

6 Claims, 18 Drawing Sheets

Figure 2, continued
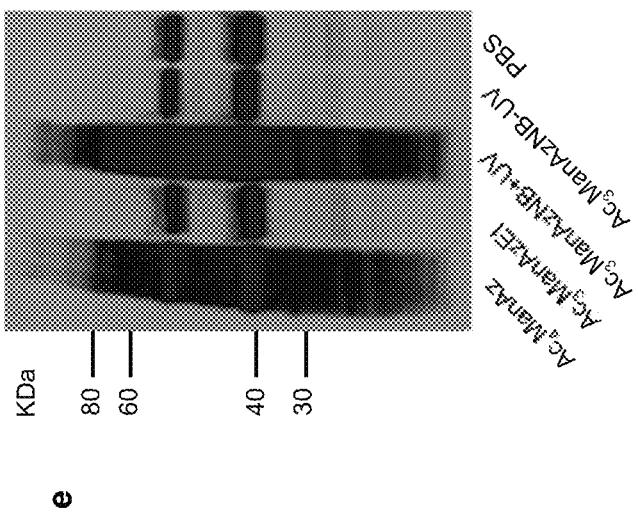
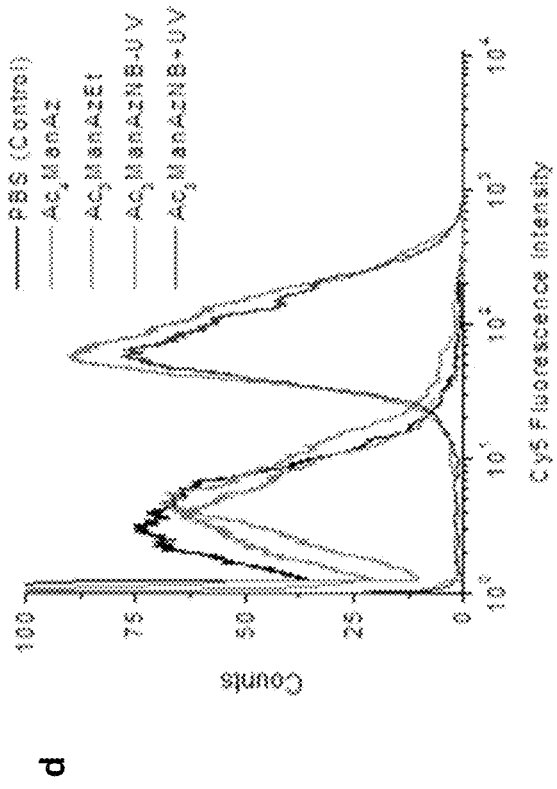

Figure 6
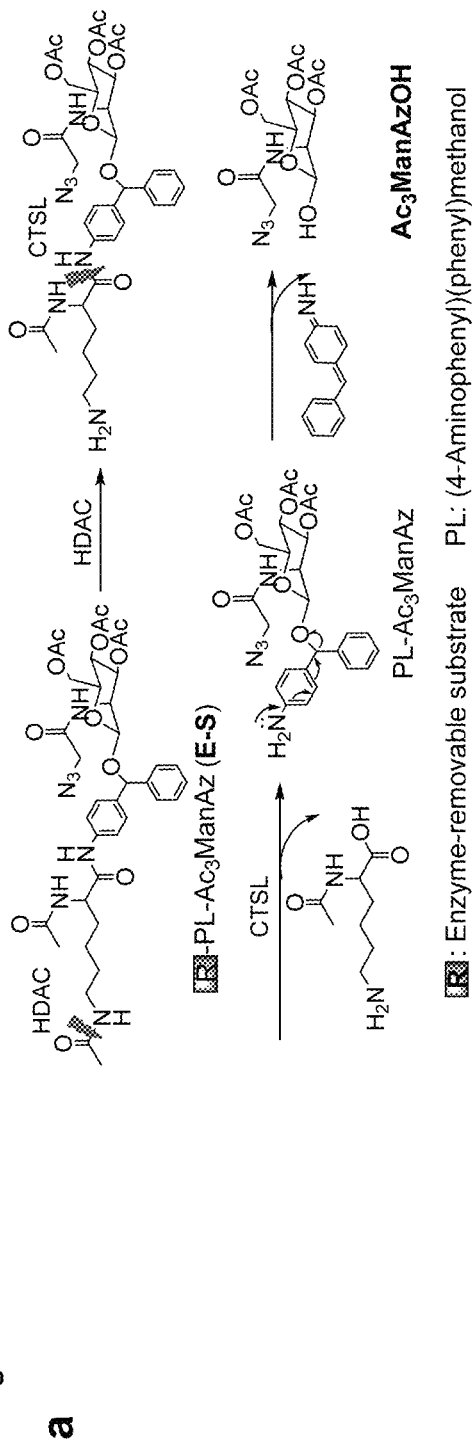
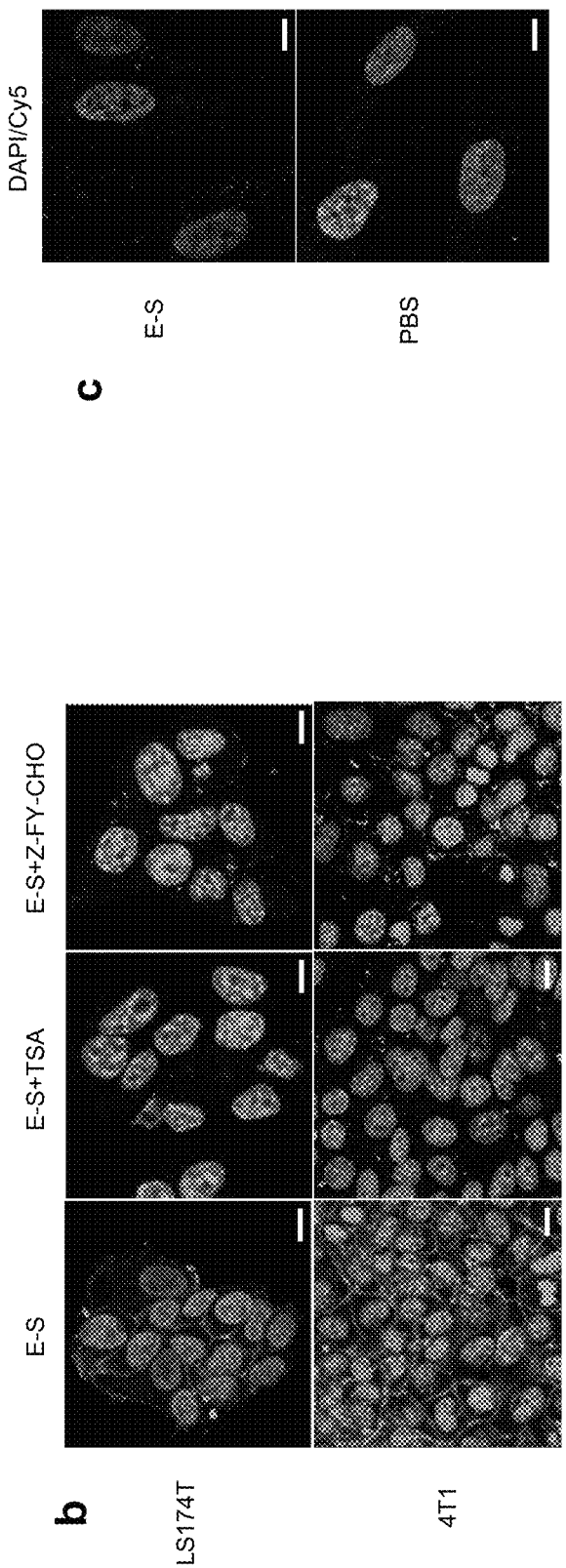

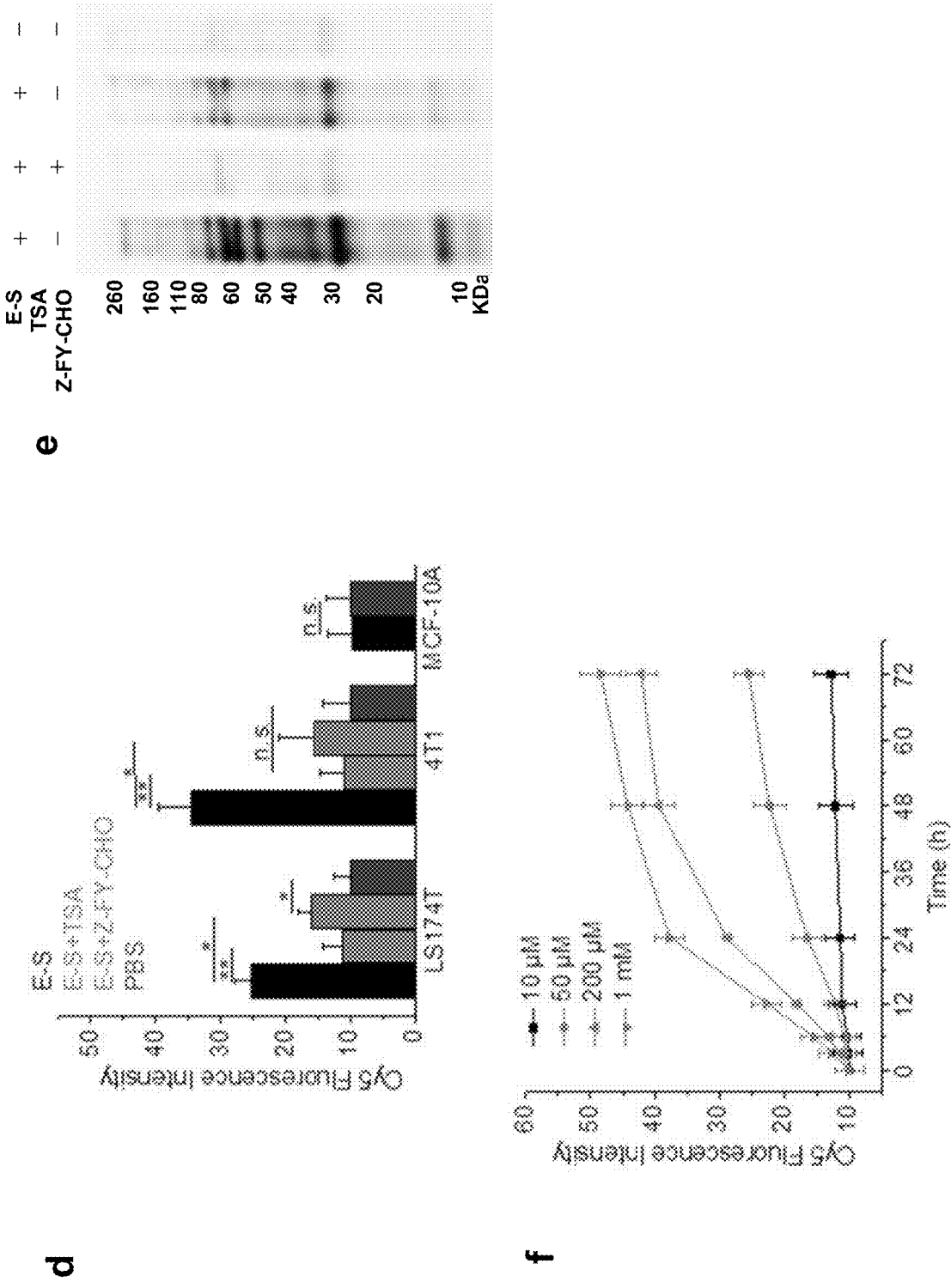
Figure 6, continued

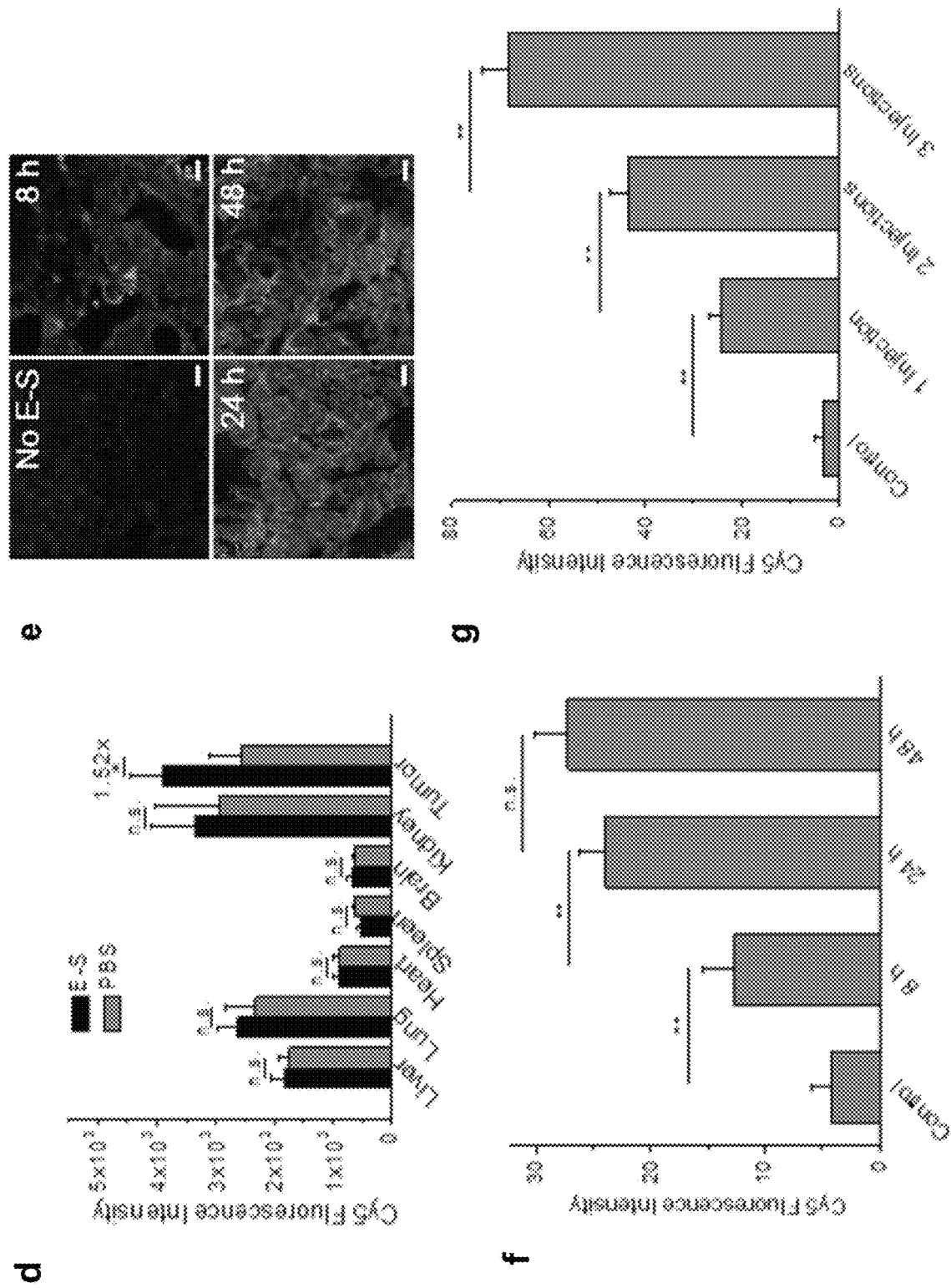
Figure 7, continued

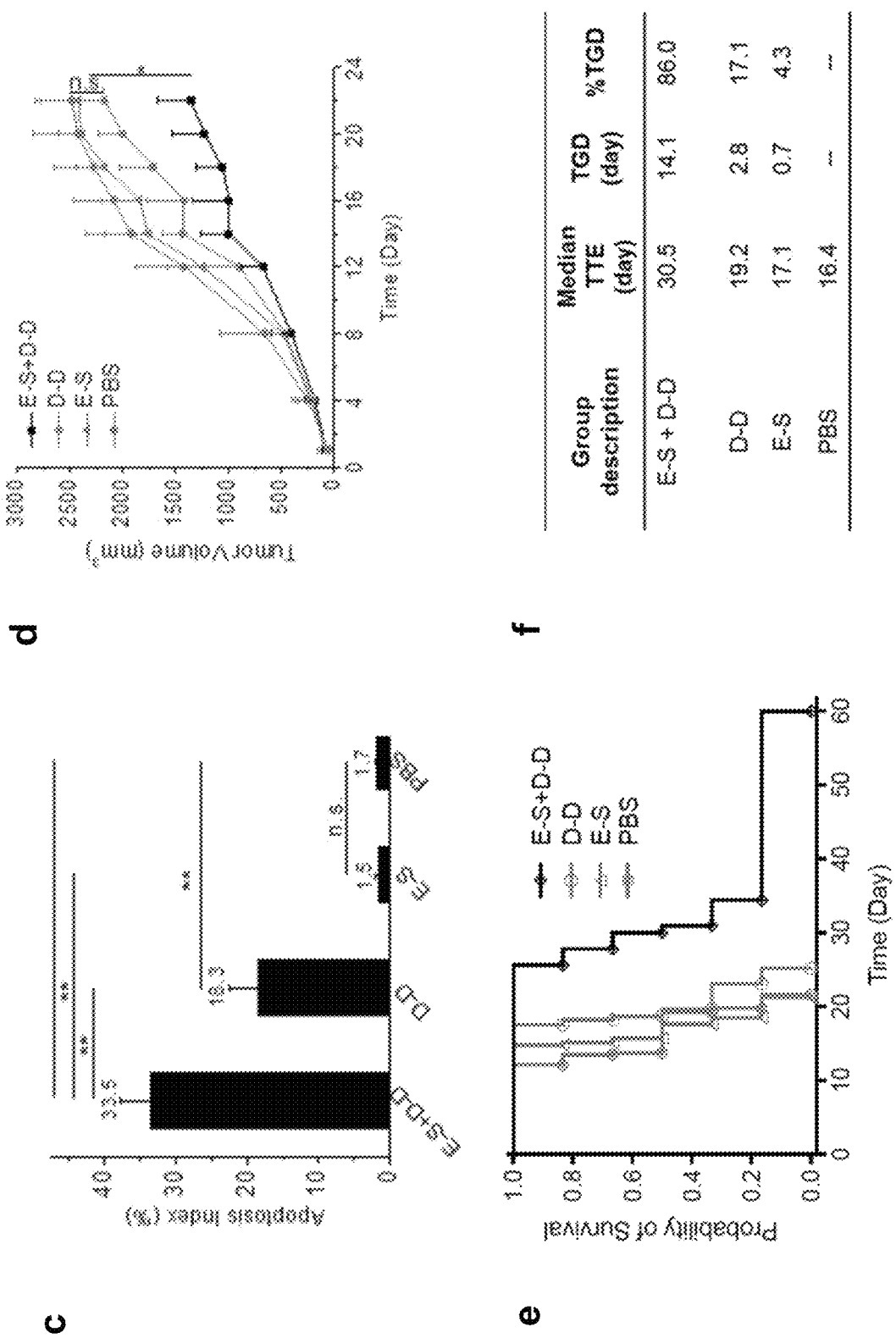
Figure 8, continued

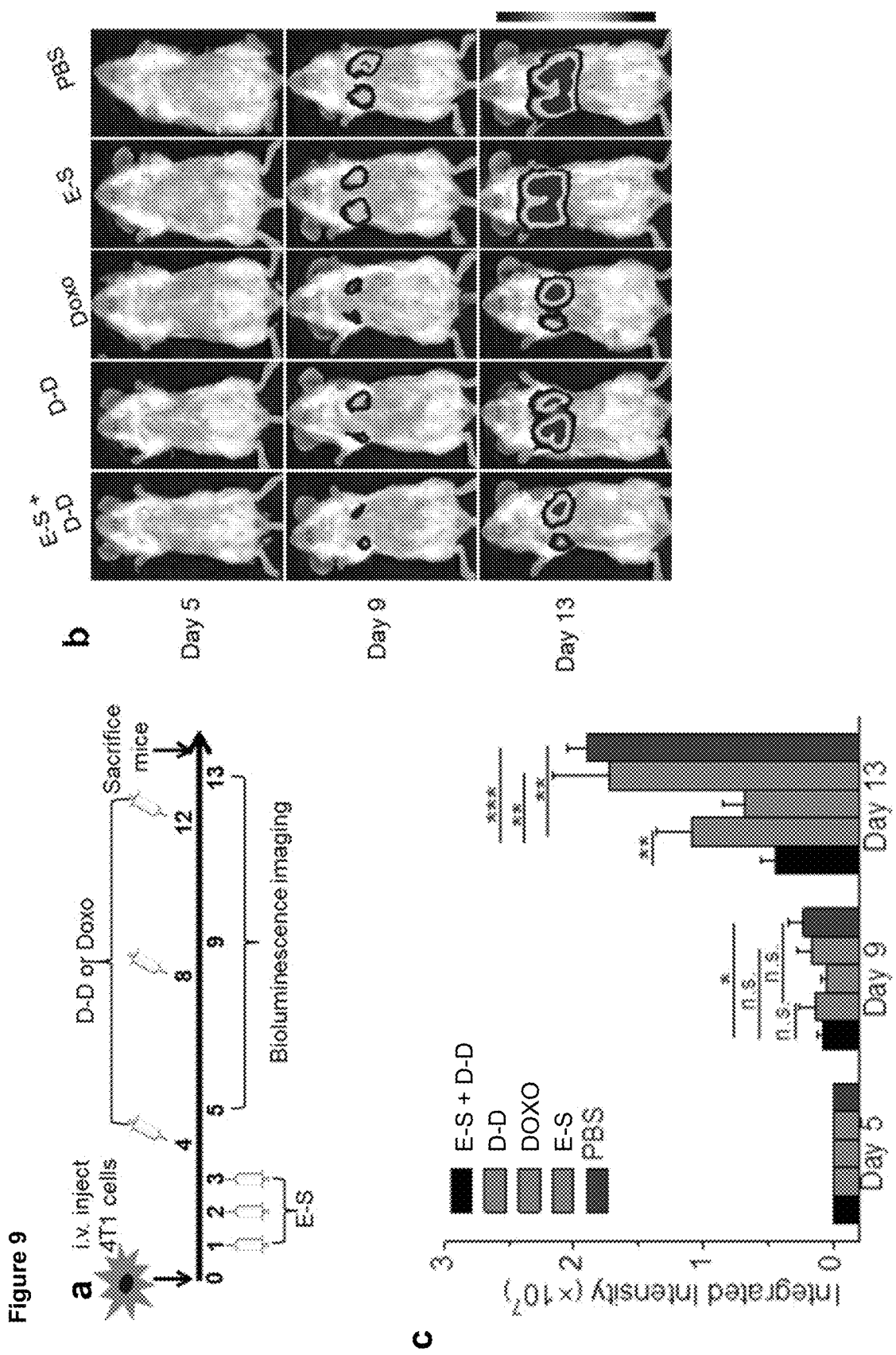

Figure 9, continued
d
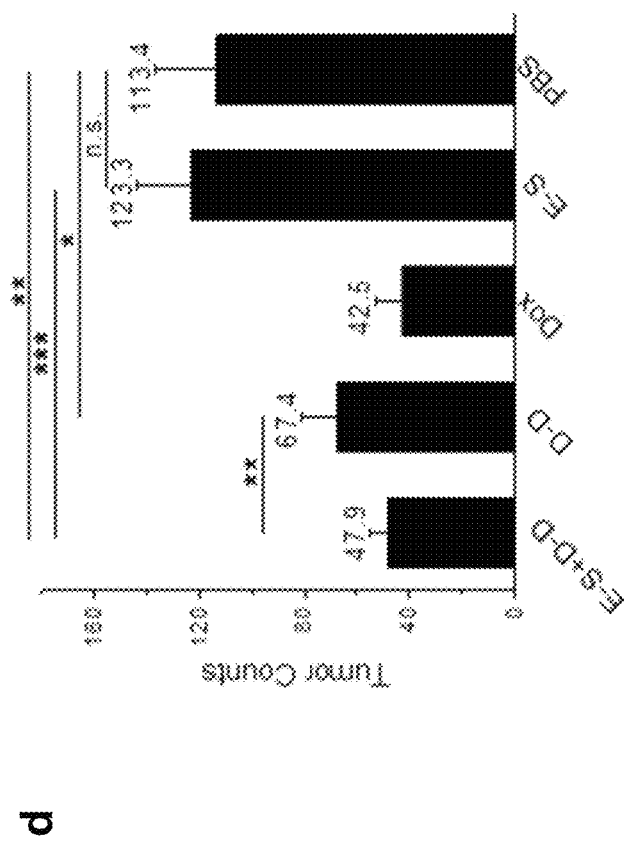
e
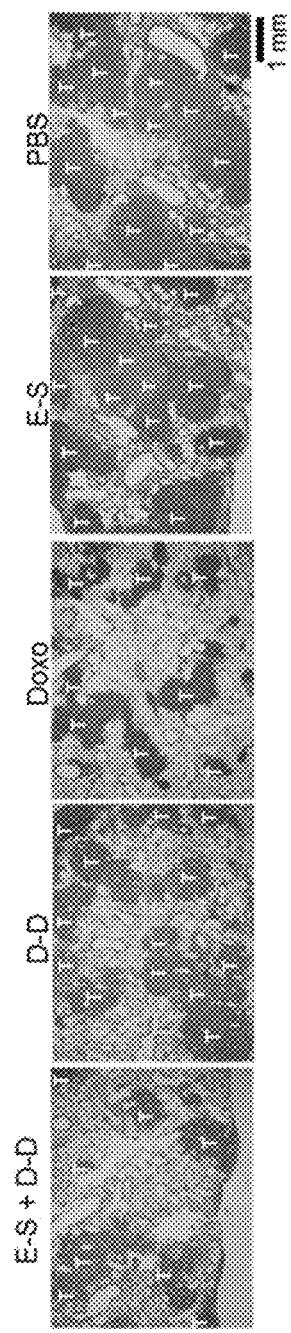

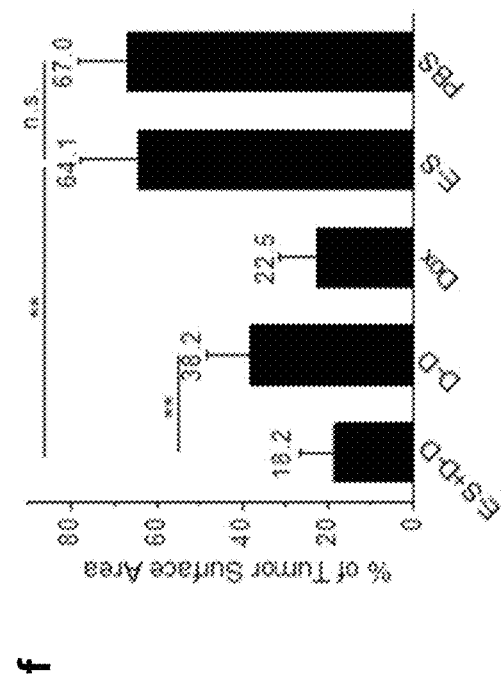
Figure 9, continued

Figure 11
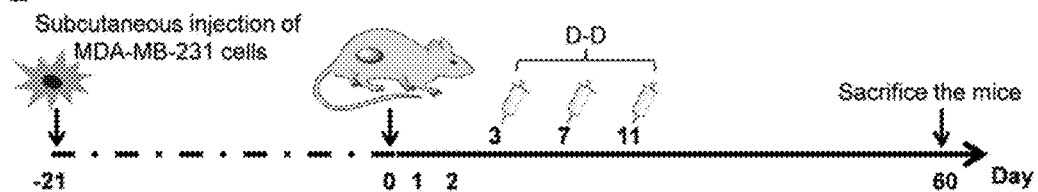
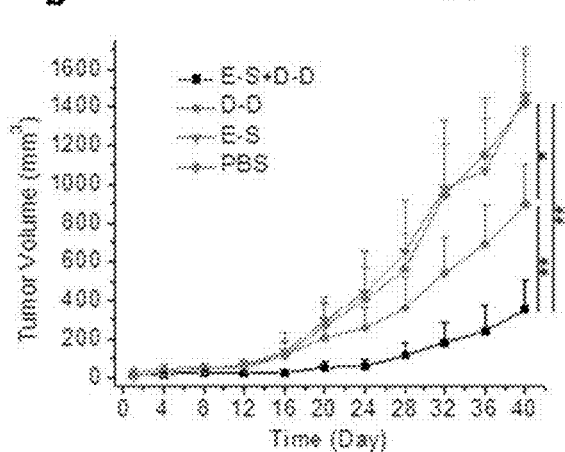
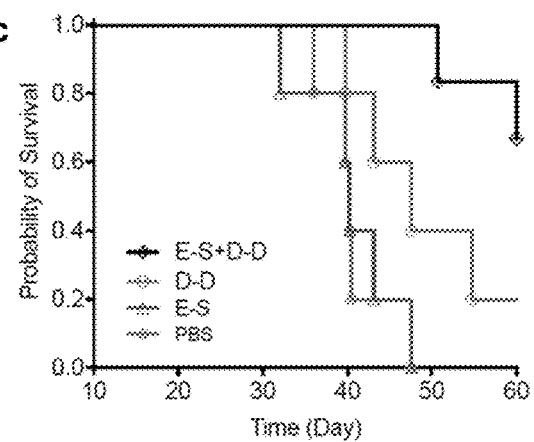
| Group description | Median TTE (day) | TGD (day) | %TGD |
|---|---|---|---|
| E-S + D-D | 60.0 | 23.1 | 62.6 |
| D-D | 47.6 | 10.7 | 29.0 |
| E-S | 38.0 | 1.1 | 3.0 |
| PBS | 36.9 | -- | -- |
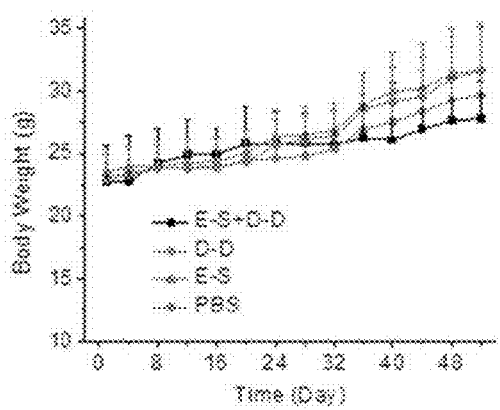

| Equation | y = a + b*x | Adj. R-Sq | 0.9656 |
|---|---|---|---|
|  |  | Value | Standard Error |
| B | Intercept | 5380.75202 | 2285.71161 |
| B | Slope | 8508.78271 | 921.77202 |

TRIGGER-ACTIVATABLE METABOLIC SUGAR PRECURSORS FOR CANCER-SELECTIVE LABELING AND TARGETING

RELATED APPLICATIONS

This application claims the benefit of priority to U.S. Provisional Patent Application No. 62/238,326, filed Oct. 7, 2015, which application is hereby incorporated by reference in its entirety.

BACKGROUND OF THE INVENTION

Cancer targeted therapy has long been pursued to improve the accumulation of drugs in cancers and minimize their undesired exposure to other parts of the body. The key challenge lies in the identification of unique receptors in cancer tissues and the development of corresponding targeting ligands. Several types of targeting ligands have been developed, and include small molecules, peptides, and aptamers. However, their corresponding receptors are rarely cancer-specific, and the binding affinity between protein receptors and these ligands is relatively low. The most promising targeting ligands developed thus far are monoclonal antibodies (mAb). Advances in this area have made it possible to create mAbs specific to extracellular/cell surface proteins, and several cancer-exclusive proteins have been identified. Despite being the most successful targeting ligands in clinic, mAbs suffer from multiple drawbacks such as high production cost, large size, severe immunogenicity, receptor saturation, and poor solid tumor penetration. In addition, each mAb developed only works well for certain types of cancer because the targeted protein receptors vary from cancer to cancer.

Notably, a common characteristic among all the existing active targeting strategies is that cell surface proteins are regarded as the target. This selection makes sense since proteins provide multiple hydrophobic and charged sites for specific binding with the targeting ligands. However, the number density of cell surface proteins is much lower as compared to sugars and lipids, the other two major components on the cell membrane. Surface-pendant sugars represent a promising target, and are already known to play a vital role in regulating cellular recognition and communication. It was recently discovered that unnatural sugars (e.g., tetraacetyl N-azidoacetylmannosamine ($Ac_4ManAz$)) can be metabolically expressed on the cell surface.[1-11] However, these metabolic labeling processes of unnatural sugars occur in normal cells as well as cancer cells, so there exists a significant challenge in rendering this metabolic labeling process selective or exclusive to cancer cells.

Therefore, there exists a need to develop sugars that can be selectively metabolically expressed on the cell surface of cancer cells. There also exists a need to develop further agents and methods for treating cancer that can take advantage of a selective metabolic labeling process.

SUMMARY OF THE INVENTION

One aspect of the invention provides compositions and methods useful for expressing an azidosugar (e.g., an azido sialic acid; see Figures) on the cell surface of cancer cells. Accordingly, an aspect of the invention is a compound or a pharmaceutically acceptable salt thereof, comprising an optionally substituted N-((azido)acyl) 2-amino-2-deoxy-D-mannopyranosyl moiety, a trigger-responsive moiety that is cleaved by a trigger, and a self-immolative linker, wherein the self-immolative linker is covalently bonded to the mannopyranosyl moiety and to the trigger-responsive moiety.

In certain aspects, such a compound is represented by formula (I) or a pharmaceutically acceptable salt thereof:

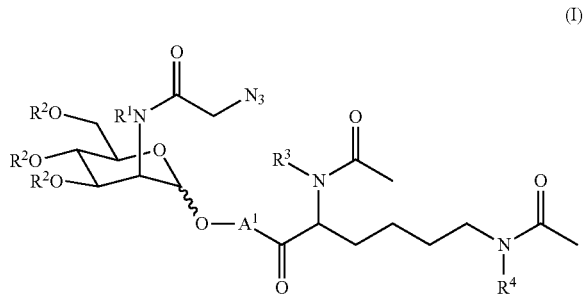

(I)

wherein:
R$^1$ represents H or tri(($C_1$-$C_6$)alkyl)silyl;
R$^2$, independently for each occurrence, represents H or —C(O)(($C_1$-$C_6$)alkyl);
R$^3$ and R$^4$, independently for each occurrence, represent H, tri(($C_1$-$C_6$)alkyl)silyl, or —C(O)(($C_1$-$C_6$)alkyl);
A$^1$ represents the self-immolative linker; and
m is 1, 2, or 3.

In other aspects, the invention provides a compound represented by formula (III) or a pharmaceutically acceptable salt thereof:

$$K\text{-Pol-Pep-}A^2\text{-D} \qquad (III);$$

wherein:
K represents an optionally substituted cycloalkynyl, heterocycloalkynyl, or alkynyl moiety;
Pol represents an polymeric moiety;
Pep represents an amino acid or oligopeptide sequence;
A$^2$ represents a self-immolative linker; and
D represents a pharmacophore;
wherein:
the polymeric moiety is a polyalkylene glycol or polyalkylene imide; and
the amino acid or oligopeptide sequence comprises an amide bond that is cleaved by an enzyme (i) overexpressed in a malignant cell relative to a counterpart healthy cell or (ii) expressed in a malignant cell that is not expressed in a counterpart healthy cell.

In other aspects, the invention provides a pharmaceutical composition, comprising a compound of the invention (e.g., a compound of formula (I) or formula (III)), and a pharmaceutically acceptable excipient or carrier.

In other aspects, the invention relates to methods of expressing an azidosugar (e.g., an azido sialic acid) in a malignant tissue in a mammal, comprising administering to a mammal with malignant tissue an effective amount of a compound comprising an optionally substituted N-((azido)acyl) 2-amino-2-deoxy-D-mannopyranosyl moiety, a trigger-responsive moiety that is cleaved by a trigger, and a self-immolative linker (e.g., a compound of formula (I)).

In other aspects, the invention relates to methods of treating cancer, comprising administering to a subject in need thereof an effective amount of a compound comprising an optionally substituted N-((azido)acyl) 2-amino-2-deoxy-D-mannopyranosyl moiety, a trigger-responsive moiety that is cleaved by a trigger, and a self-immolative linker (e.g., a compound of formula (I)).

In other aspects, the invention relates to methods of treating cancer, comprising administering to a subject in need thereof an effective amount of a compound of formula (III).

BRIEF DESCRIPTION OF THE DRAWINGS

FIG. 6 depicts HDAC/CTSL responsive E-S mediated controlled cell labeling in vitro. Panel (a) shows a schematic illustration of HDAC/CTSL-induced degradation of E-S. Panel (b) is a series of CLSM images of LS174T colon cancer cells and 4T1 breast cancer cells after incubated with 50 μM E-S, 50 μM E-S+1 μM TSA, and 50 μM E-S+50 μM Z-FY-CHO, respectively for 72 h and labeled with DBCO-Cy5 (50 μM) for 1 h. The cell nucleus was stained with DAPI. Scale bar represents 10 μm. Panel (c) contains CLSM images of IMR-90 human fibroblast cells after incubated with 50 μM E-S or PBS for 72 h and labeled with DBCO-Cy5 for 1 h. The cell nucleus was stained with DAPI. Scale bar: 10 μm. Panel (d) is a bar graph showing the average Cy5 fluorescence intensity of LS174T cells or IMR-90 cells with different treatments. Data were presented as mean±SEM and analyzed by one-way ANOVA (Fisher; 0.01<*P≤0.05; P≤0.01;  P≤0.001). Panel (e) is a western blot analysis of LS174T cells treated with E-S, E-S+TSA, E-S+Z-FY-CHO, and PBS, respectively. Cell lysates were incubated with DBCO-Cy5 for 1 h at 37° C. prior to running a gel. Protein bands were visualized using ImageQuant LAS 4010 system. Panel (f) is a graph showing concentration- and time-dependent E-S labeling in LS174T cells. Cells were treated with various concentrations of E-S (10 μM, 50 μM, 200 μM, and 1 mM) for different time (0 h, 1 h, 3 h, 6 h, 12 h, 24 h, 48 h, and 72 h), and labeled with DBCO-Cy5 (50 μM) for 2 h.

FIG. 9 consists of panels a-g, demonstrates that E-S mediated tumor labeling shows improved antitumor efficacy of DBCO-drug conjugate against 4T1 metastatic tumor model. Panel (a) shows the time frame of the efficacy study. 4T1 metastatic tumors were established on Balb/c mice by i.v. injection of luciferase-engineered 4T1 breast cancer cells. E-S was i.v. injected once daily for three days (Day 1, 2, and 3), and drug was i.v. administered on Day 4, 8, and 12. Panel (b) depicts bioluminescence imaging of Balb/c mice with different treatments on Day 5, 9, and 13, respectively. Panel (c) is a graph showing change of integrated bioluminescence intensity of mice with different treatments over time. Panel (d) is a graph showing average tumor counts on lung tissues from different groups. Panel (e) shows representative pictures of lung tissues from different groups. Panel (f) is a bar graph showing the percentage of tumor surface area over total lung tissue area for different groups. Panel (g) contains representative images of bone marrow and spleen sections, which showed significantly reduced systemic toxicity of E-S+D-D groups compared to free Doxo. Al the numerical data were presented as mean±SEM (n=7-8) and analyzed by one-way ANOVA (Fisher; 0.01<*P≤0.05;  P≤0.01;  P≤0.001).

FIG. 11 consists of panels a-e and depicts the results of a long-term antitumor efficacy study of E-S+D-D in athymic nude mice bearing subcutaneously implanted MDA-MB-231 tumors. Panel (a) depicts the time frame of the tumor reduction study. E-S (60 mg/kg) was i.v. injected on Day 0, 1, and 2. D-D (12 mg/kg in DOXO equivalent) was i.v. injected on day 3, 7, and 11. Tumor size, body weight, and food intake of mice were closely monitored. Panel (b) graphs the average MDA-MB-231 tumor size of each group over the course of the long-term efficacy study. Data were presented as mean±SEM. Significance analyses were conducted by one-way ANOVA (Fisher; 0.01<*P≤0.05; P≤0.01; *P≤0.001). Panel (c) contains Kaplan-Meier plots for all groups. Loss of mice was because of treatment-related death or non-treatment-related death or euthanasia after the predetermined end point was reached. Panel (d) provides a survival analysis of athymic nude mice in each group. TTE: time to end point. TGD: tumor growth delay; TGD=TTE (treated group)−TTE (PBS group). % TGD=100%×TGD/TTE (PBS group). Panel (e) is a chart showing body weight of mice from different groups over the course of the efficacy study. Curves were truncated when two or more mice were dead or sacrificed.

DETAILED DESCRIPTION

Cancer targeted therapy has long been pursued to improve the accumulation of drugs in cancers and minimize their undesired exposure to other parts of the body. However, existing cancer-targeting technologies are not satisfactory for therapeutic applications. Though most existing cancer-targeting strategies utilize cancer cell surface proteins as the target, we sought to explore cancer cell surface sugars as therapeutic target, in part because of their higher cell-surface density. Metabolic glycoengineering processes of unnatural sugars provides a facile method to introduce chemical groups onto a cell surface, which enables in-depth studies of otherwise elusive cellular biology questions such as cell internalization, cell fusion, and cell targeting. Disclosed herein are compounds and methods that facilitate controlled labeling of cancer cell-surface sugars, and further therapeutic compositions and methods that take advantage of such cancer-targeting capability.

Figure 1:
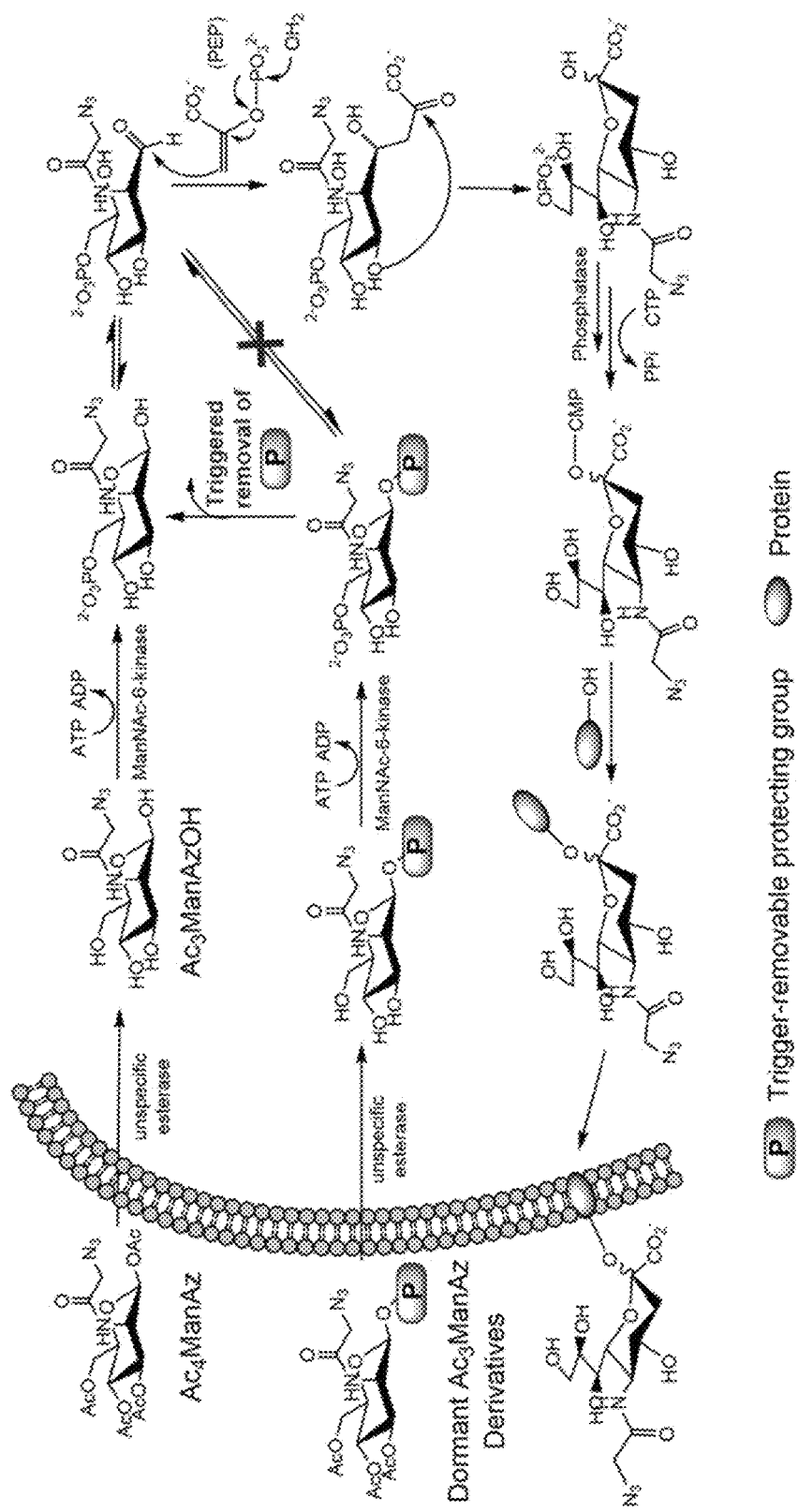
FIG. 1 is a scheme depicting the metabolic labeling process of $Ac_4ManAz$ and the trigger-activated labeling process of $Ac_3ManAz$ derivatives. P represents a protecting group.

The principles underlying this invention demonstrate that the metabolic labeling capability of azido-sugars can be controlled from the structure perspective. The metabolic labeling process of Ac$_4$ManAz is shown in FIG. 1. Ac$_4$ManAz is hydrolyzed by unspecific esterases upon entering the cells, followed by the phosphorylation of 6-OH and the ring-opening isomerization. Phosphoenolpyruvic acid (PEP) then attacks the newly-formed carbonyl group to form sialic acid which is then (1) deprived of the phosphate group, (2) conjugated to protein, and finally (3) expressed on the cell surface in the form of glycoprotein. It can be anticipated that the ring-opening isomerization step is essential for the successful metabolic labeling and that the exposure of the hydroxyl group at C1 site (1-OH) is necessary for the successful ring-opening isomerization. The inventors surprisingly discovered that modifying the C1 site of Ac$_4$ManAz by forming a glycosidic bond that would survive the cellular esterases prevents the ring-opening isomerization step, thus blocking the whole metabolic labeling process. By designing a trigger-responsive glycosidic (ether) bond that can expose the 1-OH in the presence of certain triggers, the metabolic labeling process can be controlled. Cancer selective chemical labeling can potentially be achieved by using Ac$_3$ManAz derivatives that are responsive to specific cancer-associated triggers. Exemplary cancer-associated triggers can include redox dysregulation, elevated oxidant level, and overexpressed enzymes.

Compounds of the Invention

An aspect of the invention relates to a compound or a pharmaceutically acceptable salt thereof, comprising:

an optionally substituted N-((azido)acyl) 2-amino-2-deoxy-D-mannopyranosyl moiety;

a trigger-responsive moiety that is cleaved by a trigger; and a self-immolative linker;

wherein the self-immolative linker is covalently bonded to the mannopyranosyl moiety and to the trigger-responsive moiety.

In certain embodiments, the trigger is heightened, over-expressed, or otherwise enhanced in a cancerous tissue relative to a healthy tissue.

In certain embodiments, the trigger is cellular peroxide.

Figure 5:
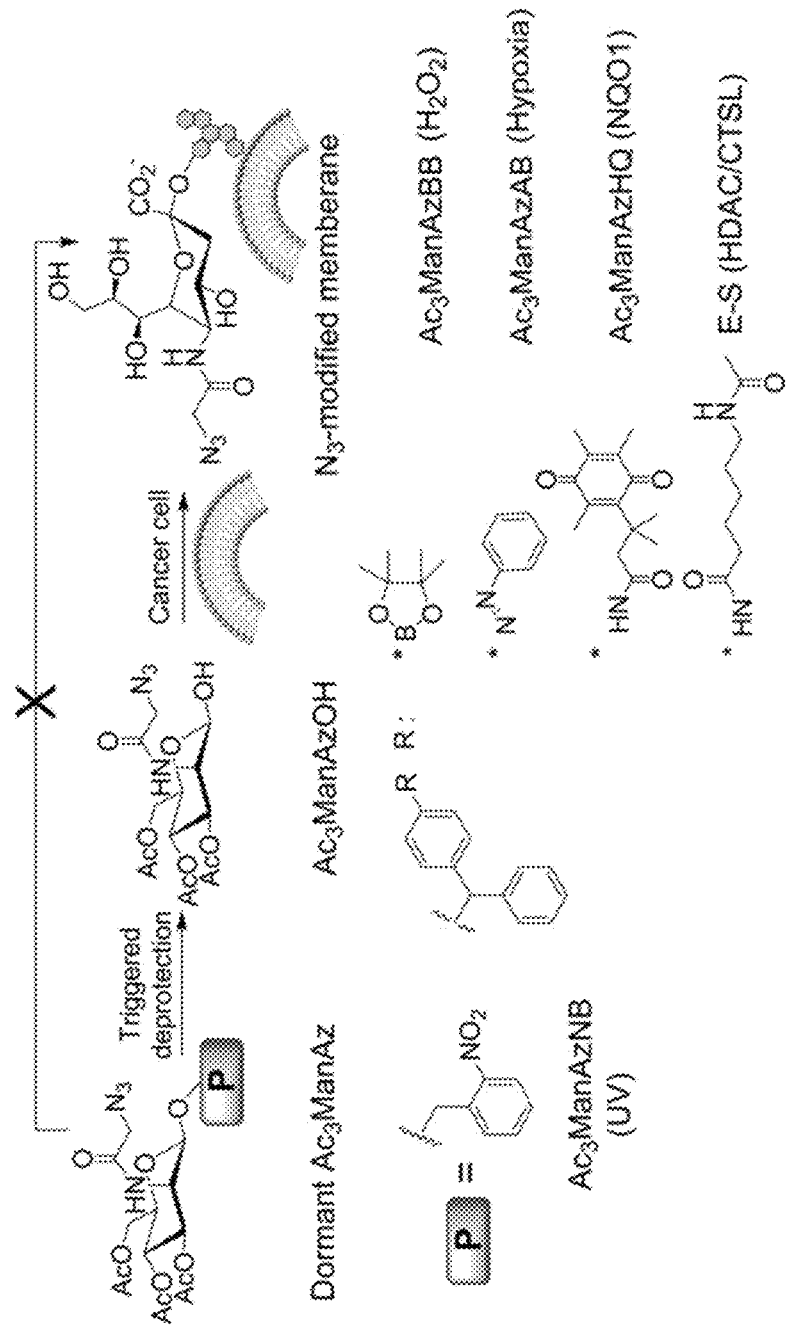
FIG. 5 depicts a library of trigger-activatable $Ac_3ManAz$ derivatives ($H_2O_2$-responsive $Ac_3ManAzBB$, hypoxia-responsive $Ac_3ManAzAB$, NQO1-responsive $Ac_3ManAzHQ$, and HDAC/CTSL-responsive E-S) for controlled cell labeling.

In certain such embodiments, the trigger-responsive moiety comprises a boronic acid group, a dialkyl boronate group, a diaryl boronate group, a di(aralkyl)boronate group, a borolane group, or a dioxaborolane group. An exemplary embodiment is shown in FIG. 5.

In certain such embodiments, upon cleavage of the trigger-responsive moiety by cellular peroxide the self-immolative linker disassembles, thereby releasing an optionally substituted N-((azido)acyl) 2-amino-2-deoxy-D-mannopyranoside.

In alternative embodiments, the trigger is hypoxia.

In certain such embodiments, the trigger-responsive moiety comprises a 2-nitroimidazole moiety or an azo group, such as azobenzene. An exemplary embodiment is shown in FIG. 5.

In certain such embodiments, upon cleavage of the trigger-responsive moiety under hypoxic conditions the self-immolative linker disassembles, thereby releasing an optionally substituted N-((azido)acyl) 2-amino-2-deoxy-D-mannopyranoside.

In alternative embodiments, the trigger is a sulfhydryl- or thiolate-containing compound, such as glutathione.

In certain such embodiments, the trigger-responsive moiety comprises a disulfide bond. An exemplary embodiment is shown below:

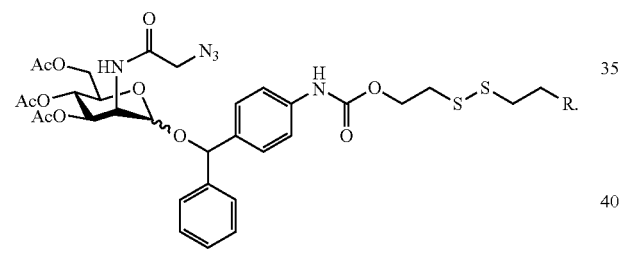

In certain such embodiments, upon cleavage of the disulfide bond by a sulfhydryl- or thiolate-containing compound the self-immolative linker disassembles, thereby releasing an optionally substituted N-((azido)acyl) 2-amino-2-deoxy-D-mannopyranoside.

In alternative embodiments, the trigger is NAD(P)H dehydrogenase (quinone 1) (NQO1).

In certain such embodiments, the trigger-responsive moiety comprises an optionally substituted quinone, covalently bound to an optionally substituted propionic acid or propionic amide moiety. An exemplary embodiment is shown in FIG. 5.

In certain such embodiments, upon cleavage of the optionally substituted quinone, covalently bound to an optionally substituted propionic acid or propionic amide moiety by NAD(P)H dehydrogenase (quinone 1) (NQO1) the self-immolative linker disassembles, thereby releasing an optionally substituted N-((azido)acyl) 2-amino-2-deoxy-D-mannopyranoside.

In certain embodiments, the trigger is a cathepsin enzyme.

In certain such embodiments, the trigger-responsive moiety is an amino acid or oligopeptide sequence comprising an amide bond that is a cleaved by a cathepsin enzyme.

In further embodiments, the trigger-responsive group comprises an acid-sensitive moiety, such as an imine, acetal, ketal, or carbamate. Exemplary trigger-responsive groups are depicted in the embodiments shown below:

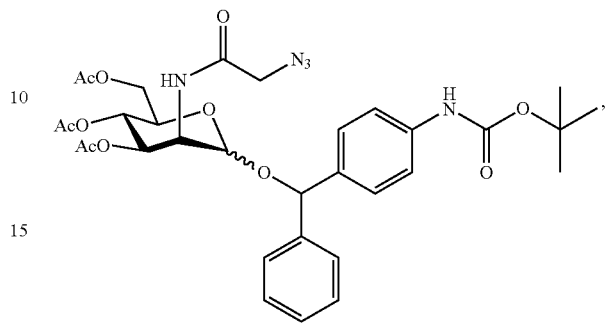

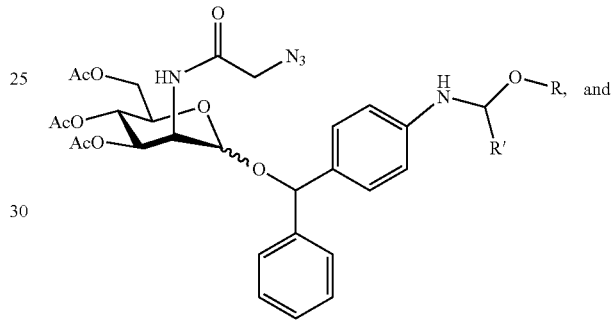

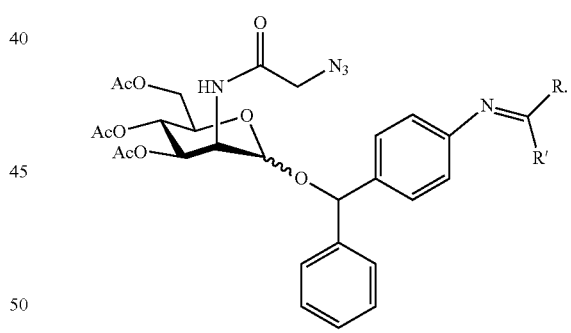

In certain such embodiments, the amino acid or oligopeptide sequence comprising an amide bond comprises Phe-Lys, Val-Lys, Ala-Lys, Val-Cit, Phe-Cit, Leu-Cit, Ile-Cit, Trp-Cit, Phe-Arg(NO$_2$), Phe-Arg(Ts). Cit represents citrulline, and Ts represents a tosylate protecting group.

In certain embodiments, the amino acid or oligopeptide sequence is a substituted lysine amide.

In certain such embodiments, upon cleavage of the amide bond by the cathepsin enzyme the self-immolative linker disassembles, thereby releasing an optionally substituted N-((azido)acyl) 2-amino-2-deoxy-D-mannopyranoside.

In certain embodiments, the cathepsin enzyme is cathepsin L.

In certain embodiments, the compound is represented by formula (I) or a pharmaceutically acceptable salt thereof:

(I)

wherein:
R$^1$ represents H or tri((C$_1$-C$_6$)alkyl)silyl;
R$^2$, independently for each occurrence, represents H or —C(O)((C$_1$-C$_6$)alkyl);
R$^3$ and R$^4$, independently for each occurrence, represent H, tri((C$_1$-C$_6$)alkyl)silyl, or —C(O)((C$_1$-C$_6$)alkyl);
A$^1$ represents the self-immolative linker; and
m is 1, 2, or 3.

In certain embodiments, R$^1$ represents H.
In certain embodiments, R$^2$, independently for each occurrence, represents H or —C(O)CH$_3$.
In certain embodiments, all occurrences of R$^2$ are identical.
In certain embodiments, R$^3$ and R$^4$ are H.
In certain embodiments, m is 1.

The compounds of the invention include a self-immolative linker that spaces and covalently links together the mannopyranosyl moiety and the trigger-responsive moiety. The self-immolative linker is a bifunctional chemical moiety, capable of covalently linking together two spaced chemical moieties (i.e., the mannopyranosyl moiety and the trigger-responsive moiety) into a normally stable tripartite molecule. The self-immolative linker enables the release of one of the spaced chemical moieties from the tripartite molecule by means of trigger-induced cleavage (e.g., enzymatic cleavage); and such cleavage, can spontaneously cleave from the remainder of the molecule to release the other of the spaced chemical moieties.

In certain embodiments:
A$^1$ represents a group —X$^1$—Y$^1$—;
X$^1$ represents a bond or —C(O)$_2$—;
Y$^1$ represents a bond or optionally substituted —((C$_1$)alkylene)-arylene- or —((C$_1$)alkylene)-heteroarylene-; and
X$^1$ and Y$^1$ do not both represent a bond.

In certain such embodiments, Y$^1$ represents optionally substituted —((C$_1$)alkylene)-arylene-.

In certain such embodiments, the self-immolative linker is selected from the group consisting of:

wherein
R$^5$ represents H, tri((C$_1$-C$_6$)alkyl)silyl, or —C(O)((C$_1$-C$_6$)alkyl);
R$^6$ represents H, (C$_1$-C$_6$)alkyl, or heterocycloalkyl;
R$^7$ represents H, halo, —C(O)$_2$H, (C$_1$-C$_6$)alkoxy, di((C$_1$-C$_6$)alkyl)amino, —NO$_2$, —O(CH$_2$CH$_2$O)$_q$CH$_3$; and
q is 1 or 2.

In certain such embodiments, R$^7$ is H.
In certain embodiments, the self-itnmolative linker is In certain such embodiments, the self-immolative linker is

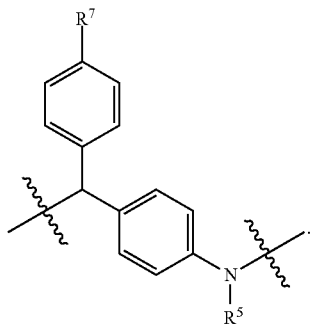

In further such embodiments, $R^7$ is H.

In alternative embodiments, the self-immolative linker is selected from

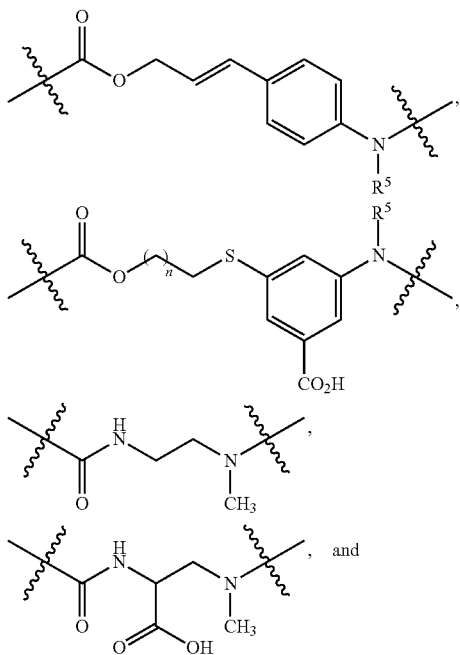

and

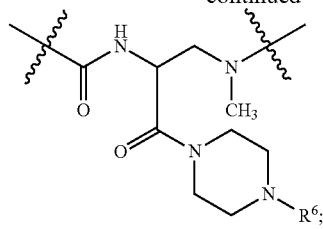

wherein $R^5$ represents H, tri(($C_1$-$C_6$)alkyl)silyl, or —C(O)(($C_1$-$C_6$)alkyl)

$R^6$ represents H, ($C_1$-$C_6$)alkyl, or heterocycloalkyl; and n is 1 or 2.

In certain embodiments, the compound for expressing an azidosugar (e.g., an azido sialic acid) on the cell surface of cancer cells is represented by formula (II) or a pharmaceutically acceptable salt thereof:

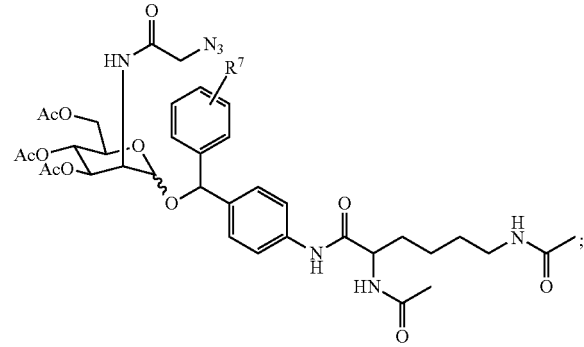

(II)

wherein $R^7$ represents H, halo, —C(O)$_2$H, ($C_1$-$C_6$)alkoxy, di(($C_1$-$C_6$)alkyl)amino, —NO$_2$, —O(CH$_2$CH$_2$O)$_q$CH$_3$; and q is 1 or 2.

In further embodiments, the compound is represented by formula (II') or a pharmaceutically acceptable salt thereof:

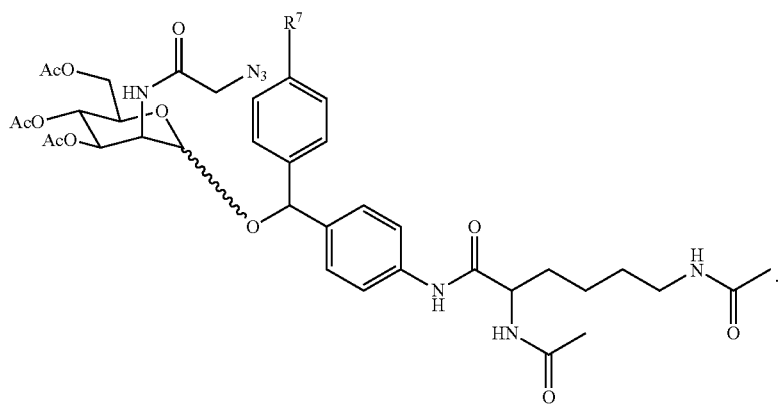

(II')

In further such embodiments, $R^7$ is H.

In other aspects, the invention relates to compounds that can deliver therapeutic agents selectively to cells that express an azidosugar (e.g., an azido sialic acid) on their cell surface. Accordingly, in certain embodiments, the invention relates to a compound of formula (III):

K-Pol-Pep-A²-D        (III);

wherein:
K represents an optionally substituted cycloalkynyl, heterocycloalkynyl, or alkynyl moiety;
Pol represents an polymeric moiety;
Pep represents an amino acid or oligopeptide sequence;
A² represents a self-immolative linker; and
D represents a pharmacophore;
wherein:
the polymeric moiety is a polyalkylene glycol or polyalkylene imide; and
the amino acid or oligopeptide sequence comprises an amide bond that is cleaved by an enzyme (i) overexpressed in a malignant cell relative to a counterpart healthy cell or (ii) expressed in a malignant cell that is not expressed in a counterpart healthy cell.

In certain embodiments, upon cleavage of the amide bond by the enzyme, the self-immolative linker disassembles, thereby releasing the pharmacophore.

In certain embodiments, the enzyme is a cathepsin enzyme. For example, the enzyme can be cathepsin B.

In certain embodiments, Pep represents optionally substituted Val-Cit.

In certain embodiments, the compound of formula (III) is represented by formula (IV):

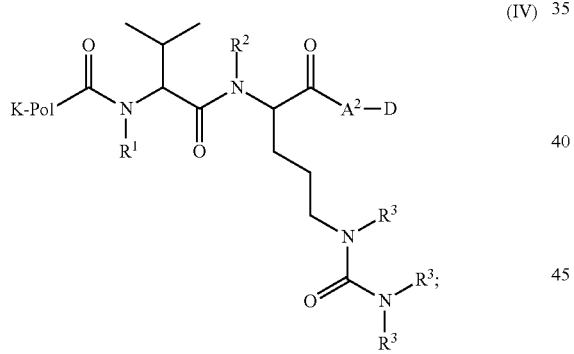

(IV)

wherein:
$R^1$, $R^2$, and $R^3$, independently for each occurrence, represent H, tri(($C_1$-$C_6$)alkyl)silyl, or —C(O)(($C_1$-$C_6$)alkyl).

In certain embodiments, $R^1$, $R^2$, and $R^3$ are H.

In certain embodiments, K comprises an optionally substituted heterocycloalkynyl or cycloalkynyl. In certain embodiments, K comprises an optionally substituted dibenzocyclooctyne moiety.

In certain embodiments, Pol represents a polyethylene glycol or polypropylene glycol moiety.

In certain embodiments, Pol represents from 10 to 30 repeat units of polyethylene glycol or polypropylene glycol.

In certain embodiments, Pol represents from 10 to 30 repeat units of polyethylene glycol, or from 15 to 25 repeat units of polyethylene glycol.

In certain embodiments,
A² represents a group —Y²—X²—;
X² represents a bond or —C(O)$_2$—;
Y² represents a bond or optionally substituted -arylene-(($C_1$)alkylene)- or -heteroarylene-(($C_1$)alkylene)-; and
X² and Y² do not both represent a bond.

In certain embodiments, Y² represents optionally substituted -arylene-(($C_1$)alkylene)-.

In certain such embodiments, the self-immolative linker is selected from the group consisting of:

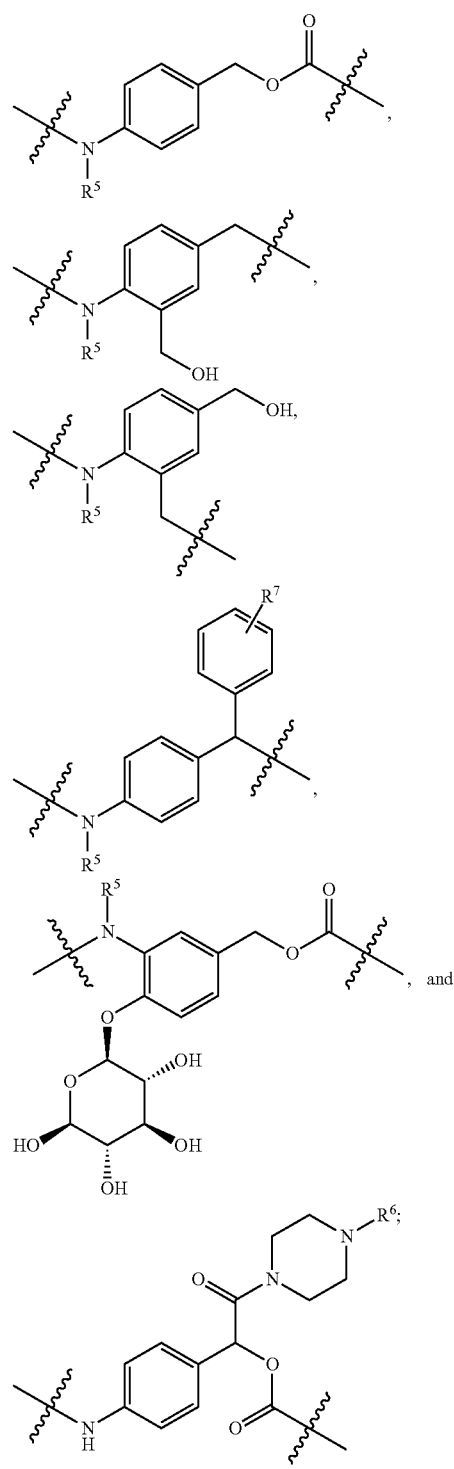

wherein

R⁵ represents H, tri((C₁-C₆)alkyl)silyl, or —C(O)((C₁-C₆)alkyl);

R⁶ represents H, (C₁-C₆)alkyl, or heterocycloalkyl;

R⁷ represents H, halo, —C(O)₂H, (C₁-C₆)alkoxy, di((C₁-C₆)alkyl)amino, —NO₂, —O(CH₂CH₂O)$_q$CH₃; and q is 1 or 2.

In certain such embodiments, R⁷ is H

In certain embodiments, the self-immolative linker is

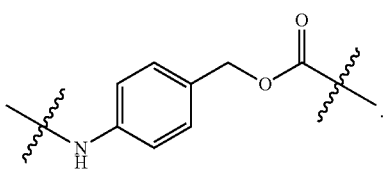 [SMILES: *Nc1ccc(COC(*)=O)cc1]

In alternative embodiments, the self-immolative linker is selected from

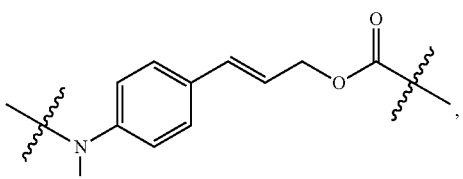,

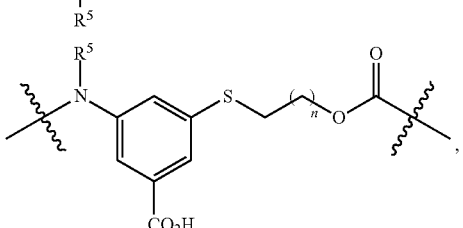,

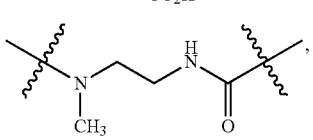,

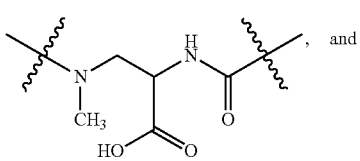, and

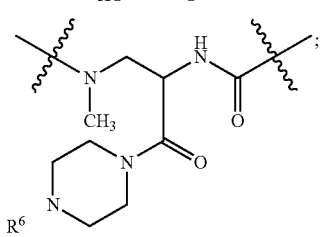;

wherein R⁵ represents H, tri((C₁-C₆)alkyl)silyl, or —C(O)((C₁-C₆)alkyl)

R⁶ represents H, (C₁-C₆)alkyl, or heterocycloalkyl; and n is 1 or 2.

In certain embodiments, the pharmacophore of the compound of formula (III) or formula (IV) is an antispasmodic agent, anesthetic agent, anti-inflammatory agent such as a nonsteroidal anti-inflammatory (NSAID) agent, anti-cancer therapeutic agent, calcium channel blocker, antibiotic agent, immunosuppressant, antiviral agent, anti-proliferative agent, antimicrobial agent, nerve-growth inducing agent, or smooth muscle relaxant.

In certain embodiments, the pharmacophore is an anti-cancer therapeutic agent.

In certain embodiments, the anti-cancer therapeutic agent is actinomycin-D, altretamine, aminoglutethimide, amsacrine, anastrozole, asparaginase, belactosin A, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, epoxomicin, estradiol, estramustine, etoposide, everolimus, exemestane, fellutamide B, filgrastim, fludarabine, fludrocortisone, 5-fluorouracil, floxuridine, fluoxymesterone, flutamide, gemcitabine, genistein, goserelin, hydroxyurea, idarubicin, ifosfamide, imatinib, interferon, irinotecan, ixabepilone, lenalidomide, letrozole, leucovorin, leuprolide, levamisole, lomustine, lonidamine, marizomib, mechlorethamine, medroxyprogesterone, megestrol, melphalan, mercaptopurine, mesna, metformin, methotrexate, methylprednisolone, mitomycin, mitotane, mitoxantrone, monomethyl auristatin, nilutamide, nocodazole, octreotide, omuralide, oxaliplatin, paclitaxel, pamidronate, pemetrexed, pentostatin, perifosine, plicamycin, pomalidomide, porfimer, prednisone, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, vinorelbine, MG-132, PSI, CEP-18770, MLN-2238, MLN-9708, NC-005, YU-101, LU-005, YU-102, NC-001, LU-001, NC-022, PR-957 (LMP7), CPSI (p5), 10 LMP2-sp-ek, BODIPY-NC-001, azido-NC-002, ONX-0912, PS-519, 125I-NIP-L3VS, NC-005-VS, or MV151.

In certain embodiments, the anti-cancer therapeutic agent is doxorubicin.

In certain embodiments of the compounds of formula (III) or formula (IV), D represents a pharmacophore selected from the group consisting of:

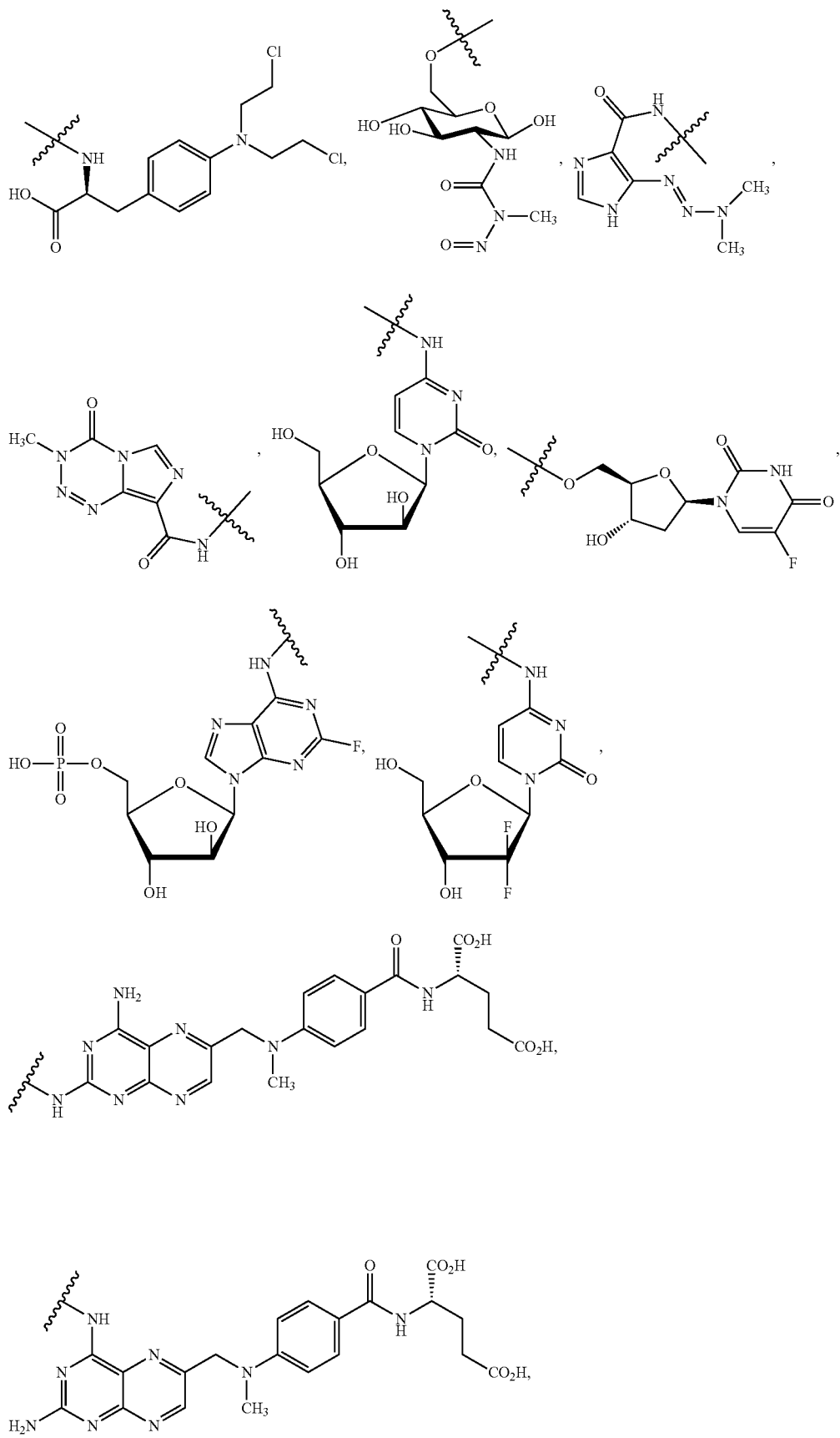

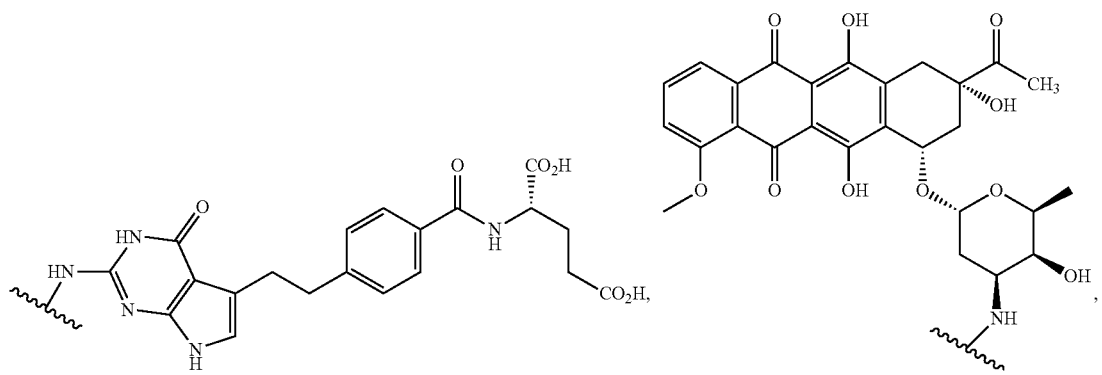
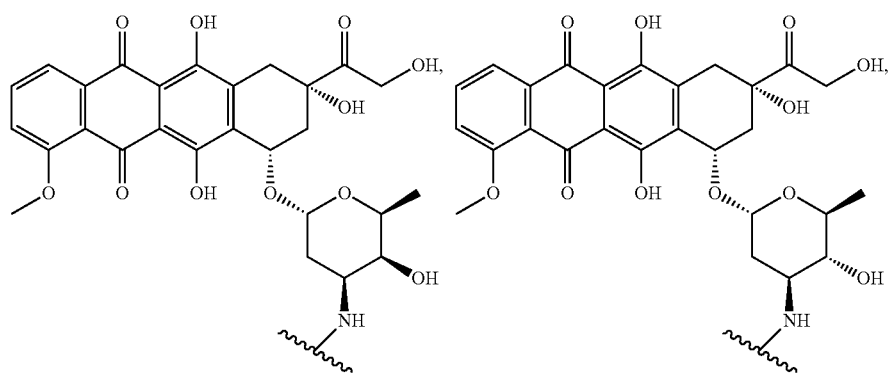
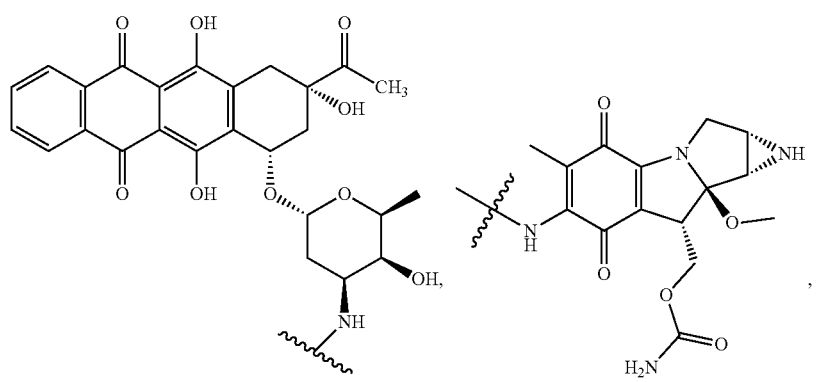
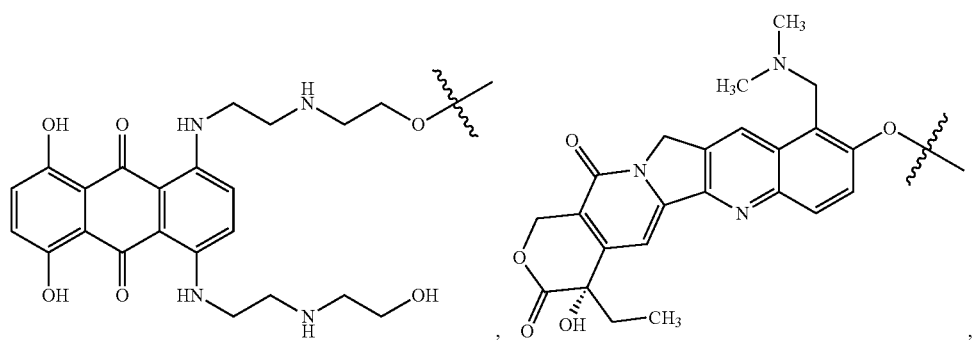

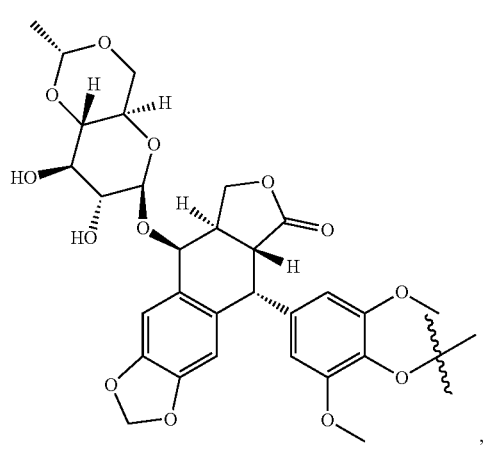
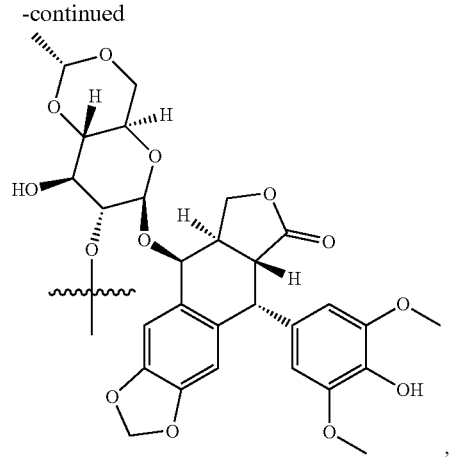
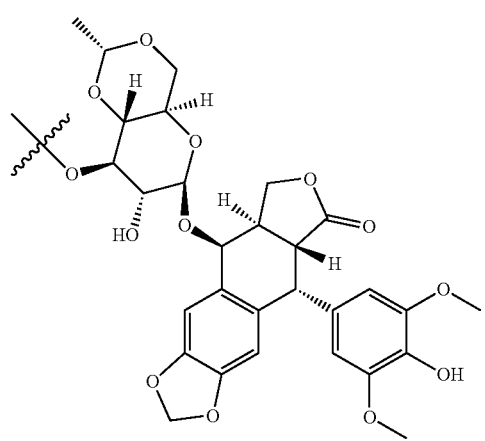
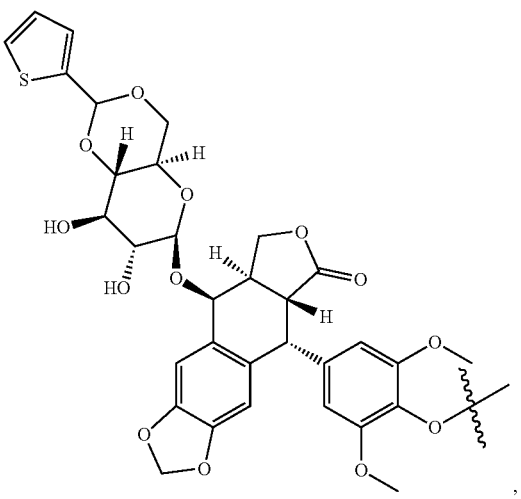
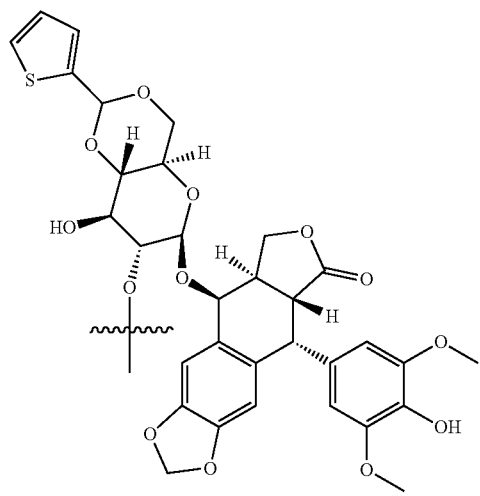
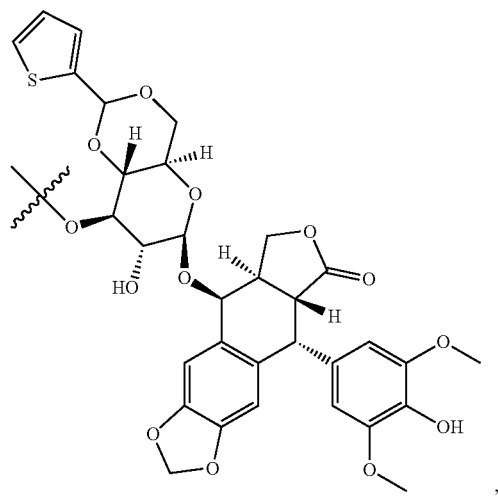

-continued
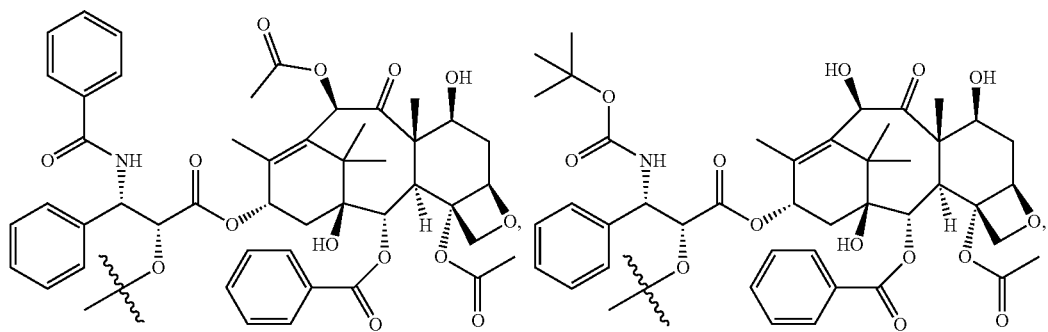
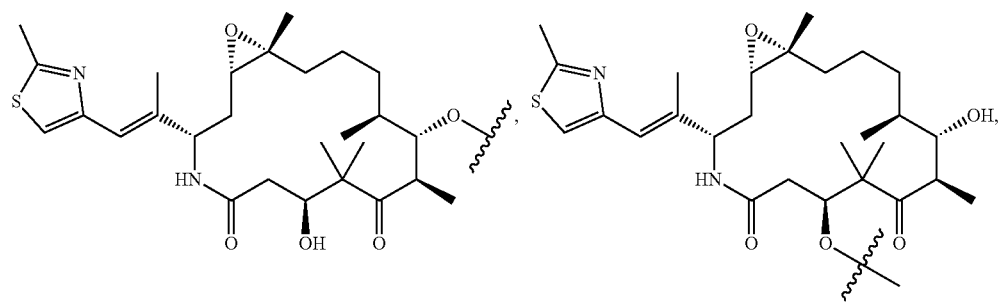
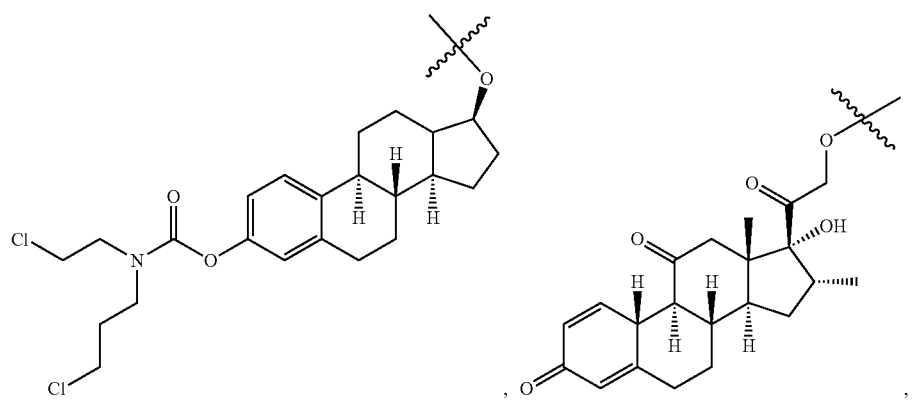
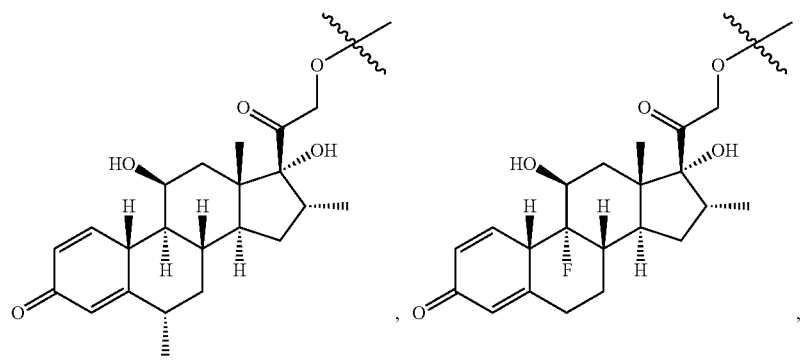

-continued
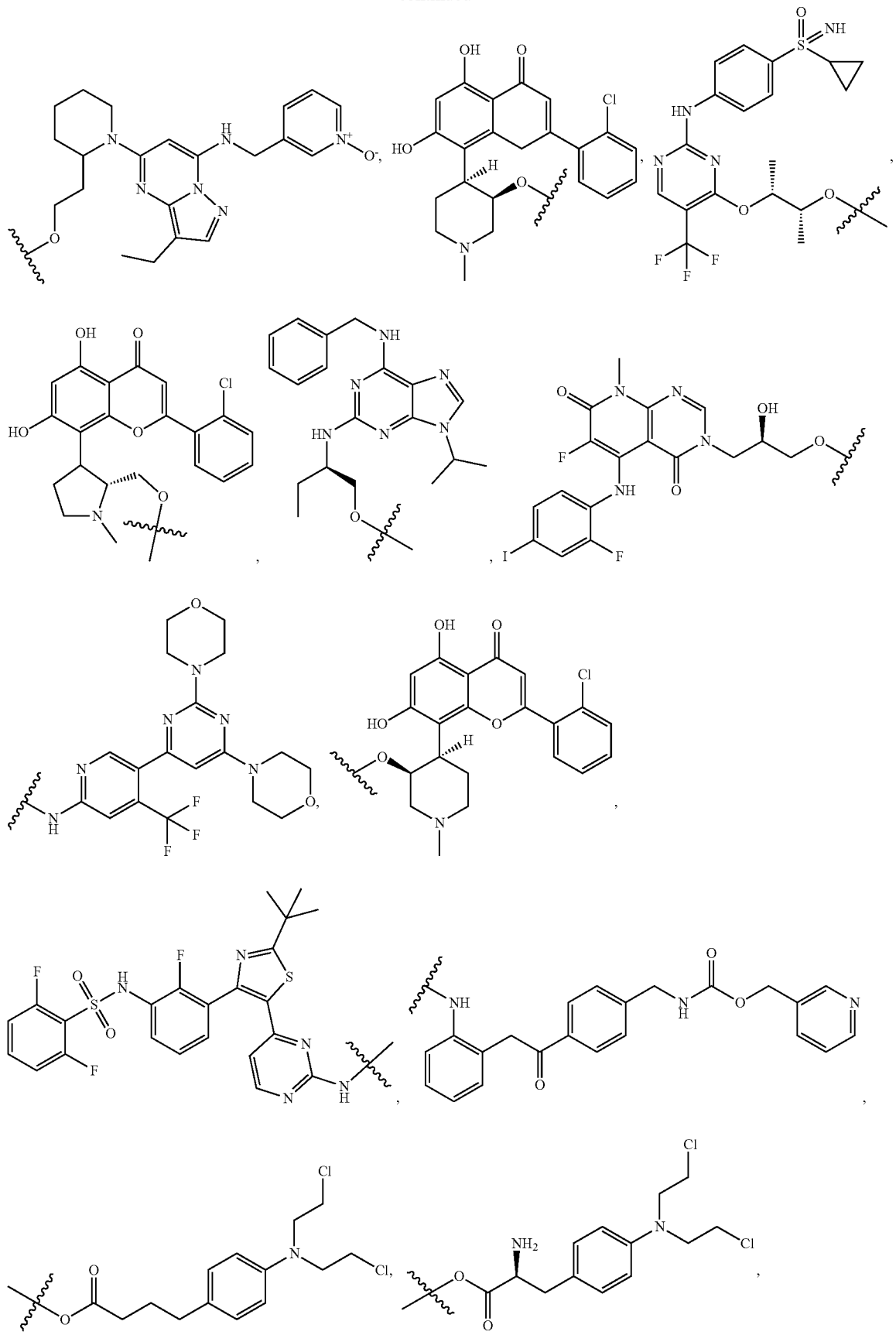

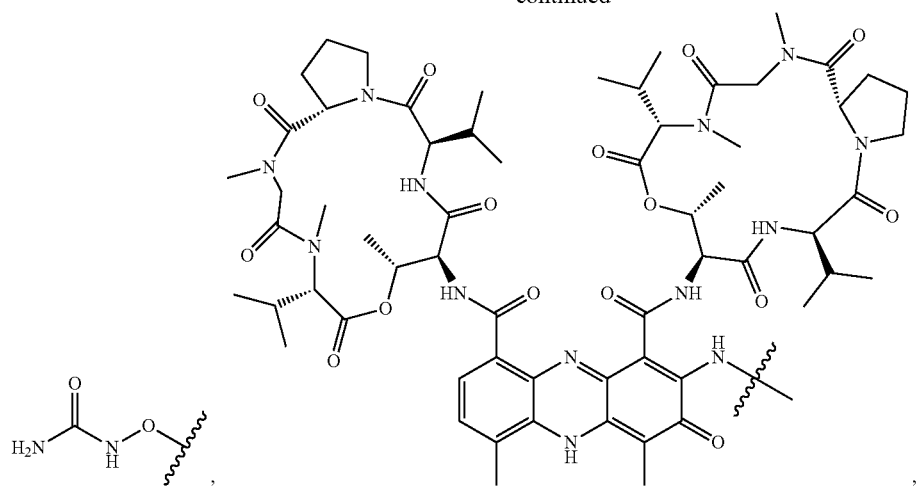
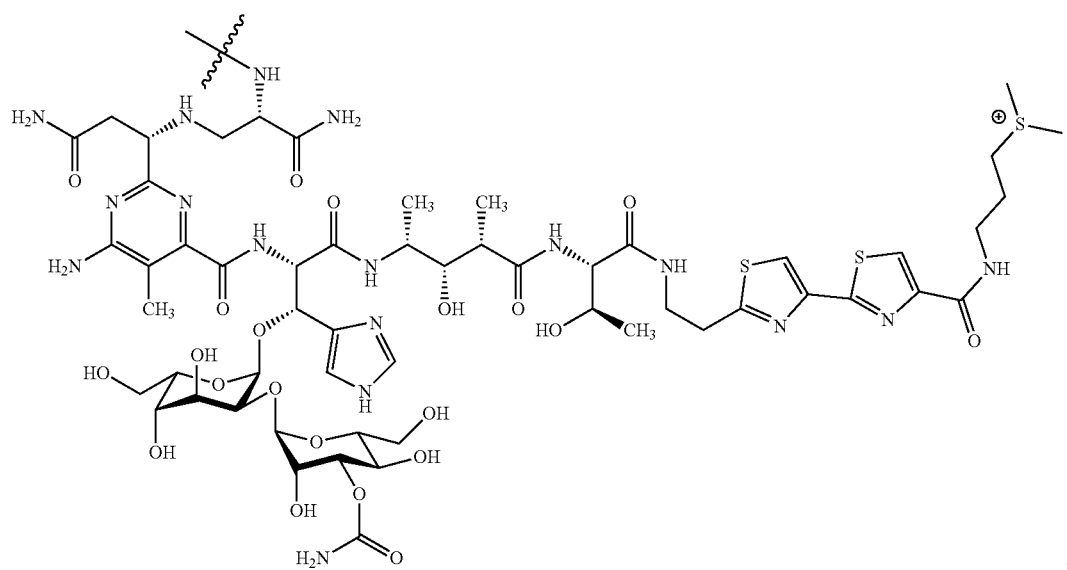
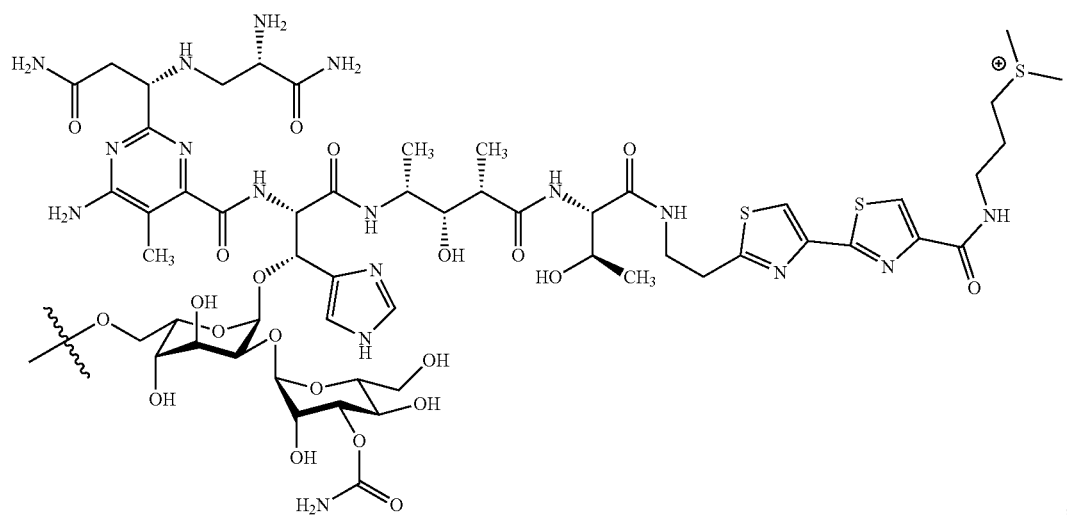
, and

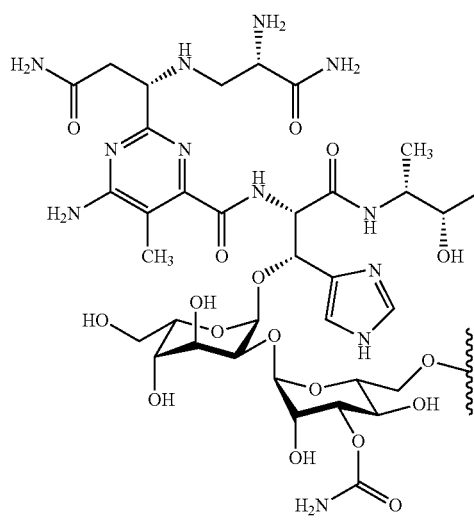
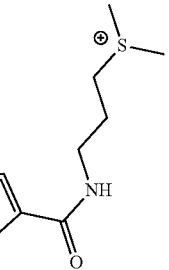
-continued
In alternative embodiments, D represents a pharmacophore selected from the group consisting of:
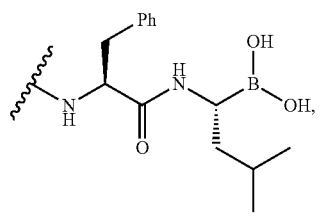
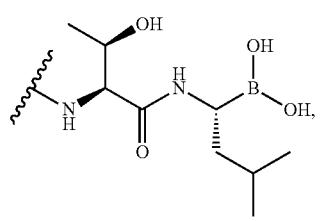
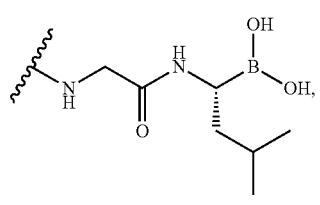
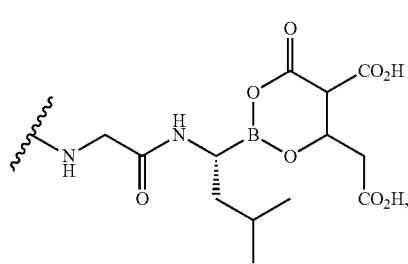
-continued
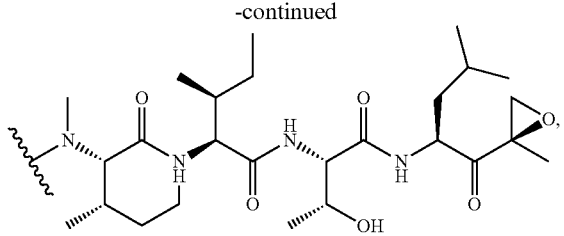
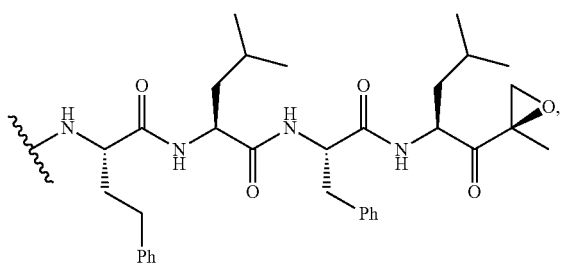
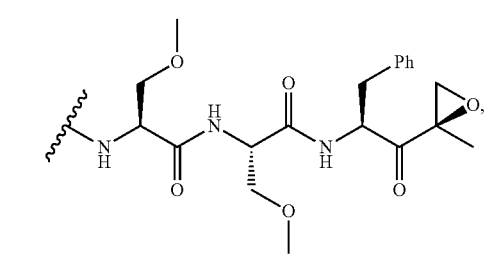
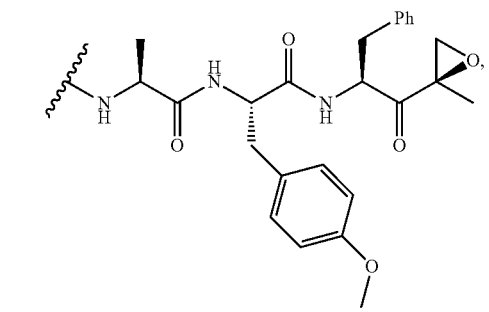

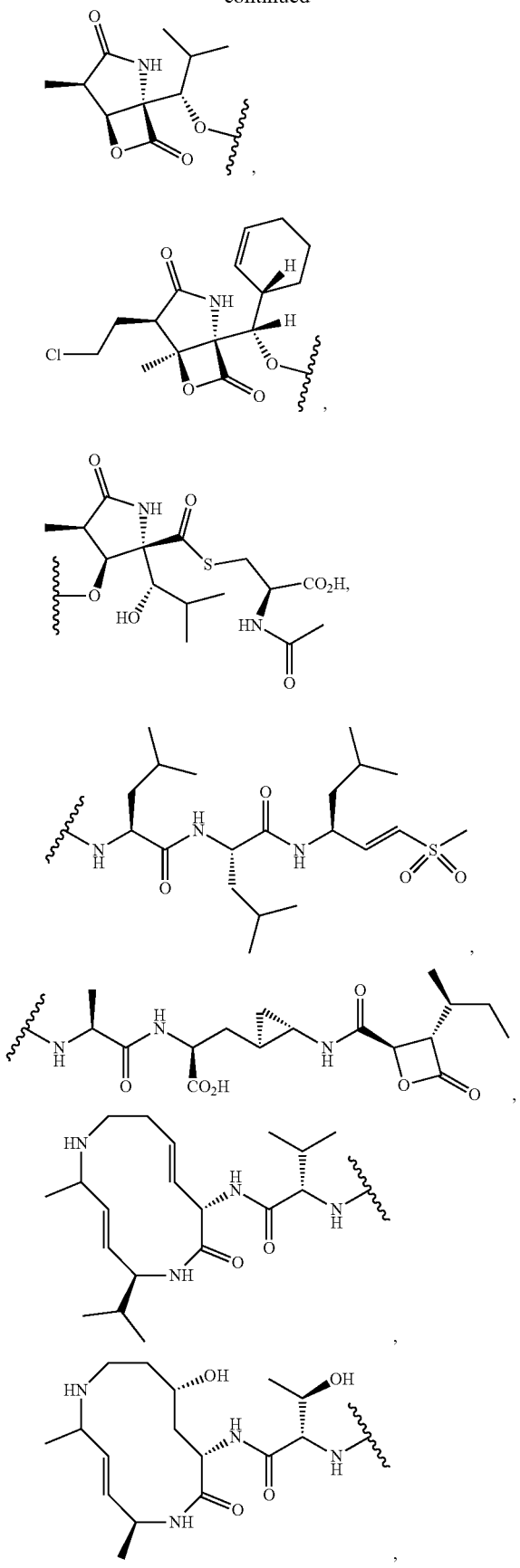
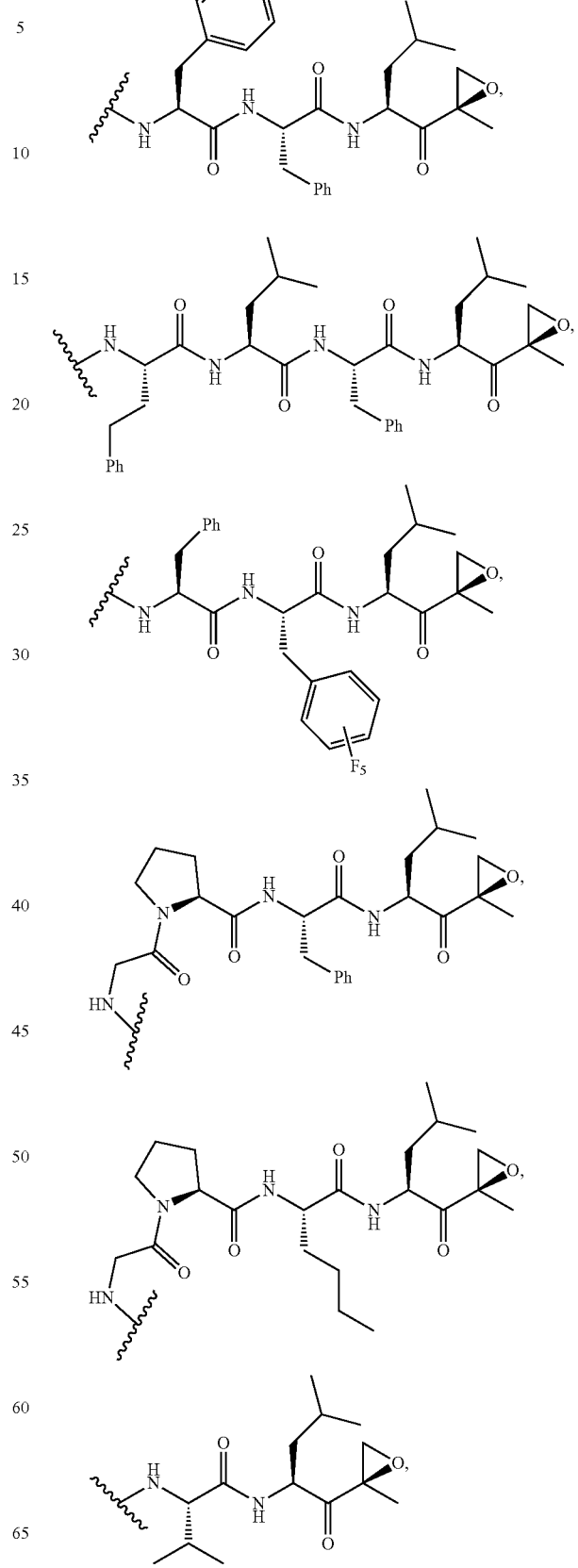

33
-continued
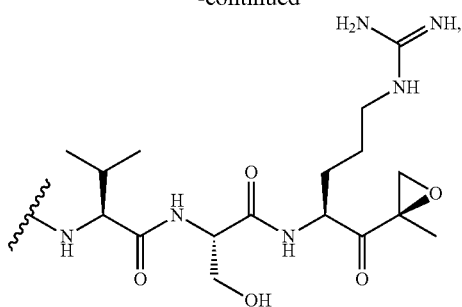
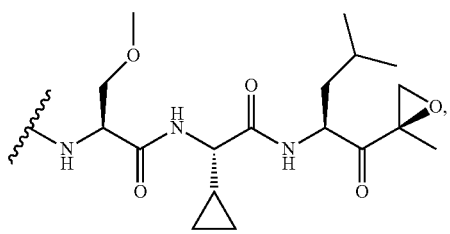
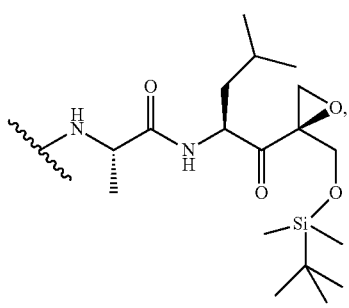
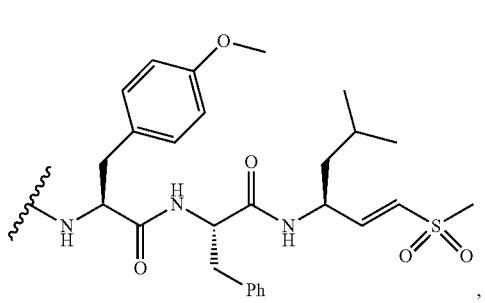
34
-continued
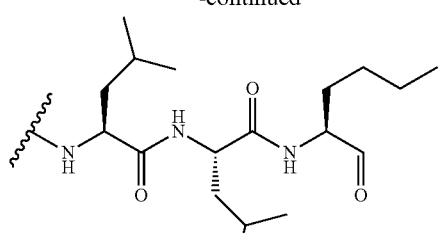
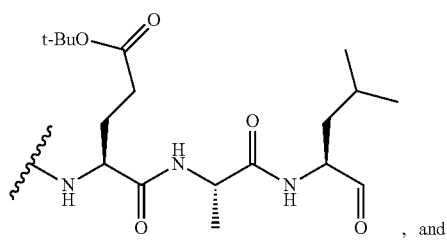
, and
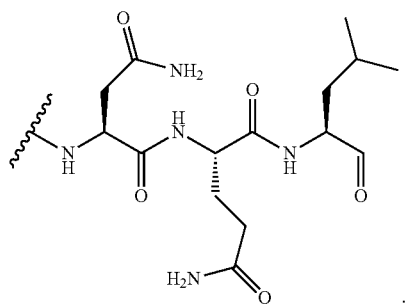
.

In certain embodiments, the compound of formula (III) is represented by:

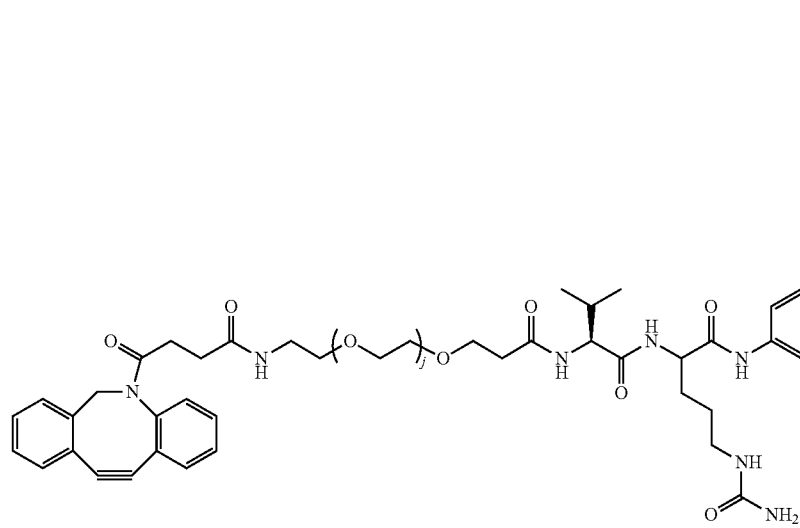

wherein j is an integer from 10-30.

In certain aspects, the invention relates to pharmaceutical compositions comprising a compound of the invention, or a pharmaceutically acceptable salt thereof, and a pharmaceutically acceptable carrier. Pharmaceutically acceptable carriers are described in detail below.

Methods of Treatment

In certain aspects, the invention relates to methods of expressing an azidosugar (e.g., an azido sialic acid; see Figures) on a surface of a cancer cell, comprising:
contacting a cancer cell with a compound;
wherein the compound is described herein, and comprises an optionally substituted N-((azido)acyl) 2-amino-2-deoxy-D-mannopyranosyl moiety; a trigger-responsive moiety that is cleaved by a trigger; and a self-immolative linker; wherein the self-immolative linker is covalently bonded to the mannopyranosyl moiety and to the trigger-responsive moiety;
thereby expressing the azidosugar on the surface of the cancer cell.

In certain aspects, the methods of expressing an azidosugar on a surface of a cancer cell, comprising contacting a cancer cell with a compound of formula (I); thereby expressing the azidosugar on the surface of the cancer cell.

In certain aspects, the invention provides methods of treating cancer, comprising administering to a subject in need thereof a therapeutically effective amount of a compound as described herein, wherein the compound comprises an optionally substituted N-((azido)acyl) 2-amino-2-deoxy-D-mannopyranosyl moiety; a trigger-responsive moiety that is cleaved by a trigger; and a self-immolative linker; wherein the self-immolative linker is covalently bonded to the mannopyranosyl moiety and to the trigger-responsive moiety.

In certain embodiments, such methods of treating cancer further comprise administering to the subject a therapeutically effective amount of a compound of formula (III).

In certain aspects, the invention provides methods of treating cancer, comprising administering to a subject in need thereof a therapeutically effective amount of a compound of formula (III).

In certain embodiments, the cancer is selected from Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenstrom Macroglobulinemia and Wilms Tumor.

In certain embodiments, the subject is a mammal, e.g., a human.

Definitions

The phrase "protecting group" as used herein means substituents which protect the reactive functional group from undesirable chemical reactions. Examples of such protecting groups include esters of carboxylic acids and boronic acids, ethers of alcohols, and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl, and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (Fmoc).

The term "amino-terminal protecting group" as used herein, refers to terminal amino protecting groups that are typically employed in organic synthesis, especially peptide synthesis. Any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl. See, for example, Gross and Mienhoffer, Eds., *The Peptides*, Academic Press: New York, 1981; Vol. 3, 3-88; and Green, T. W.; Wuts, P. G. M., *Protective Groups in Organic Synthesis,* 2nd ed, Wiley: New York, 1991. Preferred protecting groups include aryl-, aralkyl-, heteroaryl- and heteroarylalkyl-carbonyl and sulfonyl moieties.

As used herein the term "physiological conditions" refers to temperature, pH, ionic strength, viscosity, and like biochemical parameters which are compatible with a viable organism, and/or which typically exist intracellularly in a viable mammalian cell.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compounds of the invention. These salts can be prepared in situ during the final isolation and purification of the compound(s), or by separately reacting the purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. See, for example, Berge et al. (1977) "Pharmaceutical Salts", *J. Pharm. Sci.* 66:1-19.

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound of the invention. These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "self-eliminating linker" or "self-immolative linker" refers to a temporary extender, spacer, or placeholder unit attaching two or more molecules together by chemical bonds that are cleaved under defined conditions to release the two molecules. Examples of self-eliminating linkers include, but are not limited to, p-aminobenzyloxycarbonyl (PABC), 2,4-bis(hydroxymethyl)aniline, and 4-(phenylmethylene)aniline. The self-eliminating or self-immolative linker may be linear or branched, and may link two or more of the same molecules together, or may link two or more different molecules together. The self-eliminating or self-immolative linker may degrade, decompose, or fragment under, for example, physiological conditions, acidic conditions, basic conditions, or in the presence of specific chemical agents.

The pharmacophores used in the present invention are effective for the usual purposes for which the corresponding drugs are effective, and, in certain embodiments, have superior efficacy because of the ability, inherent in the azido-sugar targeting moiety, to transport the drug to the desired cell where it is of particular benefit.

The preferred therapeutic agents for use in the present embodiments are cytotoxic drugs, such as those which are used for cancer therapy. Such drugs include, in general, alkylating agents, antimetabolites, anti-tumor antibiotics such as anthracyclines, topoisomerase inhibitors, mitotic inhibitors, and corticosteroids.

One skilled in the art may make chemical modifications to the desired compound in order to make reactions of that compound more convenient for purposes of preparing conjugates of the invention.

In certain embodiments, D is a pharmacophore having a chemically reactive functional group by means of which the pharmacophore is bonded to the self-immolative linker. In certain instances, the functional group is selected from a primary amine, a secondary amine, hydroxyl, and sulfhydryl. In certain instances, the functional group is a primary amine or a secondary amine. In certain instances, the functional group is hydroxyl.

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties.

Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure. Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywherein the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)—$(CH_2)_m$—$R^1$, wherein m and $R^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R^1$, where m and $R_1$ are described below.

The terms "amine" and "amino" are art-recognized and refer to both unsubstituted and substituted amines, e.g., a moiety that can be represented by the formulae:

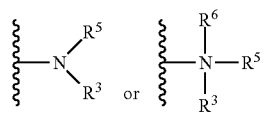

wherein $R^3$, $R^5$ and $R^6$ each independently represent a hydrogen, an alkyl, an alkenyl, —$(CH_2)_m$—$R^1$, or $R^3$ and $R^5$ taken together with the N atom to which they are attached complete a heterocycle having from 4 to 8 atoms in the ring structure; $R^1$ represents an alkenyl, aryl, cycloalkyl, a cycloalkenyl, a heterocyclyl, or a polycyclyl; and m is zero or an integer in the range of 1 to 8. In certain embodiments, only one of $R^3$ or $R^5$ can be a carbonyl, e.g., $R^3$, $R^5$, and the nitrogen together do not form an imide. In even more certain embodiments, $R^3$ and $R^5$ (and optionally $R^6$) each independently represent a hydrogen, an alkyl, an alkenyl, or —$(CH_2)_m$—$R^1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a conjugate acid with a $pK_a \geq 7.00$, i.e., the protonated forms of these functional groups have $pK_a$s relative to water above about 7.00.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings. In certain embodiments, aryl includes ($C_6$-$C_{10}$)aryl. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 6- to 10-membered rings, whose ring structures include one to four heteroatoms. In certain embodiments, heteroaryl includes ($C_2$-$C_9$)heteroaryl. Heteroaryl groups include, for example, pyrrole, furan, thiophene, imidazole, oxazole, thiazole, triazole, pyrazole, pyridine, pyrazine, pyridazine and pyrimidine, and the like.

The term "aralkyl" is art-recognized and refers to an alkyl group substituted with an aryl group.

The term "heteroaralkyl" is art-recognized and refers to an alkyl group substituted with a heteroaryl group.

The term "heteroatom" is art-recognized and refers to an atom of any element other than carbon or hydrogen. Illustrative heteroatoms include boron, nitrogen, oxygen, phosphorus, sulfur and selenium.

The terms "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. In certain embodiments, heterocyclyl includes ($C_2$-$C_9$)heterocyclyl. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, and the like.

The term "carbonyl" is art-recognized and includes such moieties as can be represented by the formula:

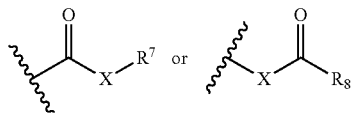

wherein X is a bond or represents an oxygen or a sulfur, and R$^7$ represents a hydrogen, an alkyl, an alkenyl, —(CH$_2$)$_m$—R$^1$ or a pharmaceutically acceptable salt, R$^8$ represents a hydrogen, an alkyl, an alkenyl or —(CH$_2$)$_m$—R$^1$, where m and R$^1$ are as defined above. Where X is an oxygen and R$^7$ or R$^8$ is not hydrogen, the formula represents an "ester." Where X is an oxygen, and R$^7$ is as defined above, the moiety is referred to herein as a carboxyl group, and particularly when R$^7$ is a hydrogen, the formula represents a "carboxylic acid". Where X is an oxygen, and R$^8$ is a hydrogen, the formula represents a "formate." In general, where the oxygen atom of the above formula is replaced by a sulfur, the formula represents a "thiocarbonyl" group. Where X is a sulfur and R$^7$ or R$^8$ is not hydrogen, the formula represents a "thioester" group. Where X is a sulfur and R$^7$ is a hydrogen, the formula represents a "thiocarboxylic acid" group. Where X is a sulfur and R$^8$ is a hydrogen, the formula represents a "thioformate" group. On the other hand, where X is a bond, and R$^7$ is not hydrogen, the above formula represents a "ketone" group. Where X is a bond, and R$^7$ is a hydrogen, the above formula represents an "aldehyde" group.

The term "thioxamide," as used herein, refers to a moiety that can be represented by the formula:

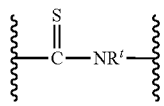

in which R$^t$ is selected from the group consisting of the group consisting of hydrogen, alkyl, cycloalkyl, aralkyl, or aryl, preferably hydrogen or alkyl. Moreover, "thioxamide-derived" compounds or "thioxamide analogues" refer to compounds in which one or more amide groups have been replaced by one or more corresponding thioxamide groups. Thioxamides are also referred to in the art as "thioamides."

The term "amido" is art recognized as an amino-substituted carbonyl and includes a moiety that may be represented by the general formula:

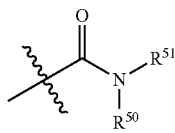

wherein R$^{50}$ and R$^{51}$ are as defined above. Certain embodiments of the amide in the present invention will not include imides which may be unstable.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —NO$_2$; the term "halogen" designates —F, —Cl, —Br, or —I; the term "sulfhydryl" means —SH; the term "hydroxyl" means —OH; the term "sulfonyl" means —SO$_2$—; the term "azido" means —N$_3$; the term "cyano" means —CN; the term "isocyanato" means —NCO; the term "thiocyanato" means —SCN; the term "isothiocyanato" means —NCS; and the term "cyanato" means —OCN.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "sulfamoyl" is art-recognized and includes a moiety that can be represented by the formula:

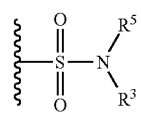

in which R$^3$ and R$^5$ are as defined above.
The term "sulfate" is art recognized and includes a moiety that can be represented by the formula:

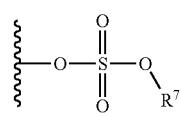

in which R$^7$ is as defined above.
The term "sulfonamide" is art recognized and includes a moiety that can be represented by the formula:

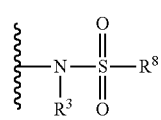

in which R$^3$ and R$^8$ are as defined above.

The term "sulfonate" is art-recognized and includes a moiety that can be represented by the formula:

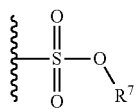

in which $R^7$ is an electron pair, hydrogen, alkyl, cycloalkyl, or aryl.

The terms "sulfoxido" or "sulfinyl", as used herein, refers to a moiety that can be represented by the formula:

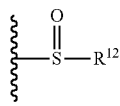

in which $R^{12}$ is selected from the group consisting of the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, *Handbook of Chemistry and Physics,* 67th ed., 1986-87, inside cover.

Pharmaceutical Compositions

Also provided are pharmaceutical compositions comprising a compound of the invention (e.g., a compound of any one of formulae I, II, III, or IV), or a pharmaceutically acceptable salt thereof, and a pharmaceutically acceptable excipient or carrier. Also provided is a method for making such pharmaceutical compositions. The method comprises placing a compound of the invention, or a pharmaceutically acceptable salt thereof, in a pharmaceutically acceptable excipient or carrier.

Compounds of the invention and pharmaceutical compositions of the invention are useful for the treatment of cancer in a subject. In certain embodiments, a therapeutically effective amount of a compound of the invention, or a pharmaceutically acceptable salt thereof, is administered to a subject in need thereof, thereby treating cancer.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In certain embodiments a subject is a human.

In certain embodiments, the subject is a human.

As used herein, "administering" has its usual meaning and encompasses administering by any suitable route of administration, including, without limitation, intravenous, intramuscular, intraperitoneal, intrathecal, intraocular (e.g., intravitreal), subcutaneous, direct injection (for example, into a tumor), mucosal, inhalation, oral, and topical.

In one embodiment, the administration is intravenous.

In one embodiment, the administration is oral.

As used herein, the phrase "effective amount" refers to any amount that is sufficient to achieve a desired biological effect.

Compounds of the invention can be combined with other therapeutic agents, or may be used in combination with other compounds of the invention. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include antibiotics, anti-viral agents, anti-inflammatory agents, immunosuppressive agents, antiarrhythmic agents, beta blockers, analgesics, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is sometimes preferred that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a compound of the invention may typically be from 0.1 mg/kg/day to 20 mg/kg/day.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound of the invention can be administered to a subject by any mode that delivers the compound of the invention to the desired location or surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, inhalation, and topical.

For intravenous and other parenteral routes of administration, the compound can be formulated as a lyophilized preparation with desoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., Pharm Res 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong, et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Example 1. Synthesis of Ac$_4$ManAz Derivatives

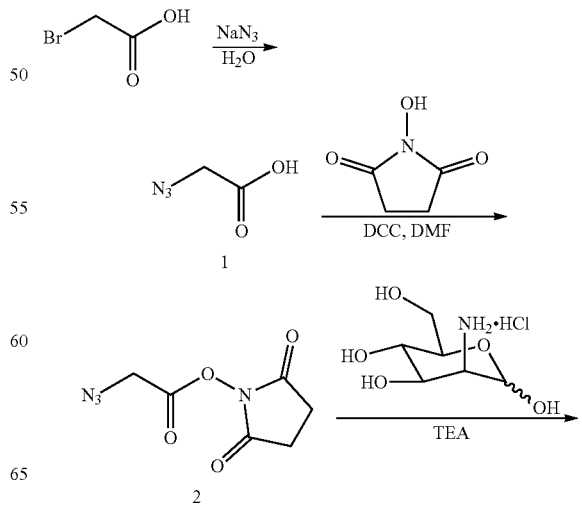

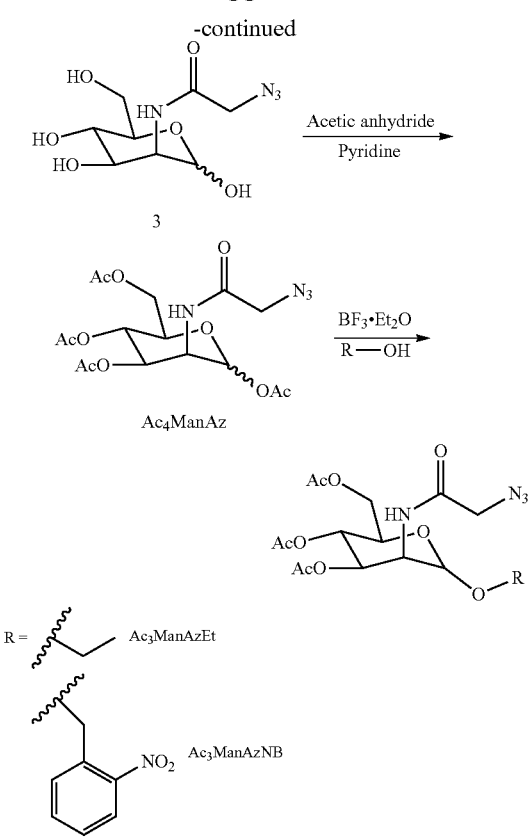

Synthesis of 2-azidoacetic acid (1). Bromoacetic acid (2.78 g, 20 mmol) was dissolved in DI water (30 mL), followed by the addition of sodium azide (2.60 g, 40 mmol). The mixture was stirred at room temperature for 24 h. The resulting solution was adjusted to pH=1 using hydrogen chloride solution, and then extracted with diethyl ether for three times (100 mL×3). The organic phase was collected, dried over anhydrous sodium sulfate, and concentrated to get colorless oil (80% yield, 1.62 g).

Synthesis of N-(2-azidoacetyl) succinimide (2). N,N'-Dicyclohexylcarbodiimide (DCC, 2.06 g, 10 mmol) and 1 (1.01 g, 10 mmol) were dissolved in anhydrous DMF, followed by the addition of N-hydroxysuccinimide (1.15 g, 10 mmol). The mixture was stirred at room temperature for 24 h. After removal of the precipitate, the solvent was removed to yield a yellow solid. The crude product was recrystallized from dichloromethane/hexane to obtain a white solid (70% yield, 1.39 g). $^1$H NMR (CDCl$_3$, 500 MHz): δ 4.25 (s, 2H, N$_3$CH$_2$), 2.88 (s, 4H, CH$_2$CH$_2$). $^{13}$C NMR (CDCl$_3$, 500 MHz): 168.7, 164.4, 48.2, 25.8. LRMS (ESI) m/z: calculated for C$_6$H$_7$N$_4$O$_4$ [M+H]$^+$ 199.0, found 199.0.

Synthesis of Ac$_4$ManAz. D-Mannosamine hydrochloride (539 mg, 2.5 mmol) and triethylamine (253 mg, 2.5 mmol) were dissolved in methanol (40 mL), followed by the addition of 2 (545 mg, 2.75 mmol). The mixture was stirred at room temperature for 24 h. Solvent was removed under reduced pressure and the residue was redissolved in pyridine. Acetic anhydride (10 mL) was added and the reaction mixture was stirred at room temperature for another 24 h. After removal of the solvent, the crude product was purified by silica gel column chromatography using ethyl acetate/hexane (1/1, v/v) as the eluent to yield a white solid (45% yield, 484.5 mg). LRMS (ESI) m/z: calculated for C$_{16}$H$_{22}$N$_4$O$_{10}$Na [M+Na]$^+$ 453.1, found 453.1.

Synthesis of Ac$_3$ManAzEt. Ac$_4$ManAz (43 mg, 0.1 mmol) and anhydrous ethanol (14 mg, 0.3 mmol) were dissolved in dry DCM (1.5 mL) and purged with nitrogen for 10 min. Boron trifluoride etherate (71 mg, 0.5 mmol) was added through a syringe. The mixture was stirred under dark for overnight at room temperature. DCM (30 mL) was then added and the solution was washed with saturated sodium bicarbonate solution twice (10 mL×2) and DI water twice (10 mL×2), respectively. The organic phase was collected, dried over anhydrous sodium sulfate, and concentrated to yield yellow oil. The crude product was purified by silica gel column chromatography using ethyl acetate/hexane (1/1, v/v) as the eluent to yield a white solid (30% yield, 12.5 mg). LRMS (ESI) m/z: calculated for C$_{16}$H$_{25}$N$_4$O$_9$ [M+H]$^+$ 417.2, found 417.2.

Synthesis of Ac$_3$ManAzNB. Ac$_4$ManAz (43 mg, 0.1 mmol) and 2-nitrobenzylalcohol (30 mg, 0.2 mmol) were dissolved in dry DCM (1.5 mL) and purged with nitrogen for 10 min. Borotrifluoride etherate (70.9 mg, 0.5 mmol) was added through a syringe. The mixture was stirred overnight at room temperature under nitrogen atmosphere. DCM (30 mL) was then added and the solution was washed with saturated sodium bicarbonate solution twice (10 mL×2) and DI water twice (10 mL×2), respectively. The organic phase was collected, dried over anhydrous sodium sulfate and concentrated to yield brown oil. The crude product was purified by silica gel column chromatography using ethyl acetate/hexane (1/1, v/v) as the eluent to yield a pale red solid (25% yield, 13.0 mg). LRMS (ESI) m/z: calculated for C$_{211}$H$_{25}$N$_5$O$_{11}$Na [M+Na]$^+$ 546.2, found 546.2.

UV induced degradation of Ac$_3$ManAzNB. Ac$_3$ManAzNB (1 mg) was dissolved in anhydrous DCM (1.0 mL) and stirred at room temperature under UV irradiation. The intensity of UV irradiation was set at 20 mW/cm$^2$. 20 μL of reaction solution was taken out and diluted to 600 μL prior to HPLC measurements at selected time points (0, 5, 15, and 30 min). After HPLC showed the complete degradation of the starting material, ESI mass spectrum of the reaction solution was measured to confirm the degraded products.

Scheme S2. Synthetic route of Ac$_3$ManAzHB

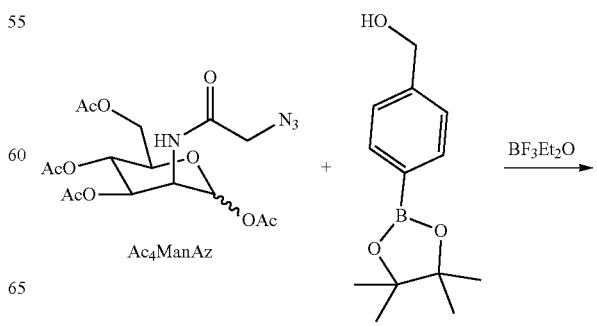

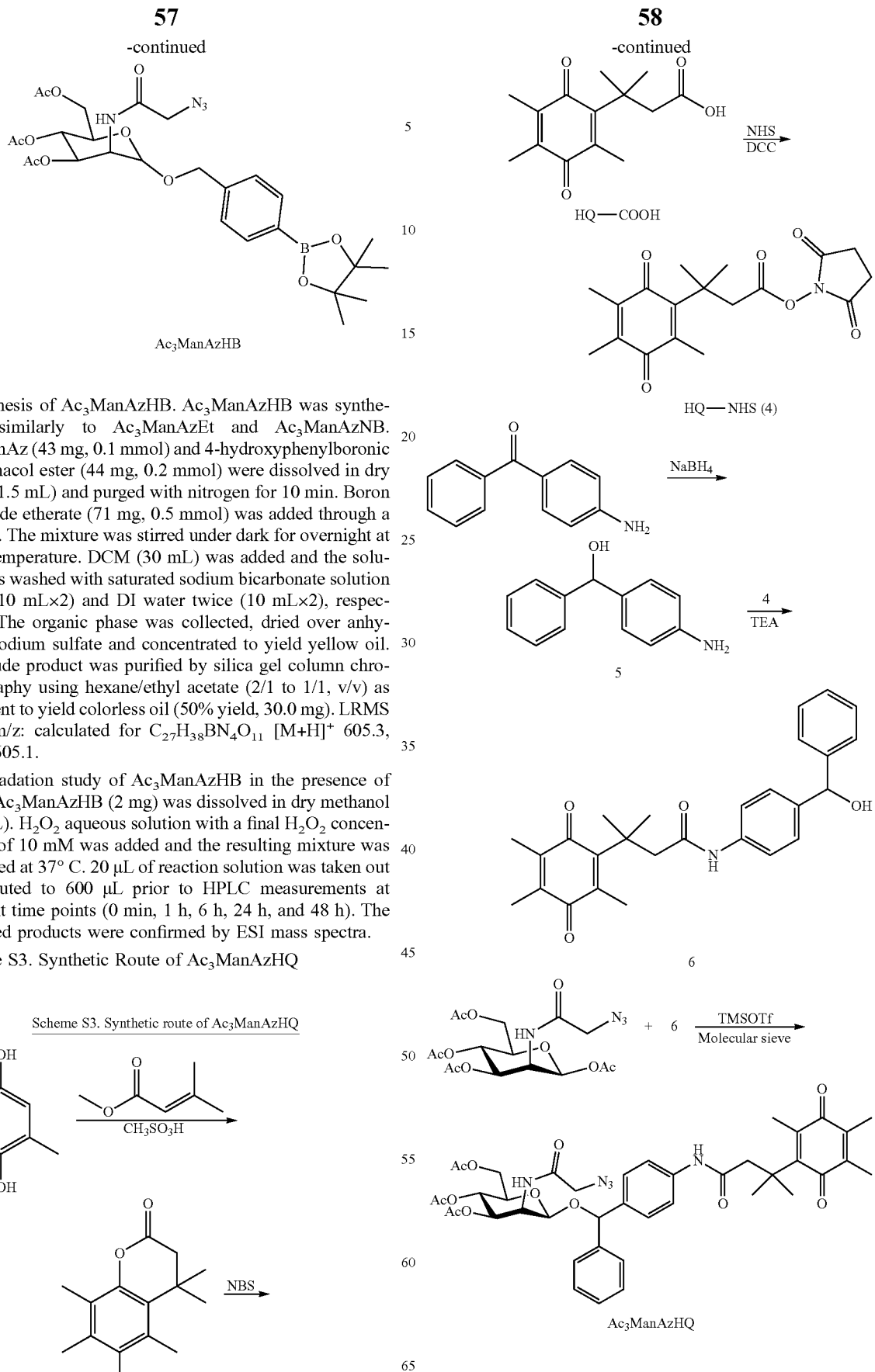

Ac₃ManAzHB

Synthesis of Ac₃ManAzHB. Ac₃ManAzHB was synthesized similarly to Ac₃ManAzEt and Ac₃ManAzNB. Ac₄ManAz (43 mg, 0.1 mmol) and 4-hydroxyphenylboronic acid pinacol ester (44 mg, 0.2 mmol) were dissolved in dry DCM (1.5 mL) and purged with nitrogen for 10 min. Boron trifluoride etherate (71 mg, 0.5 mmol) was added through a syringe. The mixture was stirred under dark for overnight at room temperature. DCM (30 mL) was added and the solution was washed with saturated sodium bicarbonate solution twice (10 mL×2) and DI water twice (10 mL×2), respectively. The organic phase was collected, dried over anhydrous sodium sulfate and concentrated to yield yellow oil. The crude product was purified by silica gel column chromatography using hexane/ethyl acetate (2/1 to 1/1, v/v) as the eluent to yield colorless oil (50% yield, 30.0 mg). LRMS (ESI) m/z: calculated for $C_{27}H_{38}BN_4O_{11}$ $[M+H]^+$ 605.3, found 605.1.

Degradation study of Ac₃ManAzHB in the presence of H₂O₂. Ac₃ManAzHB (2 mg) was dissolved in dry methanol (1.0 mL). H₂O₂ aqueous solution with a final H₂O₂ concentration of 10 mM was added and the resulting mixture was incubated at 37° C. 20 µL of reaction solution was taken out and diluted to 600 µL prior to HPLC measurements at different time points (0 min, 1 h, 6 h, 24 h, and 48 h). The degraded products were confirmed by ESI mass spectra.

Scheme S3. Synthetic Route of Ac₃ManAzHQ

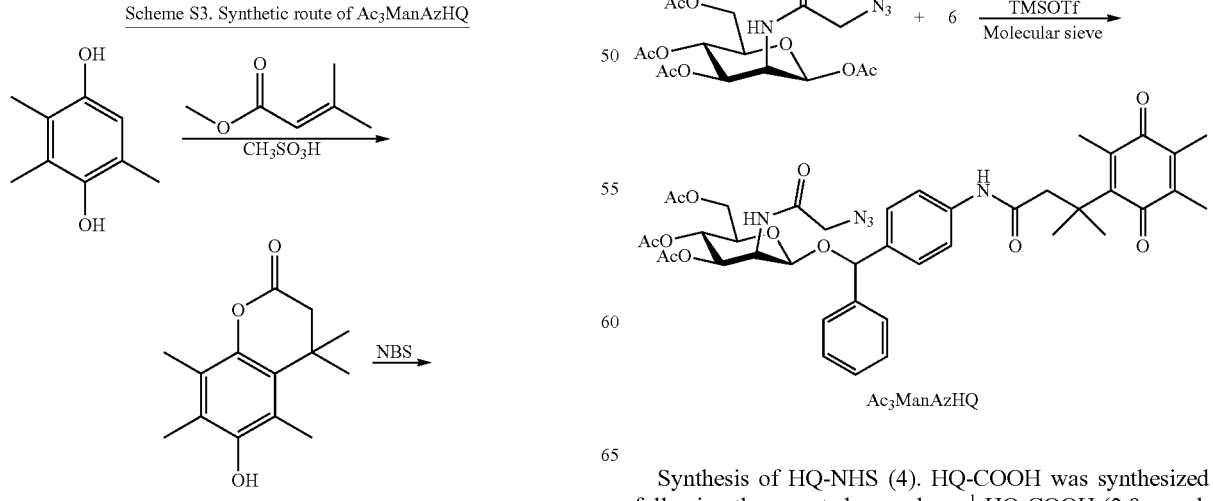

Synthesis of HQ-NHS (4). HQ-COOH was synthesized following the reported procedures.[1] HQ-COOH (2.0 mmol, 501 mg), N-hydroxylsuccinimide (NHS, 2.1 mmol, 242 mg) and trimethylamine (2.0 mmol, 202 mg) were dissolved in anhydrous DMF (30 mL), followed by the addition of N,N'-dicyclohexylcarbodiimide (DCC, 2.1 mmol, 433 mg). The mixture was stirred at room temperature for 24 h. The precipitate was filtered off and the solvent was removed under reduced pressure. The crude product was purified by silica gel column chromatography using hexane/ethyl acetate (3/1, v/v) as the eluent to yield a yellow solid (75% yield). LRMS (ESI) m/z: calculated for $C_{18}H_{22}NO_6$ [M+H]$^+$ 348.1, found 348.1.

Synthesis of compound 5. 4-Aminobenzophenone (5 mmol, 985 mg) was dissolved in dry methanol (50 mL), followed by addition of $NaBH_4$ (10 mmol, 378 mg). The mixture was stirred at room temperature for 24 h. After removal of the solvent, the crude product was purified by silica gel column chromatography using hexane/ethyl acetate (6/1 to 3/1) as the eluent. Compound 5 was obtained as a light yellow solid (80% yield). LRMS (ESI) m/z: calculated for $C_{13}H_{14}NO$ [M+H]$^+$ 200.1, found 200.1.

Synthesis of Compound 6. Compound 4 (1.0 mmol, 347 mg) and 5 (1.0 mmol, 199 mg) were dissolved in anhydrous DMF (40 mL), followed by the addition of triethylamine (1.0 mmol, 101 mg). The mixture was stirred at 50° C. for 48 h. The solvent was then removed under reduced pressure and the crude product was purified by silica gel column chromatography using hexane/ethyl acetate (1/1) as the eluent. Compound 6 was obtained as a light yellow solid. LRMS (ESI) m/z: calculated for $C_{27}H_{30}NO_4$ [M+H]$^+$ 432.2, found 432.2.

Synthesis of $Ac_3ManAzHQ$. $Ac_4ManAz$ (0.2 mmol, 86 mg) was dissolved in anhydrous THF, followed by the addition of TMSOTf (0.25 mmol) in THF. The mixture was stirred at room temperature for 48 h. Molecular sieves (3 Å) were added and the mixture was further stirred for 6 h at room temperature. Compound 6 was then added, and the reaction solution was further stirred at room temperature for 24 h. After removal of the solvent, the crude product was purified by silica gel column chromatography using ethyl acetate to ethyl acetate/methanol (95/5, v/v) as the eluent. A light yellow solid was obtained (35% yield). LRMS (ESI) m/z: calculated for $C_{41}H_{47}N_5O_{12}Na$ [M+Na]$^+$ 824.3, found 824.3.

$Na_2S_2O_4$ induced degradation of $Ac_3ManAzHQ$. $Ac_3ManAzHQ$ (1 mg) was dissolved in methanol/$H_2O$ (9/1, v/v, 1 mL), followed by the addition of $Na_2S_2O_4$ (1 mg). The mixture was stirred at 37° C. (100 rpm). At selected time points, 20 µL of solution was injected into HPLC to monitor the degradation process of $Ac_3ManAzHQ$. After HPLC showed the complete degradation, ESI mass spectra were measured to confirm the degraded products.

Example 2. Investigation of $Ac_4ManAz$ Derivatives in Cell-Labeling

Figure 2:
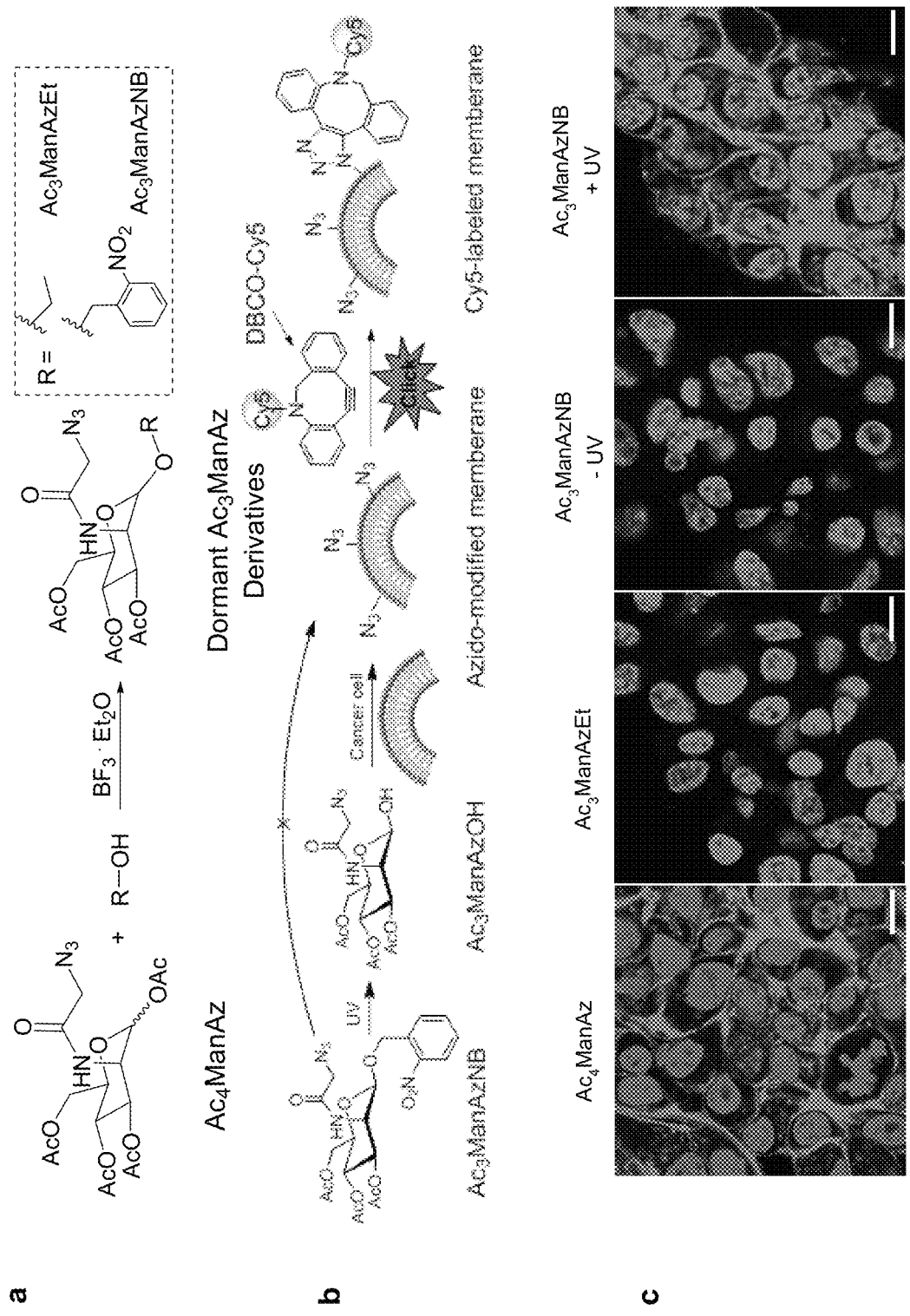
FIG. 2 consists of panels a-e. Panel (a) shows the synthetic route of $Ac_3ManAz$ derivatives including $Ac_3ManAzEt$ and $Ac_3ManAzNB$. Panel (b) is a scheme depicting the UV irradiation-activated metabolic labeling of $Ac_3ManAzNB$ and subsequent detection of azido groups by DBCO-Cy5 via copper-free Click chemistry. Panel (c) contains CLSM images of LS174T colon cancer cells after incubation with 50 μM $Ac_4ManAz$, $Ac_3ManAzEt$, $Ac_3ManAzNB$-UV, or $Ac_3ManAzNB$+UV for 72 h and followed by further incubation with 50 μM DBCO-Cy5 for 1 h. UV irradiation with an intensity of 10 mW/cm$^2$ was applied for 10 min. The cell nucleus was stained with DAPI. Scale bar represents 10 μm. Panel (d) is a graph depicting flow cytometry analysis of LS174T cells for different groups: $Ac_4ManAz$, $Ac_3ManAzEt$, $Ac_3ManAzNB$-UV, $Ac_3ManAzNB$+UV, and PBS. Panel (e) is a western Blot analysis of LS174T cells treated with 50 μM $Ac_4ManAz$, $Ac_3ManAzEt$, $Ac_3ManAzNB$-UV, and $Ac_3ManAzNB$+UV, respectively for 72 h.

To demonstrate whether modifying the C1 site of $Ac_4ManAz$ by forming a glycosidic (ether) bond could block the metabolic labeling process, we first synthesized $Ac_3ManAzEt$, the corresponding ethyl glycoside (FIG. 2, panel a), and investigated its cell labeling capability in vitro. LS174T colon cancer cells were incubated with $Ac_4ManAz$, $Ac_3ManAzEt$, and PBS respectively for three days, and the potentially expressed azido groups were detected by DBCO-Cy5 via Click reaction. As shown in FIG. 2, panel c, cells treated with $Ac_4ManAz$ showed strong Cy5 fluorescence on the cell surface, indicating the successful expression of azido groups. In comparison, LS174T cells treated with $Ac_3ManAzEt$ or PBS showed negligible Cy5 fluorescence on the cell surface, indicating that $Ac_3ManAzEt$ failed to introduce azido groups onto cell surface via metabolic labeling process. Flow cytometry analysis of LS174T cells treated with $Ac_4ManAz$ also showed significantly enhanced Cy5 fluorescence than cells treated with $Ac_3ManAzEt$ or PBS (FIG. 2, panel d). To confirm that azido groups were expressed on the cell surface in the form of glycoproteins, western blot analyses of LS174T cells treated with $Ac_4ManAz$, $Ac_3ManAzEt$ and PBS, respectively were performed. The azido-glycoproteins were biotinylated by incubating with phosphine-$PEG_3$-biotin, and thus could be easily detected. The results were shown in FIG. 2, panel e, which showed a series of protein bands in $Ac_4ManAz$ group but only two endogenous biotinylated proteins of LS174T cells in $Ac_3ManAzEt$ and PBS groups. These data demonstrated that $Ac_3ManAzEt$ failed to metabolically label cancer cells with azido groups.

To further demonstrate that the glycosidic bond at the C1 site was responsible for the blocking of the metabolic labeling process, and that cleavage of this bond to expose 1-OH could reactivate the labeling process, UV-cleavable $Ac_3ManAzNB$ was synthesized (FIG. 2, panel b) and its controlled labeling capability was investigated in vitro. LS174T cells were incubated with $Ac_3ManAzNB$ with or without UV treatment (10 min, 10 mW/cm$^2$) for three days, and cell-surface azido groups were detected by DBCO-Cy5. Without UV irradiation, LS174T cells treated with $Ac_3ManAzNB$ showed negligible Cy5 fluorescence on cell surface, further demonstrating the blocking effect of chemical modification at C1 site (FIG. 2, panel c). In the presence of UV irradiation, however, LS174T cells showed strong Cy5 fluorescence, due to the degradation of $Ac_3ManAzNB$ into $Ac_3ManAzOH$ which reactivated the labeling process. Flow cytometry analyses also showed significantly enhanced Cy5 fluorescence in LS174T cells treated with $Ac_3ManAzNB$ and UV irradiation compared to cells treated with $Ac_3ManAzNB$ only (FIG. 2, panel d). Western blot analyses of LS174T cells treated with $Ac_3ManAzNB$/UV showed a series of protein bands, indicating the successful incorporation of azido groups into the cell-surface glycoproteins. In comparison, LS174T cells treated with $Ac_3ManAzNB$ only showed the same two endogenous biotinylated protein bands as PBS group. In this way we fully demonstrated the hypothesis that chemical modification of the C1 site of $Ac_4ManAz$ by forming a glycoside could block the whole metabolic labeling process, which would be reactivated in the presence of a specific trigger that can cleave the glycosidic bond to expose the 1-OH.

General procedures for confocal imaging of azido-sugar labeled cells. Cells were seeded onto coverslips in a 6-well plate at a cell density of 40 k/well. $Ac_4ManAz$ or $Ac_3ManAz$ derivatives were added with a final concentration of 50 µM and the cells were incubated at 37° C. for 72 h. The medium was removed and washed with PBS for three times. DBCO-Cy5 (50 µM) in Opti-MEM was then added and the cells were incubated for another 1 h. Then the medium was removed and the cells were washed with PBS for three times. 4% paraformaldehyde (PFA) solution was added to fix the cells for 10 min, followed by staining of cell nucleus with DAPI (2 µg/mL) for 10 min. The coverslips were mounted on microscope slides with the addition of ProLong Gold antifade reagent, and the prepared sample was stored in dark for imaging.

General procedures for flow cytometry analysis of azido-sugar labeled cells. Cells were seeded onto coverslips in a 6-well plate at a cell density of 40 k/well. $Ac_4ManAz$ or Ac$_3$ManAz derivatives were added and incubated with cells for 72 h. After removal of medium and multiple washing steps, DBCO-Cy5 in opti-MEM was added and incubated with cells at 37° C. for 1 h. The opti-MEM was then removed and cells were washed with PBS for three times. Cells were lifted by incubating with trypsin solution (1 mL) at 37° C. for 3 min and transferred to test tubes with addition of 4% PFA solution (0.5 mL). Twenty thousand cells per sample were analyzed by flow cytometry and data analysis was performed on the FCS Express software.

Ac$_3$ManAzNB mediated controlled cell labeling. LS174T cells were seeded onto coverslips in a 6-well plate at a cell density of 40 k/well. Ac$_3$ManAzNB with a final concentration of 50 µM was added. The cells were allowed to attach for 12 h, at which point UV light (20 mW/m$^2$) was applied for 10 min, and the cells were further incubated for 60 h. Cells without UV irradiation were continuously incubated for 72 h. Cell samples for confocal imaging and flow cytometry were then prepared following the above-mentioned procedures.

Ac$_3$ManAzHQ mediated controlled cell labeling. LS174T colon cancer cells or Caco-2 colon cancer cells or human fibroblast IMR90 cells were seeded onto coverslips in a 6-well plate at a cell density of 40 k/well and allowed to attach for overnight. Ac$_3$ManAzHQ with a final concentration of 50 µM was added, followed by the addition of curcumin with a final concentration of 50 µM. Cells treated with PBS or Ac$_3$ManAzHQ only were used as control. After 72-h incubation, cell samples for confocal imaging and flow cytometry were prepared following the above-mentioned procedures.

Western blot analysis of cells treated with azido-sugars. LS174T cells were seeded onto cell culture flasks (25 cm$^2$ growth area) at a density of 1×10$^6$ cells per plate in 5 mL of media. Different azido-sugars were added and incubated with cells for 72 h. The cells were washed with PBS twice and harvested from the flasks using a cell scraper. Cells were pelleted by centrifugation at 1000 rpm for 5 min and re-suspended in 200 µL of lysis buffer (1% SDS, 100 mM Tris.HCl, pH 7.4) containing 1 tablet protease inhibitor (EDTA-free). The lysate was incubated at 4° C. for 30 min, followed by centrifugation at 3000 rcf for 10 min to remove insoluble debris. The total concentration of soluble protein in each sample was determined by bicinchoninic acid (BCA) assay and adjusted to the same concentration. Then 20 µL of the lysate was taken out and incubated with phosphine-PEG$_3$-biotin (2 µL, 5 mM in PBS) at 37° C. for 6 h. Loading buffer was added to each sample and samples were loaded onto 10% SDS-PAGE gel after heating at 95° C. After running the gel for 100 min, proteins were transferred to Hybond P membrane, followed by blocking of the membrane with 5% bovine serum albumin (BSA) in TBST (50 mM Tris.HCl, 150 mM NaCl, 0.1% Tween 20, pH 7.4) for 2 h. The membrane was then incubated with streptavidin-HRP (diluted 1:2000 in TBST) overnight at 4° C., rinsed with TBST for three times and developed by ECL Western Blotting Substrate. For fluorescent visualization of protein bands, 20 µL of cell lysate was directly incubated with DBCO-Cy3 solution for 3 h. After the gel running and membrane transfer, protein bands were visualized using an Image Quant LAS 4010 system with a Cy3/Cy3 (excitation/emission) channel.

Example 3. Investigation of Ac$_4$ManAz Derivatives in Cell-Labeling In Vivo

Figure 3:
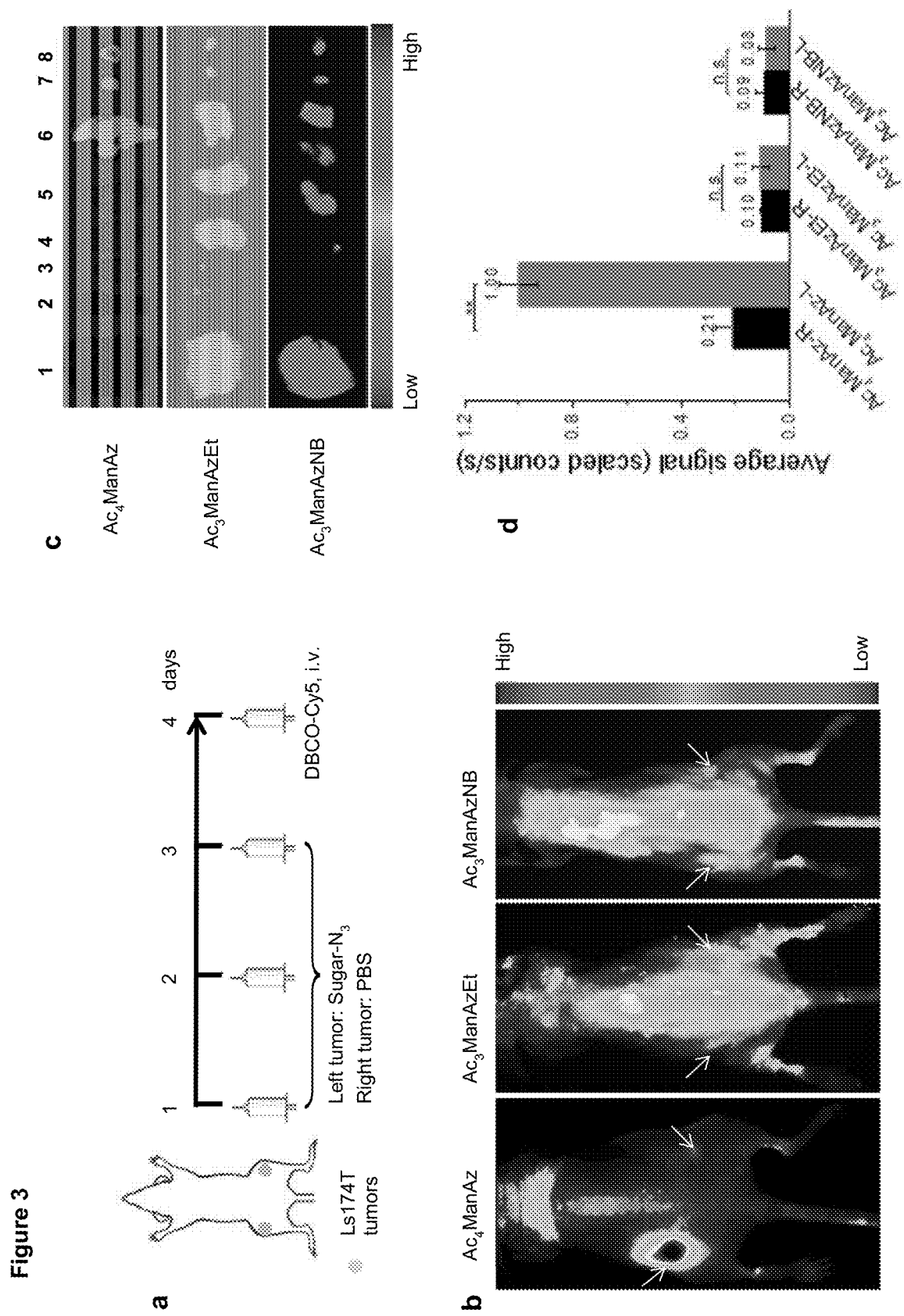
FIG. 3 consists of panels a-d and depicts an in vivo labeling study of $Ac_4ManAz$, $Ac_3ManAzEt$, and $Ac_3ManAzNB$. Panel (a) is a time axis of an in vivo labeling study. Sugar-$N_3$ was injected to the left tumors once daily for three days, and subsequently detected by DBCO-Cy5. Right tumors were pretreated with PBS as control. Panel (b) is a series of images depicting in vivo whole body fluorescence imaging of mice pretreated with $Ac_4ManAz$, $Ac_3ManAzEt$, and $Ac_3ManAzNB$, respectively at 48 h post intravenous injection of DBCO-Cy5. Tumors were shown by yellow arrows. Panel (c) is a series of images depicting ex vivo fluorescence imaging of tumors and main organs (1-liver, 2-spleen, 3-heart, 4-kidney, 5-kidney, 6-lung, 7-right tumor, 8-left tumor). Panel (d) is a graph showing quantification of fluorescence intensity of tumors from different groups (R stands for the right tumor and L means the left tumor). Fluorescence intensity was normalized to scaled counts/s. Data were presented as mean±SEM (n=3) and analyzed by one-way ANOVA (Fisher; 0.01<*P≤0.05; P≤0.01; *P≤0.001).

Next we studied whether Ac$_3$ManAz derivatives including Ac$_3$ManAzEt and Ac$_3$ManAzNB could maintain their blocking effect in vivo. Athymic nude mice bearing subcutaneous LS174T tumors were injected with Ac$_4$ManAz, Ac$_3$ManAzEt or Ac$_3$ManAzNB, respectively to the left tumors once daily for three days. The right tumors were used as control. At 24 h post injection (p.i.), tumors were harvested to determine whether tumor cells were metabolically labeled with azido groups. As expected, tumors treated with Ac$_4$ManAz showed a series of azido-modified glycoproteins while tumors treated with Ac$_3$ManAzEt or Ac$_3$ManAzNB showed the same endogenous protein bands as PBS group, which indicated that Ac$_3$ManAzEt and Ac$_3$ManAzNB failed to metabolically label cancer cells with azido groups in vivo. To understand how the expressed azido groups would improve the tumor accumulation of DBCO-cargo, in a separate study, we intravenously (i.v.) injected DBCO-Cy5 at 24 h p.i. of azido-sugars, and monitored its biodistribution using in vivo fluorescence imaging (FIG. 3, panel a). At 24 h p.i., the left tumors pretreated with Ac$_4$ManAz showed much stronger Cy5 fluorescence intensity (FI) than the right tumors (FIG. 3, panel b), suggesting the successful labeling of tumor cells by Ac$_4$ManAz and the resulting significantly enhanced tumor retention of DBCO-Cy5 via Click reaction in vivo. In comparison, tumors pretreated with Ac$_3$ManAzEt or Ac$_3$ManAzNB showed negligible Cy5 retention enhancement compared to the control tumors. Ex vivo imaging of Ac$_4$ManAz-treated tumors showed an over 4-fold increase in Cy5 FI compared to the control tumors (FIG. 3, panels c and d). For Ac$_3$ManAzEt and Ac$_3$ManAzNB groups, no significant difference in Cy5 FI between the treated tumors and the control tumors was observed. Confocal imaging of the tumor sections treated with Ac$_4$ManAz also showed strong Cy5 fluorescence, in sharp contrast to the negligible Cy5 fluorescence in Ac$_3$ManAzEt and Ac$_3$ManAzNB groups. These experiments not only demonstrated the blocking effect of Ac$_3$ManAzEt and Ac$_3$ManAzNB in vivo but also indicated the excellent in vivo cancer targeting effect mediated by efficient Click chemistry.

In vivo tumor labeling of Ac$_4$ManAz, Ac$_3$ManAzEt, and Ac$_3$ManAzNB. LS174T tumor models were established on 6 week-old athymic nude mice by subcutaneous injection of LS174T colon cancer cells (1.5 million) in HBSS/matrigel (1/1, v/v) to both flanks. When the tumors grew to 5-6 mm, Ac$_4$ManAz or Ac$_3$ManAzEt or Ac$_3$ManAzNB (25 mM, 20 µL) was injected into the left tumors once daily for three days while the same amount of PBS was injected to the right tumors as control (N=3 per group). At 24 h post the last injection, DBCO-Cy5 (5 mg/kg) was i.v. injected and its biodistribution was monitored via in vivo fluorescence imaging. Prior to imaging, nude mice were placed on the sample stage equipped with anesthesia input and output ports, and imaged by the Maestro In-Vivo Fluorescence Imaging System. The excitation filter of 575-605 nm was used. The tunable emission filter was automatically stepped in 10-nm increments from 630 to 850 nm with an exposure time of 50 ms for images taken at each wavelength. Collected images were analyzed by the Maestro software, which uses spectral unmixing algorithms to subtract autofluorescence from Cy5 signals. Tumors and major organs were harvested from mice at 24 h post injection of DBCO-Cy5. Ex vivo images were collected similarly using the Maestro system. Fluorescence intensity at selected ROIs was quantified using Maestro imaging software. All values were presented as means±standard deviation (n=3).

Western blot analysis of tissues. Tumors and organs harvested from azido-sugar treated mice were transferred into glass tubes containing 2 mL of lysis buffer (1% SDS, 100 mM Tris HCl, pH 7.4), homogenized, and incubated at 4° C. for 30 min. The lysates were then centrifuged at 3000 rcf for 10 min to remove the insoluble debris. Total soluble protein concentrations were determined by BCA assay and adjusted to 5 mg/mL for each group. The rest of procedures were the same as the above-mentioned western blot analysis of cells.

Confocal imaging of tumor tissue sections. After ex vivo imaging, tumors were directly frozen in O.C.T. compound and sectioned on a cryostat (Leica CM3050S) with a thickness of 6-8 μm. DAPI in PBS (2 μg/mL) was added onto the tissue-attaching microscope slides to stain cell nucleus. After 10 min, DAPI solution was removed and tissues were washed with PBS for three times. Coverslips were mounted on the microscope slides with the addition of ProLong Gold antifade reagent, and the prepared sample was stored in dark for confocal imaging.

Example 4. Investigation of Alternative Self-Immolative Linkers

Figure 4:
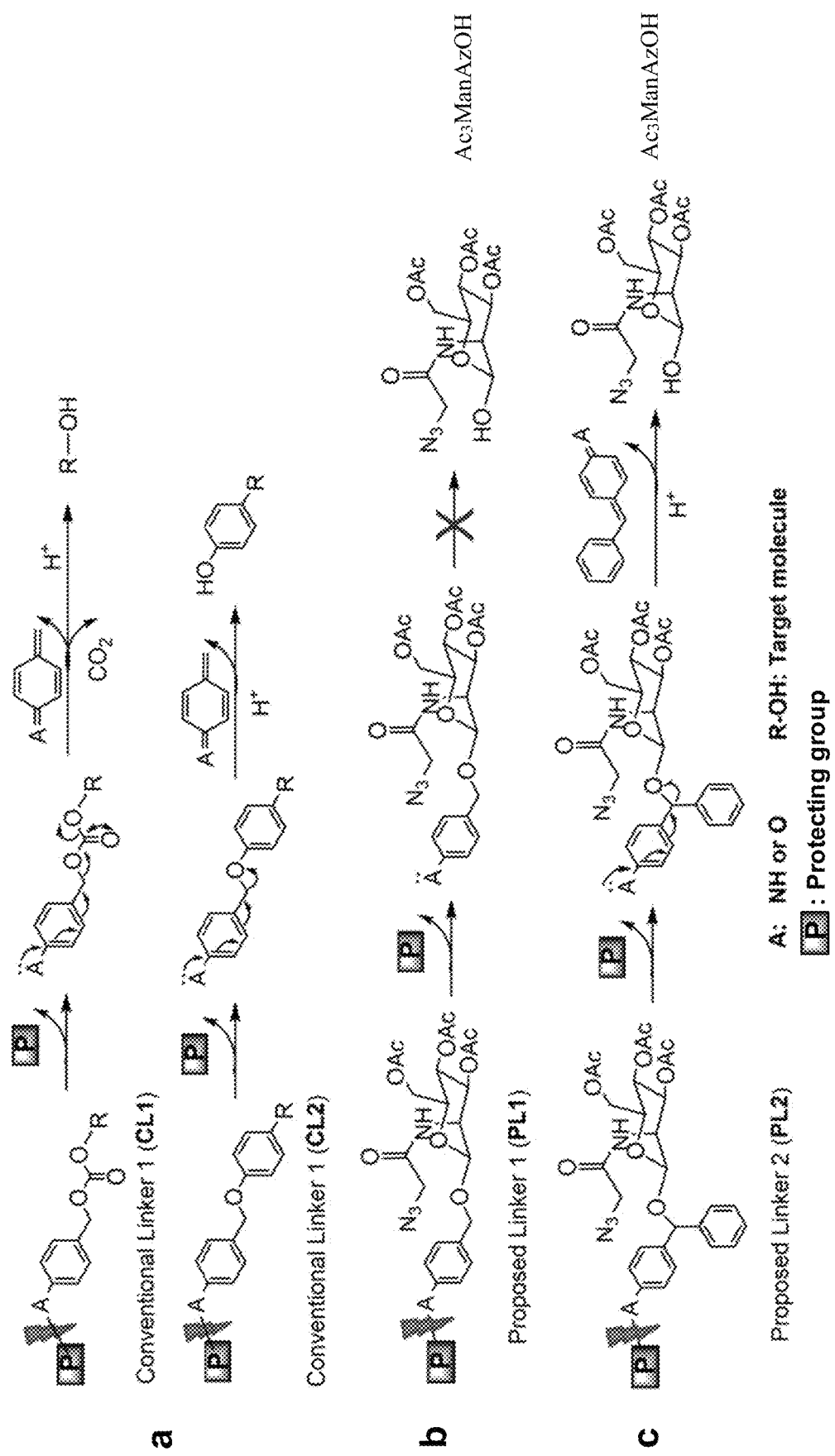
FIG. 4 consists of three panels. Panel (a) depicts schemes showing the use of two conventional self-immolative linkers (CL1 and CL2) used in conventional prodrug systems. Panel (b) shows a first proposed linker PL1 derived from CL2. Panel (c) shows a second proposed linker (PL2) modified from PL1. The additional phenyl ring stabilizes the cleaved product, thus facilitating the degradation process.

After demonstrating the controlled labeling strategy, we next aimed to apply it to in vivo cancer labeling and targeting. Since UV is not a practical trigger in vivo because of its poor tissue penetration and potential damage to healthy tissues, we aimed to develop $Ac_3ManAz$ derivatives that are responsive to internal cancer-specific triggers such as redox dysregulation, elevated oxidant level, and overexpressed enzymes. However, different from UV irradiation which can directly cleave an 2-nitrobenzyl glycosidic bond into hydroxyl group, these triggers are not able to directly cleave the glycosidic bond, thus requiring the incorporation of a self-immolative linker that can eventually release the hydroxyl group after trigger-induced cleavage of the protecting group. Two conventional self-immolative linkers, CL1 and CL2, have been widely used in prodrug design (FIG. 4, panel a). Upon removal of the protecting group, CL1 can rapidly get rid of a $CO_2$ molecule to expose the hydroxyl group. However, CL1 contains a carbonate bond which can be easily degraded by cellular esterase, and thus is not available for this design. CL2 can rapidly release the phenol structure as a good leaving group upon removal of the protecting group. Considering that the sugar compound with unmasked 1-OH might be a good leaving group, we designed PL1 (FIG. 4, panel b) with a similar structure to CL2 and incorporate it into hydrogen peroxide ($H_2O_2$)-responsive $Ac_3ManAzHB$. However, $Ac_3ManAzHB$ failed to release $Ac_3ManAzOH$ even though the protecting group was easily removed by $H_2O_2$. We then designed PL2 with an additional phenyl group linked to the α-carbon of PL1 based on the assumption that the greatly stabilized degradation product would facilitate the cleavage of the self-immolative linker (FIG. 4, panel c).

Example 5. Investigation of Additional Trigger-Responsive Groups

To investigate the feasibility of PL2 as a self-immolative linker, $Ac_3ManAzHQ$ with a NQO1 enzyme-responsive protecting group was synthesized and its degradation in vitro was studied using sodium dithionite as a representative reducing agent. $Ac_3ManAzHQ$ underwent rapid degradation in the presence of sodium dithionite, with ESI MS confirming the formation of $Ac_3ManAzOH$ as the degradation product. We then tested the controlled metabolic labeling capability of NQO1-responsive $Ac_3ManAzHQ$ in vitro. After incubated with $Ac_3ManAzHQ$ for three days and DBCO-Cy5 for 1 h, LS174T colon cancer cells rich in NQO1 enzyme showed uniform Cy5 fluorescence on the cell surface, indicating the successful expression of azido groups. Caco-2 colon cancer and IMR-90 human fibroblast cell lines which are NQO1-deficient, however, showed negligible Cy5 fluorescence on the cell surface. To further confirm the important role of NQO1 enzyme in activating the metabolic labeling capability of $Ac_3ManAzHQ$, we studied whether the inhibitor of NQO1 enzyme, curcumin, was able to inhibit $Ac_3ManAzHQ$-mediated cell labeling. As a result, a significant reduction of labeling efficiency was observed in LS174T cells co-incubated with $Ac_3ManAzHQ$ and curcumin compared to cells treated with $Ac_3ManAzHQ$ only.

A library of trigger-activatable $Ac_3ManAz$ derivatives that are responsive to either external triggers (near infrared (NIR) light) or internal triggers ($H_2O_2$, tumor hypoxia environment, NAD(P)H dehydrogenase quinone 1 (NQO1), and histone deacetylase (HDAC)/cathepsin L (CTSL)) are shown in FIG. 5. Among them, HDAC/CTSL responsive sugar derivative, E-S, enabled selective cancer labeling both in vitro and in vivo.

Example 6. Synthesis of HDAC/CTSL Responsive Sugar Derivative E-S

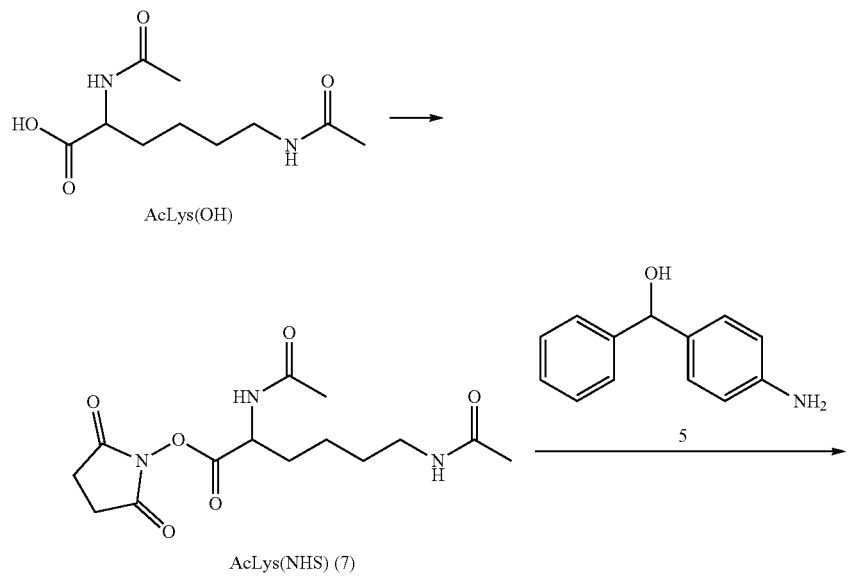

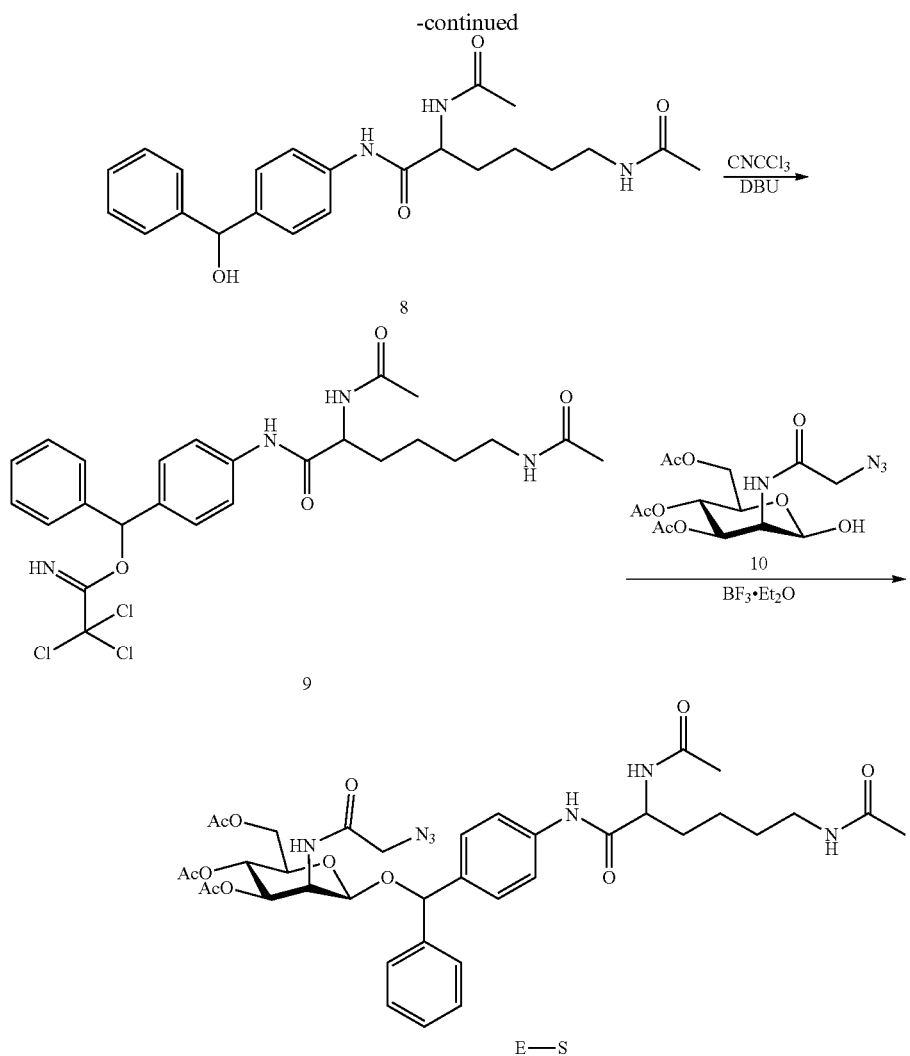

Synthesis of AcLys(NHS) (7). AcLys(OH) (2.0 mmol, 460 mg) and trimethylamine (2.1 mmol, 212 mg) was dissolved in anhydrous DMF (40 mL), followed by the addition of DCC (2.1 mmol, 433 mg) and NHS (2.1 mmol, 242 mg). The reaction mixture was stirred at room temperature for 24 h. The precipitate was filtered off, and the solvent was removed under reduced pressure. The crude product was purified by silica gel column chromatography using ethyl acetate as the eluent to yield a light yellow solid (70% yield).

Synthesis of Compound 8. AcLys(NHS) (1.2 mmol) and compound 5 (1.2 mmol) were dissolved in anhydrous DMF (30 mL), followed by the addition of trimethylamine (1.2 mmol). The mixture was stirred at 40° C. for 24 h. After removal of the solvent, the crude product was purified by silica gel column chromatography using ethyl acetate to ethyl acetate/methanol (20/1, v/v) as the eluent to yield a light yellow solid (60% yield). $^1$H NMR (CD$_3$OD, 500 MHz): δ (ppm) 7.50 (d, 2H, Ph), 7.34 (d, 2H, Ph), 7.29 (m, 4H, Ph), 7.21 (t, 1H, Ph), 5.74 (s, 1H, CH(OH)), 4.39 (m, 1H, CHCH$_2$CH$_2$CH$_2$CH$_2$NHC(O)CH$_3$), 3.15 (t, 2H, CHCH$_2$CH$_2$CH$_2$CH$_2$NHC(O)CH$_3$), 2.00 (s, 3H, CHCH$_2$CH$_2$CH$_2$CH$_2$NHC(O)CH$_3$), 1.89 (s, 3H, CHNHC(O)CH$_3$), 1.83&1.72 (m, 2H, CHCH$_2$CH$_2$CH$_2$CH$_2$NHC(O)CH$_3$), 1.53 (m, 2H, CHCH$_2$CH$_2$CH$_2$CH$_2$NHC(O)CH$_3$), 1.41 (m, 2H, CHCH$_2$CH$_2$CH$_2$CH$_2$NHC(O)CH$_3$). $^{13}$C NMR (CD$_3$OD, 500 MHz): 172.2, 172.0, 171.7, 144.7, 140.9, 137.3, 128.1, 127.0, 126.5, 120.1, 75.3, 54.4, 38.9, 31.7, 28.9, 23.1, 21.4, 21.2. ESI MS (m/z): calculated for C$_{23}$H$_{29}$N$_3$O$_4$Na [M+Na]+434.2, found 434.2.

Synthesis of AcLys(DPM-CNCCl$_3$) (9). Compound 8 (0.5 mmol) and CNCCl$_3$ (5.0 mmol) were dissolved in anhydrous THF, followed by the addition of 1,8-diazabicycloundec-7-ene (DBU, 0.5 mmol). The reaction mixture was stirred at room temperature for 4 h. After removal of the solvent, the crude product was purified by silica gel column chromatography to yield a white solid. $^1$H NMR (CD$_3$OD, 500 MHz) δ (ppm) 7.99 (m, 1H), 7.53 (d, J=8.4 Hz, 2H), 7.38-7.19 (m, 7H), 5.27 (s, 1H), 4.43 (m, 1H), 3.73 (m, 1H), 3.17 (m, 2H), 2.02 (s, 3H), 1.91 (s, 3H), 1.84&1.73 (m, 2H), 1.55 (m, 2H), 1.44 (m, 2H). $^{13}$C NMR (CD$_3$OD, 500 MHz): 208.42, 172.2, 172.1, 171.7, 142.4, 138.5, 137.6, 128.2, 127.3, 126.8, 120.2, 101.8, 85.0, 64.4, 54.3, 39.1, 31.7, 28.9, 23.1, 21.4, 21.3.

Synthesis of Ac$_3$ManAzOH (10). Ac$_4$ManAz (0.5 mmol) and ammonium carbonate (0.75 mmol) were dissolved in THF/methanol (2/1, v/v) and stirred at room temperature. After 12 h, the solvent was removed and the crude product was purified by silica gel column chromatography to yield a white solid. NMR (CDCl$_3$, 500 MHz): δ (ppm) 6.56 (d, J=9.2 Hz, 1H), 5.44 (dd, J=10.1, 4.2 Hz, 1H), 5.22 (s, 1H), 5.18 (t, 1H), 4.63 (ddd, J=9.2, 4.2, 1.8 Hz, 1H), 4.31-4.01 (m, 5H), 3.74 (m, 1H), 2.14&2.08&2.05 (s, 9H). $^{13}$C NMR (CDCl$_3$, 500 MHz): δ (ppm) 171.0, 170.4, 170.1, 167.1, 93.4, 69.2, 68.4, 66.0, 62.5, 52.7, 50.9, 21.1, 21.0, 20.9.

Synthesis of E-S. Ac$_3$ManAzOH (0.2 mmol) and AcLys (DPM-CNCCl$_3$)) were dissolved in anhydrous acetonitrile, followed by the addition of boron trifluoride etherate (2.0 mmol). The mixture was stirred at 0° C. for 1 h. After removal of the solvent, the crude product was purified by silica gel column chromatography and HPLC to yield a white solid. $^1$H NMR (CDCl$_3$, 500 MHz): δ (ppm) 7.55 (m, 2H, Ph), 7.35-7.28 (m, 7H, Ph), 6.73 (m, 1H, CH$_3$C(O)NHCH), 6.50 (m, 1H, CH$_2$C(O)NHCH), 5.95 (m, 1H, CH$_3$C(O)NHCH$_2$), 5.65 (s, 1H, PhCH), 5.43 (ddd, J=10.1, 8.3, 4.2 Hz, 1H, CH$_2$CHCHCH), 5.17 (td, J=10.2, 3.2 Hz, 1H, CH$_2$CHCHCH), 4.75-4.80 (m, 1H, NHCHCHO), 4.68 (m, 1H, NHCHCHO), 4.55 (q, J=7.3 Hz, 1H, CHCH$_2$CH$_2$CH$_2$CH$_2$NHC(O)CH$_3$), 4.18&4.05 (m, 2H, CH$_2$CHCHCH), 4.02 (m, 2H, COCH$_2$N$_3$), 3.94 (m, 1H, CH$_2$CHCHCH), 3.22 (m, 2H, CHCH$_2$CH$_2$CH$_2$CH$_2$NHC(O)CH$_3$), 2.12&2.06&2.03&1.99&1.96 (15H, CH$_3$C(O)O), 1.93&1.74 (m, 2H, CHCH$_2$CH$_2$CH$_2$CH$_2$NHC(O)CH$_3$), 1.51 (m, 2H, CHCH$_2$CH$_2$CH$_2$CH$_2$NHC(O)CH$_3$), 1.38 (m, 2H, CHCH$_2$CH$_2$CH$_2$CH$_2$NHC(O)CH$_3$). $^{13}$C NMR (CDCl$_3$, 500 MHz): δ (ppm) 171.5, 171.2, 170.7, 170.4, 170.0, 170.0, 166.8, 141.2, 137.8, 137.2, 135.6, 129.1, 128.8, 128.5, 127.5, 126.7, 120.2, 80.0, 77.5, 77.5, 77.3, 77.2, 77.0, 69.9, 69.0, 65.8, 62.3, 53.9, 52.7, 50.5, 38.8, 31.3, 29.1, 23.4, 22.5, 21.1, 20.9. HR ESI MS (m/z): calculated for C$_{37}$H$_{48}$N$_7$O$_{12}$ [M+H]$^+$ 782.3361, found 782.3354.

Example 7. In Vitro Studies for Improving Selectivity for Labeling Cancer Cells

After demonstrating the feasibility of PL2 for the design of trigger-activatable caged sugar precursors, we next aimed to develop Ac$_3$ManAz derivatives that possess better cancer-selective labeling capability. Compared to NQO1 enzyme, several other enzymes better represent the general difference between cancer cells and normal cells. For example, both histone deacetylase (HDAC) and cathepsin L (CTSL) are reported over-expressed in cancer cell lines. In our design of E-S which combines HDAC and CTSL as a single trigger, HDAC removes the acetyl group of the lysine residue first, followed by cleavage of the peptide bond by CTSL and removal of the self-immolative linker, releasing the metabolically active Ac$_3$ManAzOH (FIG. 6, panel A). To detect HDAC/CTSL activity in different cell lines, we first synthesized a fluorescence reporter (Naph-Lys) whose fluorescence would turn on in the presence of both HDAC and CTSL. HDAC/CTSL activity in most cancer cell lines including LS174T colon cancer cell, MCF-7 breast cancer cell, 4T1 triple negative breast cancer cell, HeLa cell, and HepG2 liver cancer cell was much higher than that in healthy cell line including IMR-90 human fibroblast cell. In the presence of the inhibitor for either HDAC (Trichostatin A (TSA)) or CTSL (Z-FY-CHO), however, turn-on fluorescence intensity of Naph-Lys greatly decreased as a result of reduced enzyme activity. We then investigated controlled cell labeling capability of E-S in vitro by incubating different cell lines with E-S for three days and subsequently detecting the potentially expressed azido groups using DBCO-Cy5. CLSM images showed clear and bright Cy5 fluorescence signal on the surface of LS174T cells, in sharp contrast to the negligible Cy5 fluorescence observed on the surface of IMR-90 cells (FIG. 6, panels b and c), suggesting selective labeling capability of E-S in LS174T colon cancer cells over human fibroblast cells. When LS174T cells were co-incubated with E-S and inhibitor of either HDAC (TSA) or CTSL (Z-FY-CHO), labeling efficiency of E-S was greatly reduced FIG. 6, panels b and d), which implied HDAC/CTSL-induced reactivation of the labeling process of E-S.

To gain a better understanding of the metabolic labeling process of E-S, we analyzed the labeling kinetics of E-S in vitro. After incubating LS174T cells with various concentrations (10 μM, 50 μM, 200 μM, and 1 mM) of E-S for different time (1 h, 3 h, 6 h, 12 h, 24 h, 48 h, and 72 h), cell surface azides were detected by DBCO-Cy5. Because of the low cellular uptake of DBCO-Cy5, cell surface azides could be semi-quantitatively determined and compared via measurement of Cy5 fluorescence intensity. Metabolic labeling process of E-S is time- and concentration-dependent, with the number of cell-surface azides approaching to a plateau value at 48 h. An estimation of the number density of cell surface azides indicated a value of $10^6$-$10^7$ azides per cell after incubating LS174T cells with E-S (200 μM) for 48 h. Compared to the number density of protein receptors in conventional targeting strategies which was reported to be ~$10^3$ to $10^4$ per cell, the targeting efficiency resulting from azido-sugars coupled with a click reaction could potentially be much higher.

Synthetic Route of HDAC/CTSL Fluorescent Reporter (Naph-Lys)

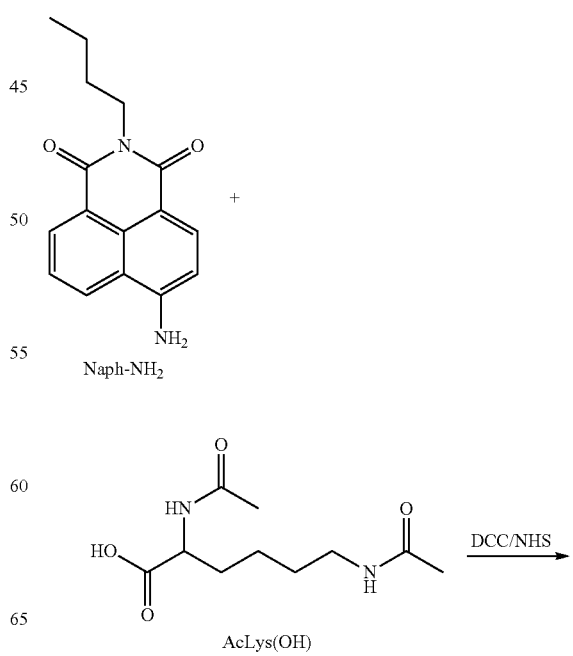

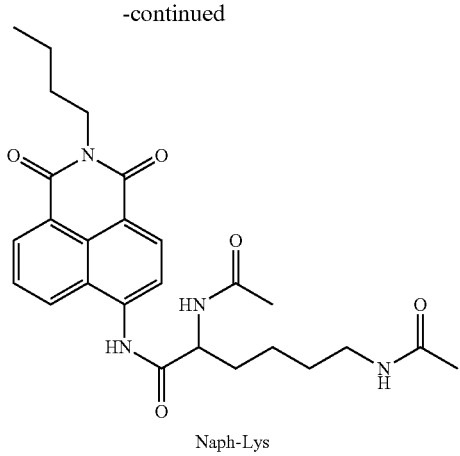

Naph-Lys

Synthesis of Naph-NH$_2$. 4-Amino-1,8-naphthalic anhydride (10 mmol, 2.13 g) was dissolved in ethanol under nitrogen atmosphere and brought to reflux. 1-butylamine was then added and the mixture was further refluxed for 8 h. After cooling down, the solvent was removed under reduced pressure, and the crude product was purified by silica gel column chromatography using DCM/ethyl acetate (2/1, v/v) as the eluent (75% yield). $^1$H NMR (CDCl$_3$, 500 MHz): δ 8.60 (d, 1H, C(O)CCHCHCH), 8.42 (d, 1H, C(O)CCHCHCH), 8.10 (d, 1H C(O)CCHCHCH), 7.66 (t, 1H, C(O)CCHCH), 6.89 (d, 1H, C(O)CCHCH), 4.94 (s, 2H, NH$_2$), 4.18 (t, 2H, CH$_2$CH$_2$CH$_2$CH$_3$), 1.71 (m, 2H, CH$_2$CH$_2$CH$_2$CH$_3$), 1.45 (m, 2H, CH$_2$CH$_2$CH$_2$CH$_3$), 0.97 (s, 3H, CH$_2$CH$_2$CH$_2$CH$_3$).

Synthesis of Naph-Lys. Naph-NH$_2$ (1.0 mmol) and AcLys(OH) (1.0 mmol) were dissolved in anhydrous DMF (40 mL), followed by the addition of DCC (1.1 mmol), NHS (1.1 mmol), and triethylamine (1.0 mmol). The mixture was stirred at 45° C. for 48 h. The precipitate was filtered off and the solvent was removed under reduced pressure. The crude product was purified by silica gel column chromatography using hexane/ethyl acetate (3/1, v/v) as the eluent to yield a yellow solid (60% yield). LRMS (ESI) m/z: calculated for C$_{26}$H$_{33}$N$_4$O$_5$ [M+H]+481.2, found 481.2. $^1$H NMR (CDCl$_3$, 500 MHz): δ 8.57 (dd, 1H, C(O)CCHCHCH), 8.52 (d, 1H C(O)CCHCH), 8.51 (dd, 1H, C(O)CCHCHCH), 8.12 (dd, 1H, C(O)CCHCH), 7.84 (dd, 1H, C(O)CCHCHCH), 4.62 (dd, 1H, CHCH$_2$CH$_2$CH$_2$CH$_2$), 4.14 (t, 2H, CH$_2$CH$_2$CH$_2$CH$_3$), 3.22 (t, 2H, CHCH$_2$CH$_2$CH$_2$CH$_2$), 2.06 (s, 3H, CH$_3$C(O)NHCH), 1.98 (m, 2H, CHCH$_2$CH$_2$CH$_2$CH$_2$), 1.92 (s, 3H, CH$_3$C(O)NHCH$_2$), 1.69 (m, 2H, CH$_2$CH$_2$CH$_2$CH$_3$), 1.60 (m, 2H, CHCH$_2$CH$_2$CH$_2$CH$_2$), 1.53 (m, 2H, CHCH$_2$CH$_2$CH$_2$CH$_2$), 1.43 (m, 2H, CH$_2$CH$_2$CH$_2$CH$_3$), 0.99 (m, 3H, CH$_2$CH$_2$CH$_2$CH$_3$).

Detection of cellular HDAC/CTSL activity. Cells were seeded in a 24-well plate at a cell density of 8 k/well, and were allowed to attach for overnight. Naph-Lys (50 µM) in OptiMEM was added and incubated with cells for different time (30 min, 1 h, 2 h, and 4 h). After removal of the OptiMEM and washing with PBS twice, cells were fixed with 4% PFA for 10 min and stained with DAPI (2 ng/mL) for 10 min. Average fluorescence intensity of cells were measured on a GE-Analyzer using DAPI and FITC channels. The DAPI channel was used for determining cell number per well. The FITC channel was used to determine the total fluorescence intensity of released Naph-NH$_2$ per well. Data were presented with the average fluorescence intensity per cell.

Inhibitory effect of TSA and Z-FY-CHO on cellular HDAC/CTSL activity. TSA and Z-FY-CHO are known to be the inhibitor of HDAC and CTSL, respectively. To study their inhibitory effect, cells were seeded in a 24-well plate at a cell density of 8 k/well, and were allowed to attach for overnight. Cells were then divided into 4 groups: group 1 cells were added Naph-Lys (50 µM); group 2 cells were added Naph-Lys (50 µM)+TSA (1 µM); group 3 cells were added Naph-Lys (50 µM)+Z-FY-CHO (20 µM); group 4 cells were added PBS as negative control. The cells were incubated for 4 h, washed with PBS, fixed with 4% PFA for 10 min, and stained with DAPI (2 µg/mL) for 10 min. Average fluorescence intensity of cells were measured on a GE-Analyzer using DAPI and FITC channels.

E-S mediated controlled cell labeling in vitro. LS174T colon cancer cells or human fibroblast IMR90 cells were seeded onto coverslips in a 6-well plate at a cell density of 40 k/well. E-S with a final concentration of 50 µM was added, followed by the addition of either TSA (1 µM) or Z-FY-CHO (50 µM). Cells treated with PBS or E-S only were used as the control. After 72-h incubation, the medium was removed and cell samples for confocal imaging and GE-Analyzer measurements were prepared similarly to above-mentioned procedures.

Figure 12:
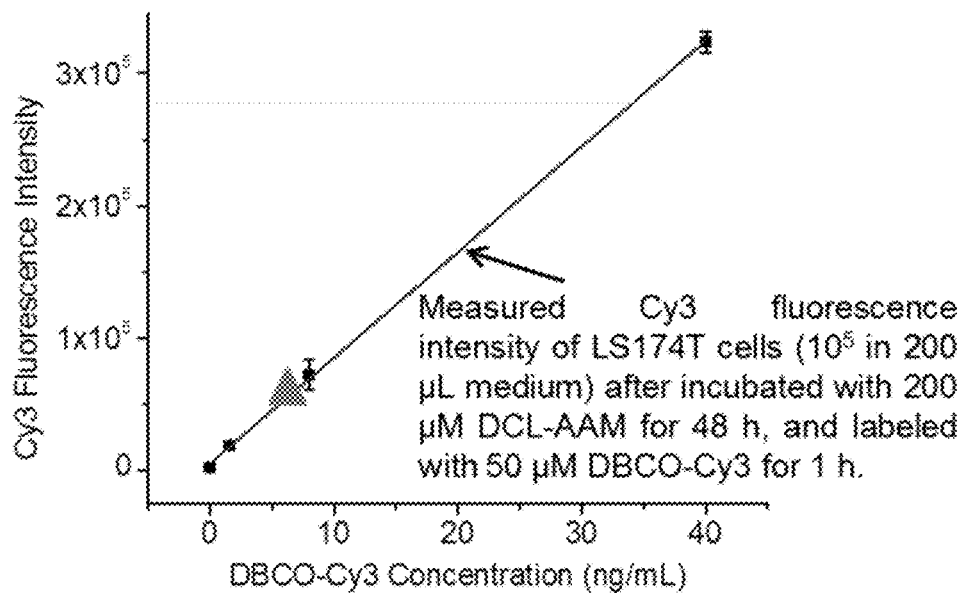
FIG. 12. Method for calculating the number of expressed azido groups per cell ($N_{azide}$/cell). Mass of DBCO-Cy3 per cell: (7.5 ng/mL*200 µL)/100000 cells=$1.5*10^{-5}$*ng/cell. Moles of azides per cell: ($1.5*10^{-5}$ ng/cell)/(983.18 g/mol)=$1.5*10^{-17}$ mol. Number of azides per cell: $1.5*10^{-17}$ moles*($6.02*10^{23}$ mol$^{-1}$)=$9.0*10^6$.

Labeling kinetics of E-S in vitro. LS174T cells were seeded in black 96-well plates, and incubated with various concentrations of E-S (10 µM, 50 µM, 200 µM, and 1 mM) for different time (3 h, 6 h, 12 h, 24 h, 48 h, and 72 h). After removal of the medium and washing with PBS for three times, cells were incubated with DBCO-Cy3 (20 µM) in OptiMEM for 2 h. After removal of DBCO-Cy3 solution, cells in 3 triplicate wells were lifted with trypsin and counted under a microscope for determination of cell number per well (N$_{cell}$/well); cells in another 3 triplicate wells were lysed and Cy3 fluorescence was measured on a plate reader. A gradient concentration of DBCO-Cy3 solution was used for determination of standard curve and calculation of the number of azido groups on the cell surface. The number of expressed azido groups per cell (Name/cell) was estimated using the method illustrated by FIG. 12.

Western blot analysis of E-S treated cells. LS174T cells were seeded onto cell culture flasks (25 cm$^2$ growth area) at a density of 1×10$^6$ cells per plate in 5 mL of media, and allowed to attach for overnight. Cells were then treated with E-S (50 µM), E-S (50 µM)+TSA (1 µM), E-S (50 µM)+Z-FY-CHO (50 µM), and PBS, respectively for 72 h. After removal of the solvent and multiple washing with PBS, cells were harvested from the flasks using a cell scraper. The rest of procedures were the same as the abovementioned general procedures for western blot analysis of cells.

Pharmacokinetics Profile of E-S
Radiolabeling of E-S
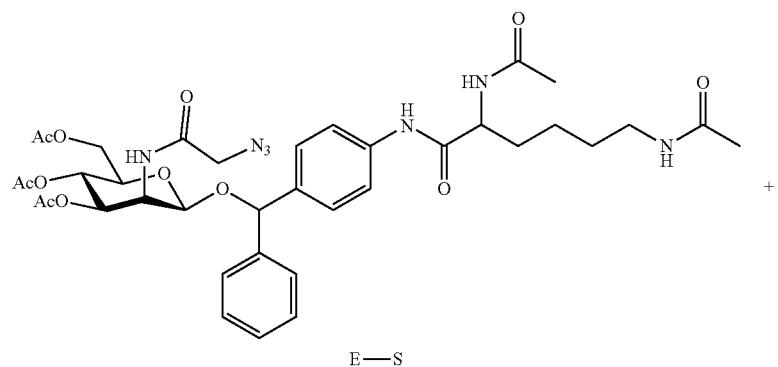
E—S
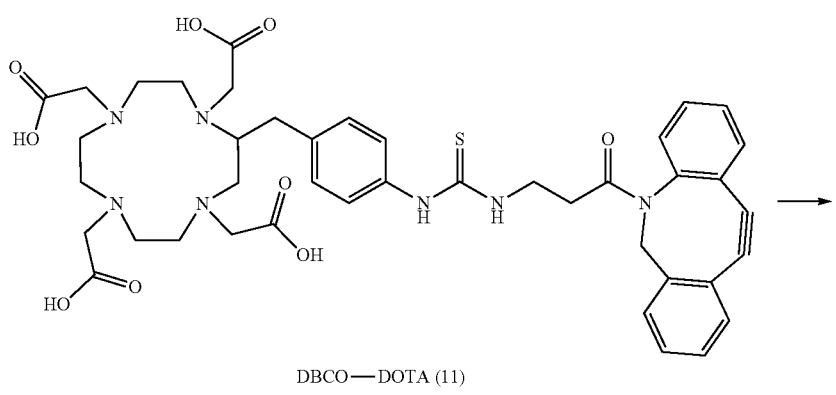
DBCO—DOTA (11)
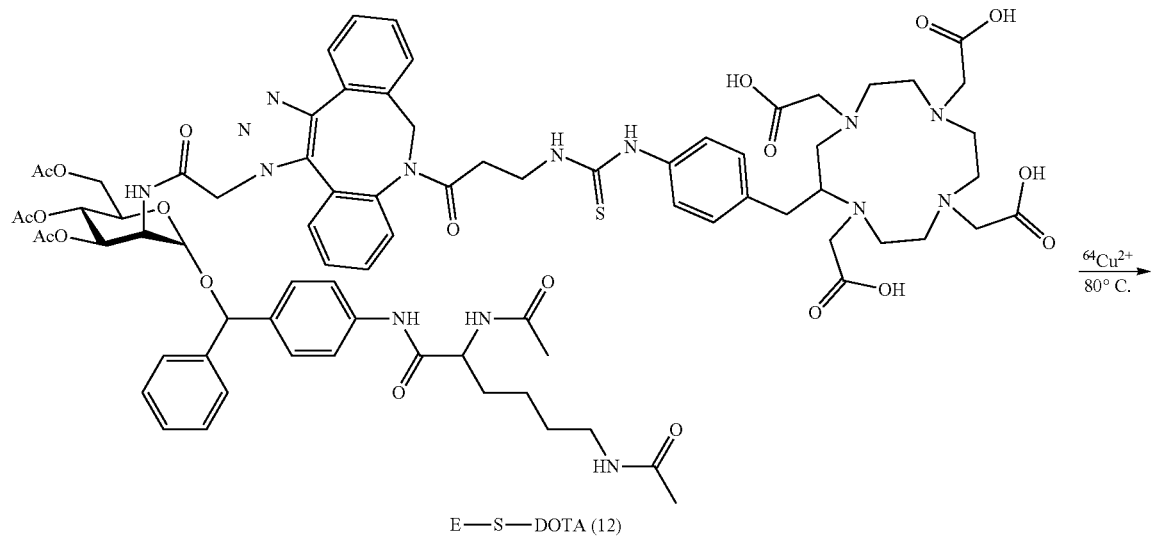
E—S—DOTA (12)

-continued

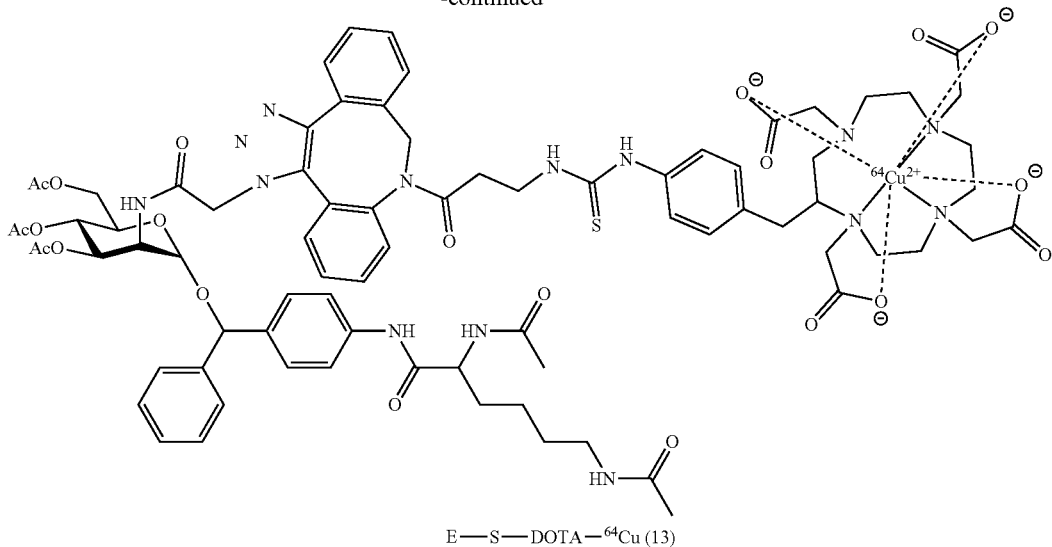

E—S—DOTA—⁶⁴Cu (13)

Synthesis of DBCO-DOTA. P-SCN-Bn-DOTA (0.05 mmol, 34 mg) and DBCO-amine (0.05 mmol, 14 mg) were suspended in anhydrous DMF (1 mL). Triethylamine (0.2 mmol, 20 mg) was added and the mixture was stirred at 40° C. HPLC measurements showed complete reaction after 12 h. The solvent was removed under reduced pressure and the product was used without further purification. LRMS (ESI) m/z: calculated for $C_{42}H_{50}N_7O_9S$ $[M+H]^+$ 828.3, found 828.2.

Synthesis of E-S-DOTA. DBCO-DOTA (0.003 mmol, 2.5 mg) and E-S (0.003 mmol, 2.3 mg) were dissolved in methanol. The mixture was stirred at room temperature for 1 h, at which time point HPLC showed complete consumption of the starting materials.

⁶⁴Cu-labeling of E-S-DOTA. The ⁶⁴Cu chloride (400 μCi, 0.1 ng of ⁶⁴Cu) in $NH_4OAc$ buffer solution (0.1 M, pH=5.5, 1 mL) was mixed with E-S-DOTA (2 mg) in PBS. The mixture was vigorously stirred at 80° C. for 1 h, at which time point HPLC showed complete consumption of free ⁶⁴Cu. The product solution was directly used without further purification.

Pharmacokinetics study of E-S-DOTA-⁶⁴Cu. E-S-DOTA-⁶⁴Cu solution (~100 μCi) was i.v. injected into female athymic nude mice bearing LS174T tumors (N=3). At selected time points (10 min, 30 min, 1 h, 3 h, 6 h, 12 h, and 24 h p.i.), blood was collected from orbital sinus using capillary tubes. Capillary tube was weighed before blood collection. The collected blood samples were weighed and measured for the ⁶⁴Cu radioactivity with a Wizard2 automatic γ-counter using appropriate energy window at photopeak of 511 KeV. Raw counts were corrected for background, decay, and weight. Corrected counts were converted to microcurie (μCi) per gram blood via a previously determined calibration curve. The radioactivity in each blood sample was calculated and presented as the percentage of injected dose per gram of blood (% ID/g). After the blood collection at 24 h p.i., tumors and major organs were harvested for measurement of the residual radioactivity. The radioactivity in each tissue sample was calculated as the percentage of injected dose per gram of tissue (% ID/g).

Example 8. In Vivo Studies for Improving Selectivity for Labeling Cancer Cells

Figure 7:
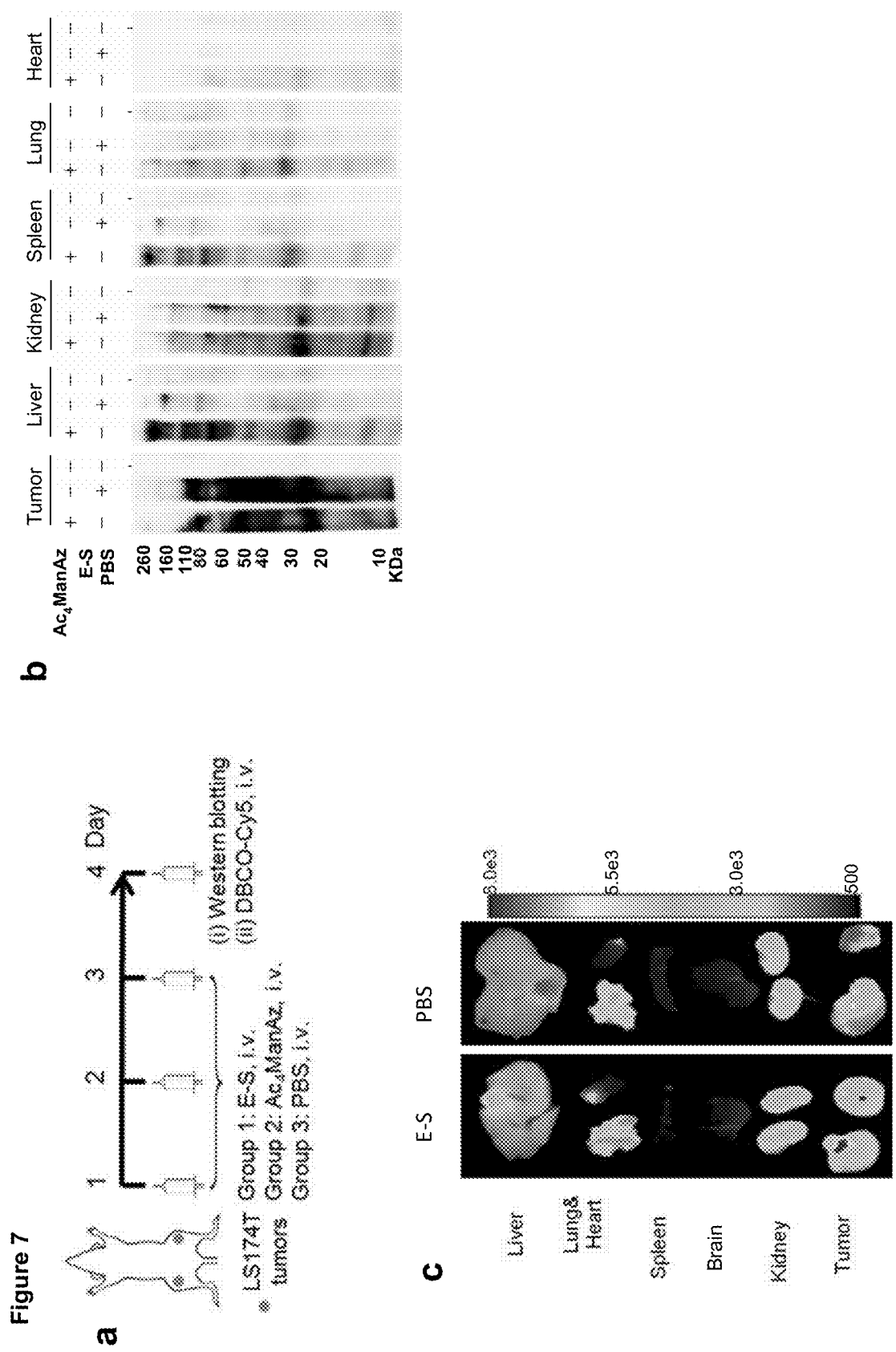
FIG. 7 is a series of images showing E-S mediated selective tumor labeling in vivo. Panel (a) shows a time axis of in vivo labeling study. E-S (60 mg/kg) or $Ac_4ManAz$ (40 mg/kg) or PBS was injected intravenously once daily for three days. The metabolic expression of azido groups was analyzed by western blot analysis or by monitoring the biodistribution of intravenously injected DBCO-Cy5 (10 mg/kg). Panel (b) contains a western blot analysis of tissues collected from mice that were treated with E-S, $Ac_4ManAz$, and PBS, respectively once daily for three days. Panel (c) is an image showing ex vivo whole body fluorescence imaging of mice pretreated with E-S and PBS, respectively at 24 h post injection of DBCO-Cy5. Tumors were shown by yellow arrows. Panel (d) is a bar graph showing quantification of fluorescence intensity of tumors and organs. Panel (e) is CLSM images of tumor tissue sections harvested from athymic nude mice at 8 h, 12 h, and 24 h post i.v. injection of E-S (60 mg/kg), respectively. Tumor tissue sections were labeled with DBCO-Cy5 for 30 min. Scale bar: 10 μm. Panel (f) is a bar graph showing normalized average Cy5 fluorescence intensity of tumor tissue sections harvested at different time post E-S injection. Panel (g) is a bar graph showing normalized Cy5 fluorescence intensity of tumor tissue sections from mice treated with different number of E-S doses. All of the numerical data were presented as mean±SEM and analyzed by one-way ANOVA (Fisher; 0.01<* P≤0.05;  P≤0.01;  P≤0.001).

After demonstrating the controlled labeling property of HDAC/CTSL-responsive E-S in vitro, we next studied the cancer-selective labeling capability of E-S in vivo. E-S was i.v. injected into athymic nude mice bearing LS174T tumors once daily for three consecutive days. Mice i.v. treated with $Ac_4ManAz$ and PBS were used as controls (FIG. 7, panel (a)). Western blotting analyses of tumor tissues at 24 h p.i. of azido-sugars showed an increase in the amount of azido-modified proteins in the E-S group compared to the PBS group, while negligible differences in the amount of azido-modified proteins in the liver, spleen, heart, and lung were observed between E-S and PBS groups (FIG. 7, panel (b)). In contrast, $Ac_4ManAz$ with no labeling selectivity showed non-specific labeling in normal tissues, with a considerable amount of azido groups expressed in liver, spleen, lung, and kidney tissues (FIG. 7, panel b). These experiments demonstrated the superior cancer-selective labeling capability of E-S in vivo in comparison with $Ac_4ManAz$. In a separate study, DBCO-Cy5 was i.v. injected at 24 h post azido-sugar injections and its biodistribution was monitored. At 48 h p.i. of DBCO-Cy5, tumors in E-S group showed significantly enhanced Cy5 retention than tumors in PBS group (FIG. 7, panel c). Imaging of the harvested tumors in E-S group showed a 1.52-fold Cy5 fluorescence intensity compared to PBS group, while Cy5 retention in liver, spleen, heart, lung, and kidney was non-significantly changed (FIG. 7, panels c and d). Compared to $Ac_4ManAz$ group, DBCO-Cy5 in E-S group showed improved accumulation in tumor. Together, these experiments demonstrated that E-S was able to selectively label LS174T tumors in vivo and that the expressed azido groups could significantly enhance the tumor accumulation of DBCO-Cy5 via Click chemistry.

We next studied the labeling kinetics of E-S in vivo in an effort to better understand E-S mediated tumor labeling and the potential of subsequent tumor targeting effect via Click reaction. Pharmacokinetics study of radiolabeled E-S showed its rapid renal clearance after i.v. injection, with 4.96% ID/g of radiolabeled E-S retained in the tumor tissues at 24 h p.i. To study the in vivo labeling kinetics of E-S, E-S was i.v. administered to athymic nude mice bearing LS174T tumors, and tumors were harvested and sectioned at different time (8 h, 24 h, and 48 h) p.i. for the detection of expressed azido groups using DBCO-Cy5. Tumor tissue sections collected at 8 h p.i. showed significantly enhanced DBCO-Cy5 signal on the cell membranes compared to the control group without E-S treatment, suggesting that E-S successfully labeled tumor cells with azido groups (FIG. 7, panels e and f). Allowing more time (24 h or 48 h) for the metabolic labeling process of E-S in tumor cells, the amount of expressed azides significantly increased. It is noteworthy that no significant difference in the amount of cell surface azides between 24 h group and 48 h group tumor tissue sections was observed, presumably as a collective result of the fast labeling kinetics and limited tumor accumulation of E-S. We next studied whether more E-S injections would result in increased amount of azido groups in the tumor area. Tumor tissue sections from mice with two E-S injections showed significantly enhanced attachment of DBCO-Cy5 onto the cell surface, suggesting the increased amount of cell surface azides (FIG. 7, panel g). Three i.v. injections of E-S further improved the metabolic expression of azido groups by tumor cells. These results showed that multiple E-S injections with an interval of 24 h could continuously increase the amount of expressed azido groups in the tumor tissues.

E-S Mediated Cancer-Selective Labeling In Vivo:

(1) Western blot analysis of tissues. LS174T tumor models were established in 6 week-old athymic nude mice by subcutaneous injection of LS174T colon cancer cells (1.5 million) in HBSS/matrigel (1/1, v/v). When the tumors grew to 5-6 mm, E-S (60 mg/kg) was i.v. injected once daily for three days. Mice i.v. administered with $Ac_4ManAz$ (40 mg/kg, 10% DMSO in PBS) or PBS were used as control. At 24 h post the last injection, tumors and major organs were harvested, transferred into lysis buffer (2 mL), and homogenized. The lysates were incubated at 4° C. for 30 min, and insoluble debris was removed by centrifugation at 3000 rpm for 10 min. Total soluble protein concentrations were determined by BCA assay and adjusted to 5 mg/mL for each group. The rest of procedures were the same as the above-mentioned general procedures for western blot analysis. Azido-labeled protein bands in tumor tissues and healthy tissues of all three groups were visualized and compared to understand the cancer-selective labeling capability of E-S in vivo.

(2) In vivo and ex vivo biodistribution of DBCO-Cy5. In a separate study, when the tumors grew to 5-6 mm, E-S (60 mg/kg) was i.v. injected once daily for three days. Mice i.v. injected with $Ac_4ManAz$ (40 mg/kg) and PBS were used as control. At 24 h post the last injection, DBCO-Cy5 (10 mg/kg) was i.v. injected and its biodistribution was monitored via in vivo fluorescence imaging using the Bruker In-Vivo Xtreme Imaging System. Tumors and organs were harvested from mice at 48 h p.i. of DBCO-Cy5. Ex vivo images were collected similarly using the Bruker In-Vivo Xtreme Imaging System. Fluorescence intensity at selected ROIs was quantified using Bruker imaging software. All values were presented as means±standard deviation (n=3).

Tumor labeling kinetics of E-S in vivo. Athymic nude mice bearing subcutaneous LS174T tumors were i.v. injected with E-S (60 mg/kg). Mice without E-S injection were used as controls. At different time (8, 24, and 48 h) p.i. of E-S, tumors were harvested, frozen in O.C.T. compound, and sectioned with a thickness of 8 µm. Tumor tissue sections were incubated with 5% BSA for 2 h and then labeled with DBCO-Cy5 (20 µM) for 30 min. After washing with PBS, DAPI (2 µg/mL) and CellMask orange plasma membrane stain (1 µg/mL) were added to stain cell nuclei and membrane, respectively. Tumor tissue sections were imaged under a confocal laser scanning microscope. The imaging parameters were kept the same for all samples imaged. Data analyses were performed with the ZEN 2011 software. The mean Cy5 fluorescence intensity of each image was extracted and averaged over 20 images to obtain the mean Cy5 fluorescence intensity of each tissue section, which was then averaged over 20 tissue sections to obtain the mean Cy5 fluorescence intensity for each tumor.

Dose-dependent E-S mediated tumor labeling in vivo. Athymic nude mice (n=3 per group) bearing subcutaneous LS174T tumors were i.v. administered with E-S (60 mg/kg) for different times (one, two, or three injections) with a 24 h interval. Mice without E-S injection were used as controls. At 24 h post the last injection of E-S, tumors were harvested, frozen in O.C.T. compound, and sectioned with a thickness of 8 µm. Tumor tissue sections were stained, imaged, and analyzed following the procedures described above.

Example 9. Delivery of Anti-Cancer Agents Via Click Chemistry Reactions

Figure 8:
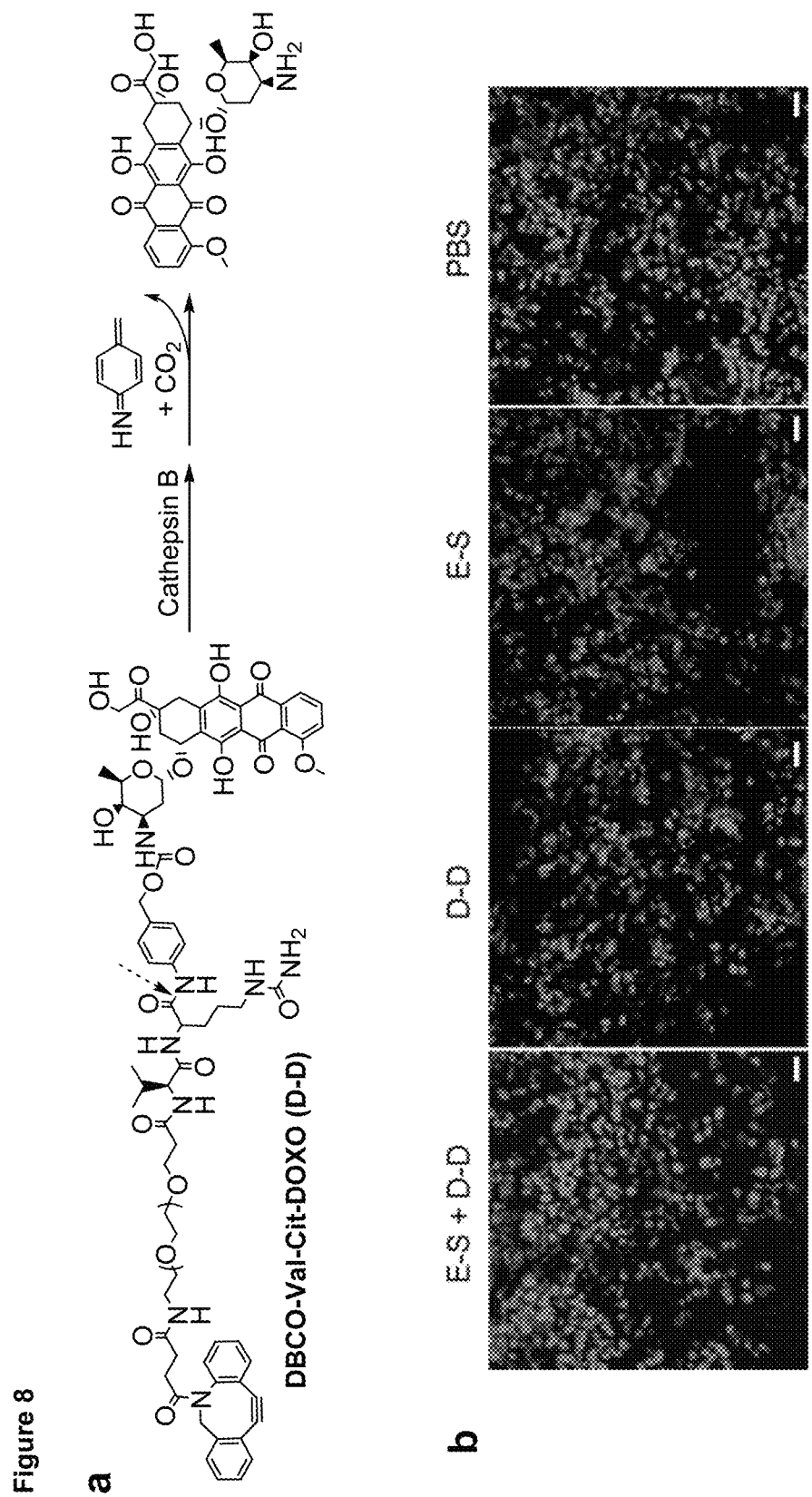
FIG. 8 consists of panels a-f, and demonstrates that E-S mediated tumor labeling improved antitumor efficacy of DBCO-drug conjugate against LS174T primary tumor model. Panel (a) shows the structure of Cathepsin B responsive DBCO-Val-Cit-DOXO (D-D). Panel (b) is a series of images showing representative TUNEL staining sections of LS174T tumors from different groups in an acute antitumor efficacy study. Scale bar: 50 μm. Panel (c) is a bar graph showing quantification of TUNEL stains via ImageJ. The apoptosis index was determined as the ratio of apoptotic cell number (TUNEL) to the total cell number (DAPI). 20 tissue sections were counted per tumor; n=4. Panel (d) is a graph showing average tumor size of each group over the course of the long-term efficacy study. Panel (e) contains Kaplan-Meier plots for all groups. Loss of mice was because of treatment-related death or non-treatment-related death or euthanasia after the predetermined end point was reached. Panel (f) contains a survival analysis of athymic nude mice in each group. TTE: time to end point. TGD: tumor growth delay; TGD=TTE (treated group)−TTE (PBS group). % TGD=100%×TGD/TTE (PBS group). All the numerical data were presented as mean±SEM and analyzed by one-way ANOVA (Fisher; 0.01<*P≤0.05; P≤0.01; *P≤0.001).

After demonstrating that E-S could selectively label cancer cells with azido groups in vivo and the expressed azido groups could well retain DBCO-Cy5 via Click reaction, we next investigated whether E-S pretreatment would lead to the enhanced anticancer efficacy of small molecule DBCO-drug conjugates. DBCO-doxorubicin conjugate (DBCO-Val-Cit-DOXO (D-D)) with a cathepsin B-cleavable linker was synthesized (FIG. 8, panel a). The linker was composed of a cathepsin B-cleavable dipeptide (val-cit), a self-immolative p-aminobenzylcarbomate (PABC) linker to reduce the steric hindrance during enzymatic degradation process, and a short polyethylene glycol (PEG) segment to improve water solubility. Synthesized D-D showed excellent stability under physiological conditions while underwent rapid release of free DOXO in the presence of activated cathepsin B. In vitro anticancer activity of D-D against LS174T cells was studied via MTT assay, which showed an $IC_{50}$ value of 2.5 µM. LS174T cells pretreated with E-S for three days showed significantly enhanced cellular uptake of D-D via Click reaction compared to control cells within a certain amount of incubation time (30 min, 1 h, and 42 h). Cellular fate of covalently attached DBCO-cargo by azido-modified cancer cells was investigated using fluorescent DBCO-Cy5 as a model compound, taking advantage of its low passive cellular uptake. After incubating with DBCO-Cy5 for 1 h and washing away the unbounded DBCO-Cy5, E-S pretreated LS174T cells were monitored under a fluorescence microscope. Negligible Cy5 signal in control cells without E-S pretreatment excluded the passive uptake of DBCO-Cy5. DBCO-Cy5 was covalently attached to the cell surface (overlay with cell membrane stain) first, and gradually entered lysosomes (overlay with lysotracker) over incubation time. Complete disappearance of DBCO-Cy5 on the cell membrane was observed when the cells were further incubated for 12 h. It can be imagined that covalently attached D-D will be able to release the drugs in the presence of cathepsin-B in cell lysosomes. Compared to free DOXO, D-D also showed significantly prolonged blood circulation. Next we studied whether E-S pretreatment would result in the enhanced tumor retention and accumulation of D-D and thus impart amplified therapeutic efficacy. In an acute anti-tumor efficacy study, athymic nude mice bearing subcutaneous LS174T tumors were i.v. administered with E-S or PBS once daily for three days (Day 0, 1 and 2), and i.v.

administered with drug D-D on Day 3. At 48 h p.i., tumors and major organs were harvested. Quantification of retained drugs in tissues showed a 1.46-fold tumor accumulation of D-D in mice treated with E-S compared to control mice-treated with PBS, while non-significant changes of D-D accumulation in liver, spleen, lung, heart, and kidney were observed (FIG. 8, panel (b)). Tumors treated with E-S/D-D showed an apoptosis index of 33.5±4.2%, which was significantly greater than that of tumors treated with D-D only (18.3±4.0%) (FIG. 8, panel (c)). As negative controls, tumors treated with E-S or PBS showed much lower apoptosis index, 1.5±0.6% or 1.7±0.5%, respectively (FIG. 8, panel (c)). These experiments confirmed that E-S mediated cancer-selective labeling could significantly improve the tumor accumulation and acute antitumor efficacy of D-D.

To further understand how the enhanced tumor accumulation of D-D mediated by E-S labeling would impart improved antitumor activity, a separate efficacy study was conducted by monitoring the tumor volume over a prolonged period. Athymic nude mice bearing LS174T tumors were divided into 4 groups: E-S+D-D, D-D, E-S, and PBS. As compared to PBS and E-S groups, E-S+D-D group exerted greater tumor growth inhibition (FIG. 8, pane d). Compared with D-D, E-S+D-D also significantly reduced tumor growth rate (FIG. 8, panel d). E-S+D-D improved the survival time of mice by 86.0% compared to PBS group, which was substantially greater than that of D-D (17.1%) (FIG. 8, panel e). Together, E-S+D-D exerted greatly improved anticancer efficacy than D-D only, as a result of the enhanced tumor accumulation of drugs via Click chemistry.

Metastatic cancers have been the leading cause of deaths of cancer patients as they can evade conventional cancer therapies such as surgery, radiation therapy, and chemotherapeutic therapy. Emerging cancer targeted therapies including antibody-based therapies have shown great potential in treating metastatic cancers. After demonstrating the excellent cancer targeting effect of E-S/D-D in primary colon tumor models, we went on to investigate whether the combinatory targeted therapy of E-S and D-D would be effective in inhibiting the growth of 4T1 lung metastatic cancers. Prior to the efficacy study, E-S mediated chemical labeling of 4T1 cancer cells in vitro was studied. As expected, E-S was able to efficiently label luciferase-engineered 4T1 cancer cells with azido groups in vitro which could significantly improve the cellular uptake of D-D via Click reaction. 4T1 metastatic cancers were established in BALB/c mice by i.v. injection of luciferase-engineered 4T1 cells on Day 0. After treatment with E-S once daily for three days (Day 1, 2, and 3), mice were administered with D-D or free DOXO (also labeled herein as Dox) starting from Day 4 to examine their efficacy in metastasis inhibition. The intensifying bioluminescence signals of PBS group mice over time confirmed the proliferation of 4T1 metastases in the lung parenchyma (FIG. 9, panel (b)). All drug treatment groups showed significantly reduced bioluminescence signals and tumor nodule counts in comparison with PBS and DCL-AAM groups (FIG. 9, panel (b)). Compared to D-D group, E-S+D-D group mice showed significantly reduced lung metastases, as evidenced by the reduced bioluminescence signals (FIG. 9, panels b and c), a smaller amount of tumor nodules (47.9±7.1% versus 67.4±13.5%) (FIG. 9, panel d), and a decreased percentage of tumor surface area (18.2±8.3% versus 38.2±10.4%) (FIG. 9, panels e and f). Despite resulting in the similar lung metastases severity to E-S+D-D, Doxo exerted much greater toxicity in mouse tissues, especially in bone marrow and spleen (FIG. 9, panel g). Together, E-S+D-D exerted the best anticancer efficacy with greatly reduced toxicity, as a collective result of enhanced tumor accumulation of D-D via Click chemistry and its cancer-preferential drug release imparted by cathepsin B activity differences between cancerous and normal tissues.

Synthetic Route of DBCO-Val-Cit-DOXO (D-D)

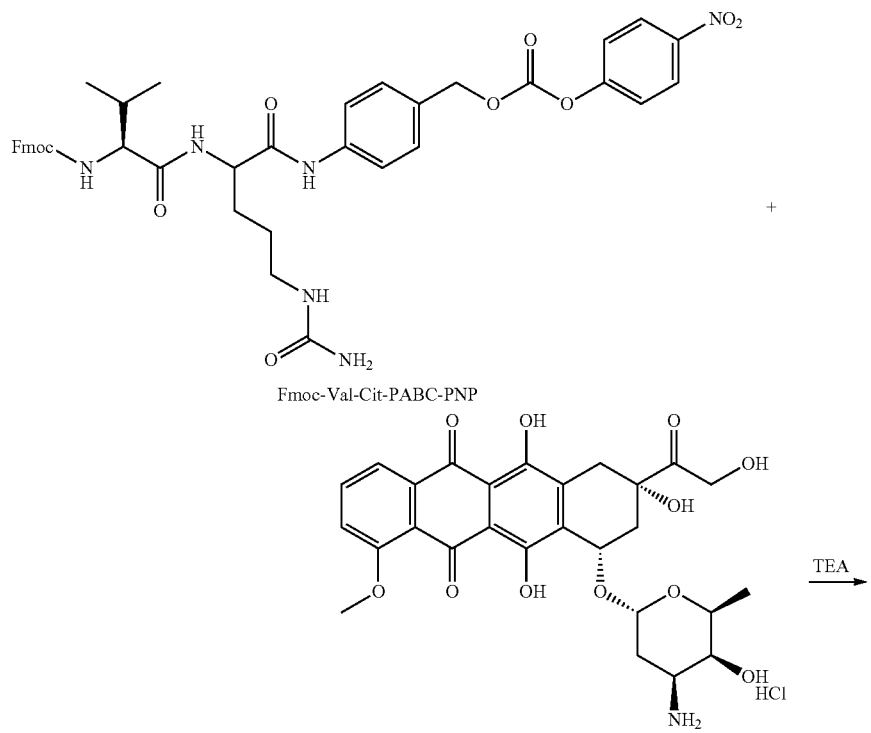

-continued
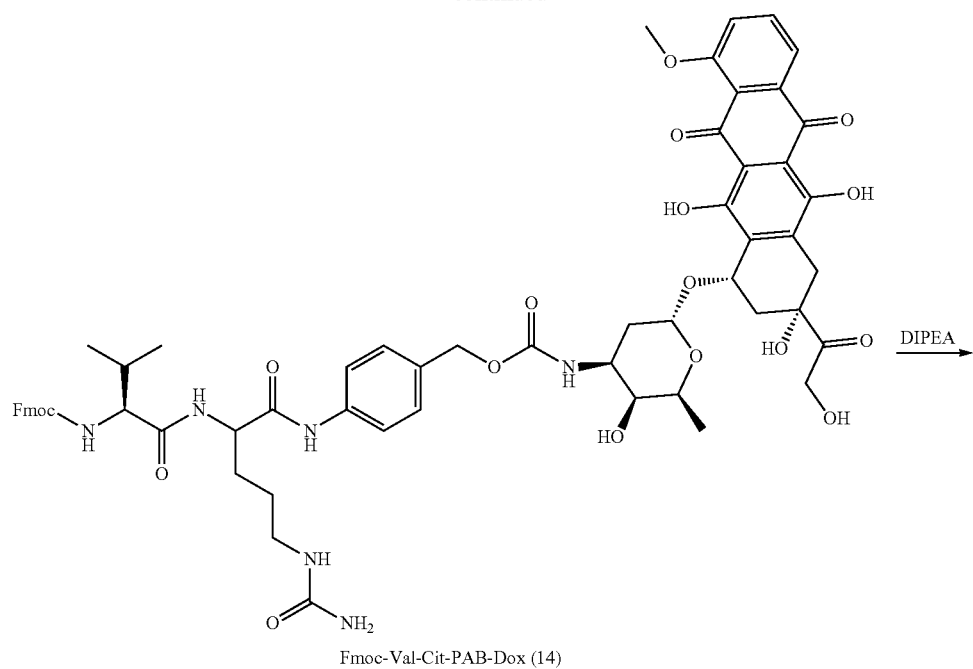
Fmoc-Val-Cit-PAB-Dox (14)
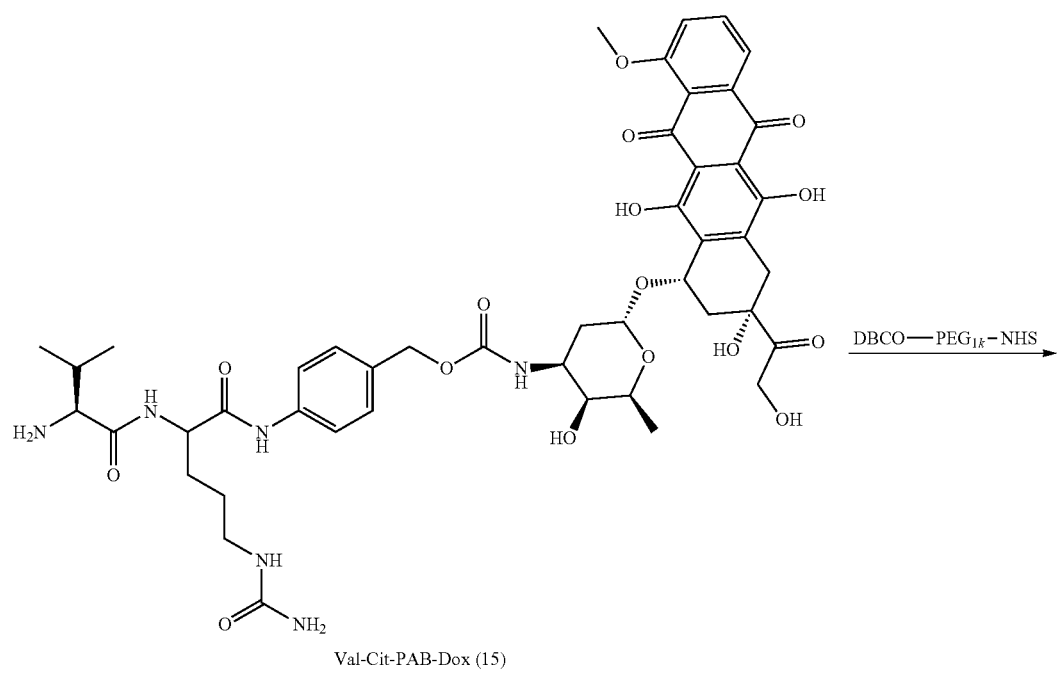
Val-Cit-PAB-Dox (15)

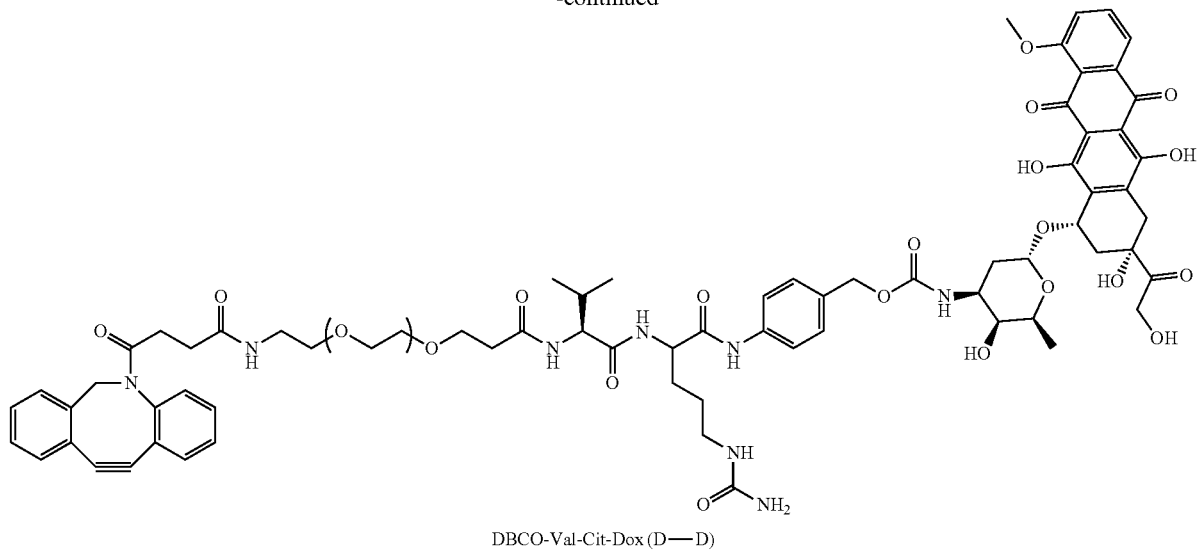

DBCO-Val-Cit-Dox (D—D)

Synthesis of DBCO-PEG$_{1k}$-NHS. DBCO-NHS (0.11 mmol, 44 mg) and NH$_2$—PEG$_{1k}$-COOH (0.1 mmol, 100 mg) were dissolved in anhydrous DMF (1.5 mL), followed by the addition of trimethylamine (0.11 mmol, 11 mg). The mixture was stirred at 45° C. for 24 h. DCC (0.12 mmol, 25 mg) and NHS (0.12 mmol, 14 mg) in DMF were added. The reaction mixture was further stirred at 45° C. for 24 h. The precipitate was filtered off and the filtrate was ultracentrifuged (repeat twice) with a cut-off molecular weight of 1 k. The residual solution was diluted with DCM, collected, and concentrated to yield a light yellow solid (70% yield).

Synthesis of DBCO-Val-Cit-DOXO (D-D). Doxorubicin hydrochloride (0.05 mmol, 29 mg) and Fmoc-Val-Cit-PAB-PNP (0.05 mmol, 38 mg) were dissolved in anhydrous DMF (1 mL). Triethylamine (0.06 mmol, 6 mg) was added and the mixture was stirred at 40° C. under nitrogen atmosphere. HPLC measurement showed complete consumption of Fmoc-Val-Cit-PAB-PNP after 12 h, at which point diisopropylethylamine (100 µL) was added in one portion. The color of reaction mixture turned dark immediately. After 12 h, the cleavage of Fmoc group was complete, as confirmed by the peak shift in HPLC profiles. DBCO-PEG$_{1k}$-NHS (0.05 mmol, 65 mg) in DMF (100 µL) was added and the mixture was stirred at 40° C. for another 24 h. The reaction solution was concentrated and precipitated into diethyl ether to yield a red solid. After washing with diethyl ether twice, the solid was redissolved in methanol and dialyzed against methanol for 48 h (1 k cut-off molecular weight) to get rid of small molecules. The residue solution was collected and concentrated to yield a red solid (65% yield).

Cathepsin B-induced degradation of D-D. A stock solution of bovine spleen cathepsin B was prepared by dissolving the lyophilized solid (2.1 mg) to 1 mL of a 25 mM sodium acetate/1 mM EDTA buffer (pH=5.0). 15 µL. of the stock solution was activated on ice by adding a solution of 30 mM DTT/15 mM EDTA (30 µL) and incubating for 30 min. The activated cathepsin B was then diluted with 2 mL of sodium acetate/EDTA buffer (pH 5.0). D-D in methanol (10 mM, 10 µL) was added to the activated enzyme solution, and the mixture was incubated at 37° C. 20 µL aliquots of the mixture were taken out at selected time points and diluted to 600 µL for HPLC measurements.

MTT study of D-D and free DOXO. LS174T cells were seeded in a 96-well plate at an initial density of 4 k cells/well, allowed to attach for 24 h and treated with free DOXO or D-D of various DOXO concentrations at 37° C. for 72 h. Cells treated with PBS were used as control. The MTT assay was performed by following the standard procedure.

Uptake of D-D in E-S treated LS174T cells. LS174T cells were seeded in a 24-well plate, and incubated with E-S (50 µM) for three days. Cells without E-S pretreatment were used as control. After removing the old medium and washing with PBS for three times, D-D (20 µM) in OptiMEM was added at different time points (4 h, 2 h, 1 h, and 30 min prior to sample preparation for flow cytometry analysis). OptiMEM was then removed and cells were washed with PBS for three times. Cells were detached by colorless trypsin, and transferred to flow tubes with the addition of 4% PFA for flow cytometry analysis.

Uptake mechanism of DBCO-Cy5 or D-D in vitro. LS174T cells were seeded onto a tissue culture dish with cover glass bottom, and incubated with E-S (50 µM) for three days. After multiple washing with PBS, Lysotracker green in fresh medium was added and incubated for 1 h. Then DBCO-Cy5 was added and cells were further incubated for 1 h. Hoechst 33342 (10 µg/mL) and CellMask orange plasma membrane stain (1 µg/mL) were added to stain cell nucleus and cell membrane, respectively for 10 min. After removing the medium and washing with PBS, cells were further incubated at 37° C. At different time points (1 h, 3 h, 6 h, 12 h, and 24 h), cells were imaged under a fluorescence microscope to monitor the uptake of DBCO-Cy5. Cells without E-S pretreatment were used as control. For live cell imaging of D-D treated cells, CellMask deep red plasma membrane stain was used to stain cell membrane and lysosomes were not stained to avoid the interference over fluorescence signals of D-D.

Pharmacokinetics study of D-D and free DOXO. To evaluate its circulation half-life, D-D (5 mg/kg in DOXO equivalent) or free DOXO (5 mg/kg) was i.v. injected into female athymic nude mice (n=3) via tail veins. At selected time points (10 min, 30 min, 1 h, 2 h, 4 h, 6 h, 12 h, and 24 h post injection), blood was collected through orbital sinus. The collected blood samples (25 µL) were diluted with a mixture of methanol/H$_2$O (1/1, v/v, 75 µL), and vortexed for 10 min. After centrifuged at 12000 rpm for 10 min, the supernatant was transferred to a black 96-well plate for fluorescence measurement. A gradient concentrations of D-D or free DOXO were used for the determination of the standard curve. The plasma concentration of D-D or free DOXO was calculated in µg/mL.

Acute efficacy study of E-S/D-D against subcutaneous LS174T colon tumors. LS174T tumors were established in 6 week-old female athymic nude mice by subcutaneous injection of LS174T colon cancer cells (1.5 million cells) in HBSS/matrigel (1/1, v/v, 50 µL) into both flanks. When the tumors reached ~50 mm$^3$, mice were randomly divided into 4 groups (group 1: E-S/D-D; group 2: D-D; group 3: E-S; group 4: PBS; n=3). For group 1 and group 3, E-S (60 mg/kg) was i.v. injected once daily for three days (Days 0, 1, and 2). Mice in the other two groups were i.v. injected with PBS as control. At 24 h post the last injection of E-S, D-D (10 mg/kg in DOXO equivalent) or PBS was i.v. injected. At 48 h post injection, tumors were harvested and bisected. Half the tumors were frozen with O.C.T. compound, sectioned with a thickness of 8 µm and analyzed for apoptosis via terminal deoxynucleotidyl transferase dUTP nick end labeling (TUNEL) assay. Organs and the other half of the tumors were weighed, homogenized, and lysed. After the addition of acidified isopropanol, the mixture was vortexed and frozen overnight at −20° C. After centrifugation the supernatant was injected into HPLC for the quantification of retained DOXO in tissues. Data were presented as % I.D./g.

Long-term tumor reduction efficacy of E-S/D-D against subcutaneous LS174T tumors. LS174T tumors were established in 6 week-old female athymic nude mice by subcutaneous injection of LS174T cells (1.5×10$^6$ cells in HBSS/matrigel (1/1, v/v, 50 µL)) into both flanks. When the tumors reached ~50 mm$^3$, mice were randomly divided into 4 groups (group 1: E-S/D-D; group 2: D-D; group 3: E-S; group 4: PBS; n=5-6). For group 1 and group 3 mice, E-S (60 mg/kg) was i.v. injected on Day 0, 1, and 2. Mice in the other two groups were i.v. injected with PBS as control. D-D (12 mg/kg in Dox equivalent) or PBS was i.v. injected on Day 3, 7, and 11. Tumor volume and body weight of mice were measured every other day. The tumor volume was calculated using the formula (length)×(width)$^2$/2, where the long axis diameter was regarded as the length and the short axis diameter was regarded as the width. When the tumor volume reached 2000 mm$^3$ (as predetermined endpoint) or the animal had become moribund or the body weight loss was beyond 20% of original weight, the animal was sacrificed. When an animal exited the study due to tumor volume or treatment related death, the final tumor volume recorded for the animal was used to calculate the mean tumor volume at subsequent time points. The time to endpoint (TTE) of each animal was defined as the day when its tumor volume had reached the predetermined endpoint. Animals classified as treatment-related deaths were assigned a TTE value equal to the day of death. Treatment efficacy was determined by tumor growth delay (TGD), which was defined as the increase in the median TTE in a treatment group compared to the control (PBS) group: TGD=TTE(T)−TTE(C) which was expressed in days, or as a percentage of the median TTE of the control group: % TGD=100%×(TTE(T)−TTE(C))/TTE(C).

MB-MDA Breast Cancer Model

E-S mediated in vitro labeling of MDA-MB-231 cells. MDA-MB-231 breast cancer cells were seeded onto coverslips in a 6-well plate at a cell density of 40 k/well. E-S with a final concentration of 50 µM was added, followed by the addition of either TSA (1 µM) or Z-FY-CHO (50 µM). Cells treated with PBS or E-S only were used as control. After 72-h incubation, the medium was removed and cell samples for confocal imaging and IN cell Analyzer measurements were prepared following the above-mentioned procedures.

D-D uptake in E-S labeled MDA-MB-231 cells. Cells were seeded in a 24-well plate at a density of 1×10$^4$ cells per well and incubated with E-S (50 µM) or PBS for three days. After washing with PBS, the cells were incubated with D-D (20 µM) for different time (30 min, 1 h, 2 h, and 4 h), lysed, and measured on a plate reader for fluorescence intensity of D-D. After fluorescence measurements, protein concentration in each well was determined via BCA assay. The final data were presented as fluorescence intensity of D-D per milligram protein.

MTT assay of D-D and free DOXO against MDA-MB-231 cells. MDA-MB-231 breast cancer cells were seeded in a 96-well plate at an initial density of 4 k cells/well, allowed to attach for 12 h and treated with free DOXO or D-D of various DOXO concentrations at 37° C. for 72 h. Cells treated with PBS were used as control. The MTT assay was performed by following the standard procedures.

Long-term tumor reduction efficacy of E-S+D-D against subcutaneous MDA-MB-231 breast tumors. MDA-MB-231 tumors were established in 6 week-old female athymic nude mice by subcutaneous injection of MDA-MB-231 cells (1.5×10$^6$ cells in HBSS/matrigel (50 µL, 1/1, v/v)) into both flanks. When the tumors reached ~50 mm$^3$, mice were randomly divided into 4 groups (group 1: E-S+D-D; group 2: D-D; group 3: E-S; group 4: PBS; n=5). E-S (60 mg/kg) was i.v. injected to group 1 and group 3 mice once daily for three consecutive days (Day 0, 1, and 2). D-D (12 mg/kg in Doxo equivalent) was i.v. injected on Day 3, 7, and 11. Tumor volume and body weight of each mouse were measured every four days. The endpoint of tumor volume was set at 1500 mm$^3$. Data analyses were the same as the abovementioned long-term efficacy study against LS174T tumors.

4T1 Metastatic Cancer Model

E-S mediated in vitro labeling of 4T1 cells. Luciferase-engineered 4T1 breast cancer cells were seeded onto coverslips in a 6-well plate at a cell density of 40 k/well. E-S with a final concentration of 50 µM was added, followed by the addition of either TSA (1 µM) or Z-FY-CHO (50 µM). 4T1 Cells treated with PBS or E-S only were used as control. After 72-h incubation, the medium was removed and cells were analyzed by confocal microscope and flow cytometry.

D-D uptake of E-S labeled 4T1 cells. Luciferase-engineered 4T1 cells were seeded in a 96-well black plate, and incubated with E-S (50 µM) for three days. Cells without E-S pretreatment were used as control. After removing the medium and washing with PBS for three times, D-D (20 µM) in OptiMEM was added at different time points (4 h, 2 h, 1 h, and 30 min prior to sample preparation). OptiMEM was then removed and cells were washed with PBS twice. 100 µL of lysis buffer was then added to each well, and fluorescence intensity of internalized D-D in each well was measured on a plate-reader. After fluorescence measurements, protein concentration in each well was determined via BCA assay. The final data were presented fluorescence intensity of D-D per milligram protein (D-D uptake/mg protein).

MTT assay of D-D and free DOXO against 4T1 cells. Luciferase-engineered 4T1 cells were seeded in a 96-well plate at an initial density of 4 k cells/well, allowed to attach for 12 h and treated with free DOXO or D-D of various DOXO concentrations at 37° C. for 72 h. Cells treated with PBS were used as control. The MTT assay was performed by following the standard procedure.

Anticancer efficacy study against 4T1 metastatic cancers in Balb/c mice. 4T1 metastatic cancer model was established by tail vein injection of luciferase-engineered 4T1 cells ($1\times10^5$ cells in 200 μL HBSS) into 6-week old BALB/c mice on Day 0. Mice were then randomly divided into 5 groups (group 1: E-S+D-D; group 2: D-D; group 3: Dox; group 4: E-S; group 5: PBS; n=7-8). E-S (60 mg/kg) was i.v. injected once daily for three days (Day 1, 2, and 3). D-D (12 mg/kg in Doxo equivalent) or Doxo (7.5 mg/kg, maximum tolerated dose) was i.v. injected on Day 4, 8, and 12. Body weight and food intake of each mouse were measured every other day. Lung metastases were monitored via bioluminescence imaging of BALB/c mice using the Bruker In-Vivo Xtreme imaging system every four days starting from Day 5. D-luciferin potassium salt (150 mg/kg) was intraperitoneally injected at 3 min prior to imaging. Bioluminescence imaging data were processed using the Bruker imaging software. After the last imaging on Day 13, all mice were sacrificed under anesthesia. The lung and heart of each animal were resected as a whole, weighed, and injected with 10% formalin into trachea until the lungs inflated. Tumor nodules on lungs (n=7-8 per group) were counted under a dissecting microscope. Each lung lobe was separated after fixation in formalin. All lung tissues were paraffin-embedded, sectioned with a thickness of 4 and stained with H&E. All the lung sections were then scanned and analyzed. The surface areas of tumors and lungs were measured to calculate the percentage of tumor surface area over the total lung surface area ($A_{tumor}/A_{total}$).

Toxicity evaluation of E-S+D-D and free DOXO. Liver, heart, kidneys, spleen, brain, sternum and spinal cord (cervical thoracic and lumbar) were fixed in formalin, paraffin-embedded, sectioned with a thickness of 4 μm, and stained with H&E. Tissues were analyzed by a board-certified pathologist to investigate treatment-mediated toxicity. These analyses were performed by a board certified pathologist.

Statistical analysis. The statistical analysis was performed by one-way analysis of variance (ANOVA) with post hoc Fisher's LSD test (OriginPro 8.5), and P-values<0.05 were considered statistically significant. The results were deemed significant at $0.01<*P\leq0.05$, highly significant at $0.001<P\leq0.01$, and extremely significant at $*P\leq0.001$. Sample size was empirically set at n=3-6 for in vitro cell experiments, n=3-4 for in vivo biodistribution and imaging studies, n=5-6 for xenograft tumor studies, and n=7-8 for metastatic tumor studies.

Example 10. Animal Data in TNBC Model

Figure 10:
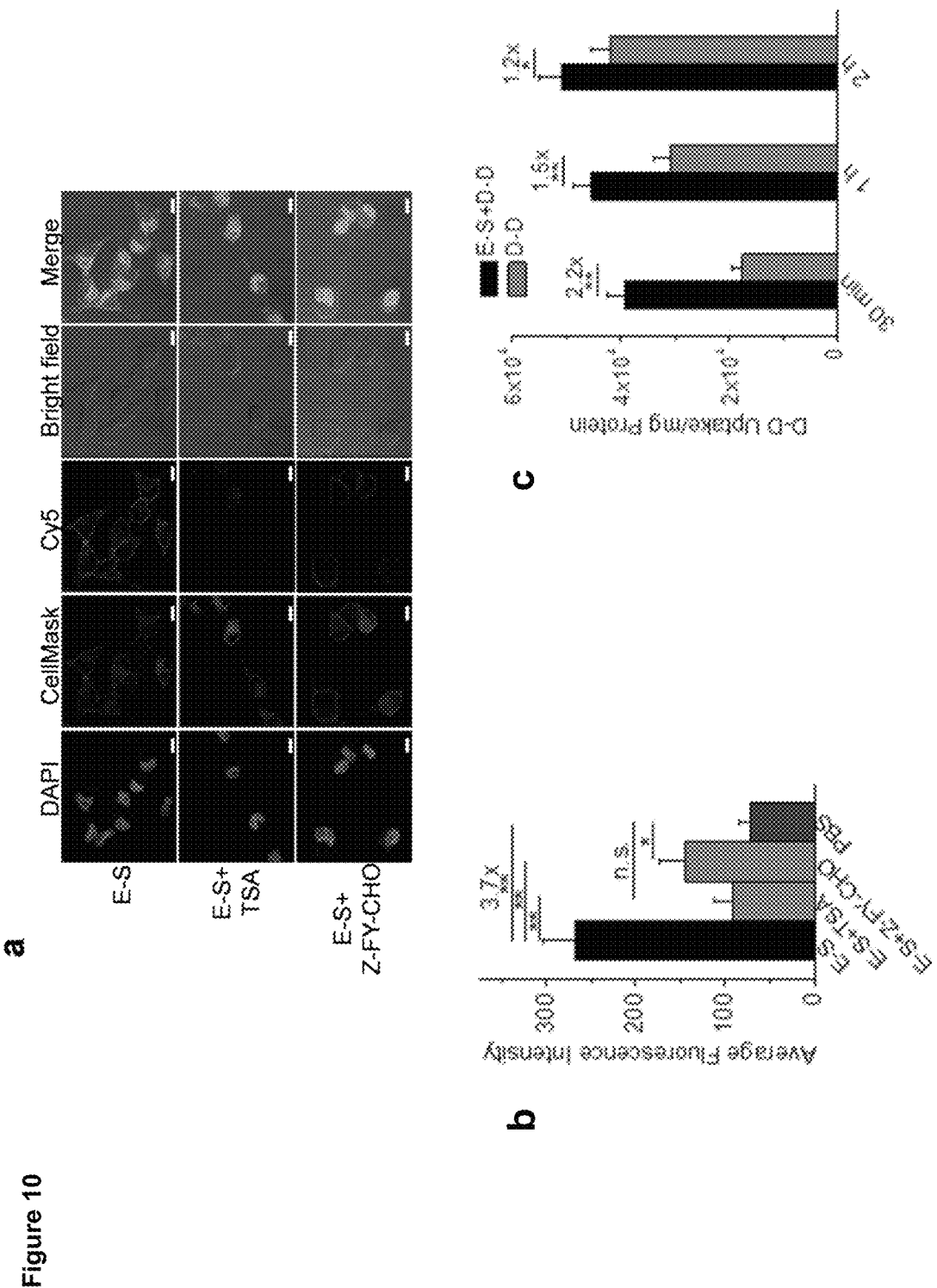
FIG. 10 consists of panels a-d. Panel shows (a) CLSM images of MDA-MB-231 breast cancer cells after incubation with 50 µM E-S, 50 µM E-S+1 µM TSA, and 50 µM E-S+50 µM Z-FY-CHO, respectively for 72 h and labeled with DBCO-Cy5 for 1 h. The cell nucleus and cell membrane were stained with DAPI and CellMask Orange Plasma Membrane Stain, respectively. Scale bar: 10 µm. Panel (b) is a bar graph showing average Cy5 fluorescence intensity of MDA-MB-231 cells after incubation with 50 µM E-S, 50 µM E-S+1 µM TSA, and 50 µM E-S+50 µM Z-FY-CHO, respectively for 72 h and labeled with DBCO-Cy5 for 1 h. Panel (c) is a bar graph showing D-D uptake by MDA-MB-231 breast cancer cells with or without E-S pretreatment (72 h) over different incubation time (30 min, 1 h, and 2 h). All the numerical data were presented as mean±SEM and analyzed by one-way ANOVA (Fisher; 0.01<*P≤0.05; P≤0.01; *P≤0.001).

Triple-negative breast cancers, characterized by the limited expression of estrogen receptors, progesterone receptors, and Her2, nullified multiple conventional antibody therapies for breast cancers. We were interested in investigating whether E-S mediated labeling of triple-negative MDA-MB-231 breast cancer cells with azides would improve the tumor accumulation and anticancer efficacy of DBCO-drug conjugates (e.g., D-D). Labeling capability of E-S in MDA-MB-231 breast cancer cells in vitro was evaluated first. After incubating with E-S for three days and DBCO-Cy5 for 1 h, strong Cy5 fluorescence on the cell membrane was observed (FIG. 10, panel a), indicating the successful expression of azido groups. Both TSA and Z-FY-CHO significantly decreased the labeling efficiency of E-S (FIG. 10, panel b), which validated HDAC/CTSL induced reactivation of metabolic labeling process of E-S in MDA-MB-231 breast cancer cells. E-S pretreatment was able to enhance the uptake of D-D within a certain amount of incubation time (30 min, 1 h, and 2 h) in vitro (FIG. 10, panel d). We then investigated whether E-S mediated labeling of MDA-MB-231 tumor cells would improve the accumulation and antitumor efficacy of D-D. Athymic nude mice bearing subcutaneous MDA-MB-231 primary tumors were divided into 4 groups: E-S+D-D, D-D, E-S, and PBS. E-S was i.v. administered on Day 0, 1, and 2. D-D was i.v. administered on Day 3, 7, and 11 (FIG. 11, panel a). Compared to PBS group, E-S group showed negligible difference in tumor growth rate (FIG. 11, panel b), excluding the influence of E-S alone on the antitumor effect. Both drug treatment groups showed significantly reduced tumor growth rate compared to PBS group, with a median TTE value of 62.6 and 29.0, respectively (FIG. 11, panel b, c, and d). Compared to D-D group, E-S+D-D group showed much better antitumor efficacy with a significantly smaller tumor size from as early as Day 24 (FIG. 11, panel b, c, and d), presumably as a result of E-S mediated tumor labeling and the improved tumor accumulation and retention of D-D.

REFERENCES CITED

1. Brandley, B. K. & Schnaar, R. L. Cell-surface carbohydrates in cell recognition and response. *Journal of Leukocyte Biology* 40, 97-111 (1986).
2. Stoolman, L. M. & Rosen, S. D. Possible role for cell-surface carbohydrate-binding molecules in lymphocyte recirculation. *The Journal of cell biology* 96, 722-729 (1983).
3. Dabelsteen, E. Cell surface carbohydrates as prognostic markers in human carcinomas. *The Journal of pathology* 179, 358-369 (1996).
4. Gorelik, E., Galili, U. & Raz, A. On the role of cell surface carbohydrates and their binding proteins (lectins) in tumor metastasis. *Cancer and Metastasis Reviews* 20, 245-277 (2001).
5. Fukuda, M. Possible roles of tumor-associated carbohydrate antigens. *Cancer research* 56, 2237-2244 (1996).
6. Prescher, J. A., Dube, D. H. & Bertozzi, C. R. Chemical remodelling of cell surfaces in living animals. *Nature* 430, 873-877 (2004).
7. Laughlin, S. T. & Bertozzi, C. R. Metabolic labeling of glycans with azido sugars and subsequent glycan-profiling and visualization via Staudinger ligation. *Nature protocols* 2, 2930-2944 (2007).
8. Saxon, E. et al. Investigating cellular metabolism of synthetic azidosugars with the Staudinger ligation. *Journal of the American Chemical Society* 124, 14893-14902 (2002).
9. Laughlin, S. T., Baskin, J. M., Amacher, S. L. & Bertozzi, C. R. In vivo imaging of membrane-associated glycans in developing zebrafish. *Science* 320, 664-667 (2008).
10. Chang, P. V. et al. Metabolic labeling of sialic acids in living animals with alkynyl sugars. *Angewandte Chemie International Edition* 48, 4030-4033 (2009).
11. Breidenbach, M. A. et al. Targeted metabolic labeling of yeast N-glycans with unnatural sugars. *Proceedings of the National Academy of Sciences* 107, 3988-3993 (2010).

We claim:

1. A compound or a pharmaceutically acceptable salt thereof, comprising:
   an optionally substituted N-((azido)acyl) 2-amino-2-deoxy-D-mannopyranosyl moiety;
   a trigger-responsive moiety; wherein the trigger-responsive moiety comprises an amino acid comprising an amide bond that is cleaved by a cathepsin enzyme; and
   a self-immolative linker; wherein
   the self-immolative linker is an optionally substituted —((C1)alkylene)-arylene; and
   the self-immolative linker is covalently bonded at one end to the trigger-responsive moiety via an amide bond; and
   the self-immolative linker is covalently bonded at the other end to the anomeric-C1 site of the mannopyranosyl moiety via a glycosidic ether bond.

2. The compound of claim 1 represented by formula (I) or a pharmaceutically acceptable salt thereof:

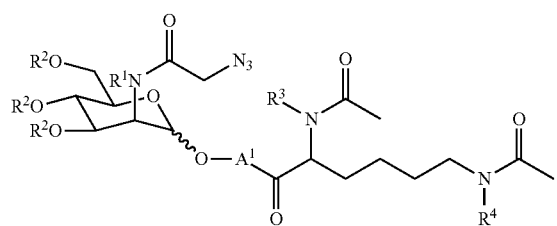

(I)

wherein:
   $R^1$ represents H or tri(($C_1$-$C_6$)alkyl)silyl;
   $R^2$, independently for each occurrence, represents H or —C(O)(($C_1$-$C_6$)alkyl);
   $R^3$ and $R^4$, independently for each occurrence, represent H, tri(($C_1$-$C_6$)alkyl)silyl, or —C(O)(($C_1$-$C_6$)alkyl); and
   $A^1$ represents the self-immolative linker.

3. The compound of claim 2, wherein the self-immolative linker is selected from the group consisting of:

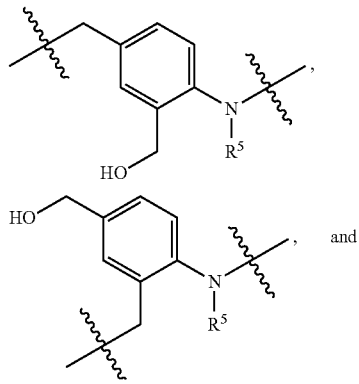

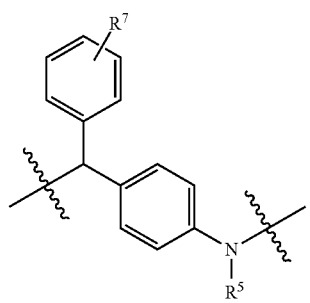

wherein
   $R^5$ represents H, tri(($C_1$-$C_6$)alkyl)silyl, or —C(O)(($C_1$-$C_6$)alkyl);
   $R^7$ represents H, halo, —C(O)$_2$H, ($C_1$-$C_6$)alkoxy, di(($C_1$-$C_6$)alkyl)amino, —NO$_2$, —O(CH$_2$CH$_2$O)$_q$CH$_3$; and
   q is 1 or 2.

4. The compound of claim 1, represented by:
   (a) formula (II) or a pharmaceutically acceptable salt thereof:

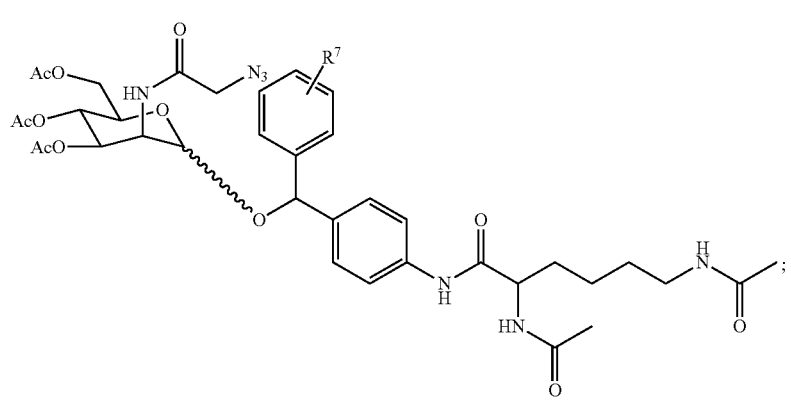

(II)

wherein $R^7$ represents H, halo, —C(O)$_2$H, ($C_1$-$C_6$)alkoxy, di(($C_1$-$C_6$)alkyl)amino, —NO$_2$, —O(CH$_2$CH$_2$O)$_q$CH$_3$; and q is 1 or 2; or
(b) formula (II') or a pharmaceutically acceptable salt thereof:
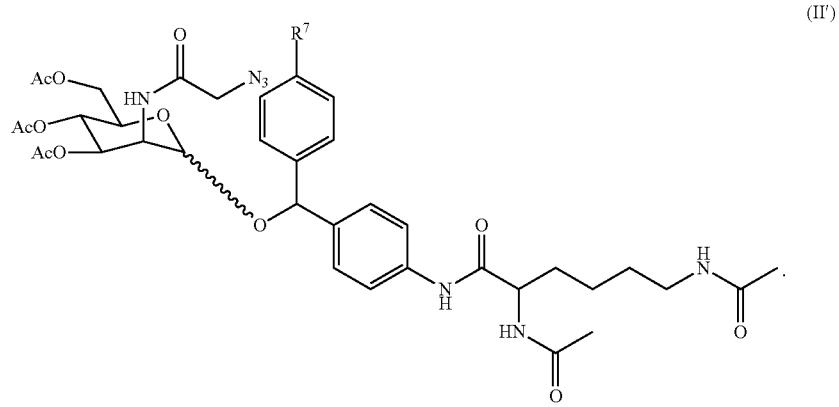
(II')
5. A pharmaceutical composition, comprising a compound of claim 1, and a pharmaceutically acceptable excipient or carrier.
6. The compound of claim 1, wherein the cathepsin enzyme is cathepsin B or cathepsin L.
* * * * *